US010828336B2

(12) United States Patent
Stewart

(10) Patent No.: US 10,828,336 B2
(45) Date of Patent: *Nov. 10, 2020

(54) CELL-BASED THERAPY FOR THE PULMONARY SYSTEM

(71) Applicant: NORTHERN THERAPEUTICS, INC., Montreal (CA)

(72) Inventor: Duncan John Stewart, Toronto (CA)

(73) Assignee: Northern Therapeutics Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,789

(22) Filed: Feb. 27, 2017

(65) Prior Publication Data

US 2017/0312317 A1 Nov. 2, 2017

Related U.S. Application Data

(60) Division of application No. 11/696,039, filed on Apr. 3, 2007, now Pat. No. 9,585,916, which is a continuation-in-part of application No. 10/236,980, filed on Sep. 9, 2002, now abandoned, which is a continuation-in-part of application No. 09/404,652, filed on Sep. 24, 1999, now Pat. No. 6,482,406, which is a continuation-in-part of application No. 09/276,654, filed on Mar. 26, 1999, now Pat. No. 6,592,864.

(60) Provisional application No. 60/079,588, filed on Mar. 27, 1998.

(51) Int. Cl.
| | |
|---|---|
| A61K 35/36 | (2015.01) |
| A61K 35/12 | (2015.01) |
| A61K 38/18 | (2006.01) |
| A61K 48/00 | (2006.01) |
| C12N 5/071 | (2010.01) |
| C12N 5/077 | (2010.01) |

(52) U.S. Cl.
CPC .............. *A61K 35/36* (2013.01); *A61K 35/12* (2013.01); *A61K 38/1858* (2013.01); *A61K 48/005* (2013.01); *A61K 48/0008* (2013.01); *C12N 5/0656* (2013.01); *C12N 5/0691* (2013.01); *C12N 2510/02* (2013.01)

(58) Field of Classification Search
None
See application file for complete search history.

(56) References Cited

U.S. PATENT DOCUMENTS

| 5,219,740 A | 6/1993 | Miller et al. |
| 5,656,598 A | 8/1997 | Dunstan et al. |
| 5,658,565 A | 8/1997 | Billiar et al. |
| 5,785,965 A | 7/1998 | Pratt |
| 5,792,453 A | 8/1998 | Hammond et al. |
| 5,830,879 A | 11/1998 | Isner |
| 5,910,488 A | 6/1999 | Nabel et al. |
| 5,916,803 A | 6/1999 | Sedlacek et al. |
| 5,941,868 A | 8/1999 | Kaplan et al. |
| 6,482,406 B1 * | 11/2002 | Stewart .............. A61K 48/0008 424/93.1 |
| 6,592,864 B1 * | 7/2003 | Stewart ............... C12N 5/0691 424/93.1 |
| 9,585,916 B2 * | 3/2017 | Stewart .................. A61K 35/12 |
| 9,827,270 B2 * | 11/2017 | Stewart .................. A61K 35/12 |

FOREIGN PATENT DOCUMENTS

| CA | 2086844 A1 | 10/2010 |
| WO | WO92/15676 A1 | 9/1992 |
| WO | WO93/13807 A1 | 7/1993 |
| WO | WO98/19712 A1 | 5/1998 |

OTHER PUBLICATIONS

Hegeman, et al. (2010) "Angiopoietin-1 Treatment Reduces Inflammation but Does Not Prevent Ventilator-Induced Lung Injury", PLoS ONE, 5(2) article e15653, 9 pages long.*
Denu, et al. (2016) "Fibroblasts and Mesenchymal Stromal/Stem Cells are Phenotypically Indistinguishable", Acta Hematologica, 136(2): 85-97.*
Witzenrath, et al. (2006) "Allergic lung inflammation induces pulmonary vascular hyperresponsiveness", The European Respiratory Journal, 28(2): 370-77 (printed as Epub, 32 pages).*
Puneet, et al. (2005) "Chemokines in acute respiratory distress syndrome", American Journal of Physiological Cell and Molecular Physiology, 288: L3-15.*
Game et al. (2001) Wien Klin Wochenschr, 113: 832-38.*
Schachtner, S.K. et el. In vivo adenovirus-mediated gene transfer via the pulmonary artery of rats; Circ. Res.; 1995; 76:701-709.
Nabel, E.G. et al.; Safety and toxicity of catheter gene delivery to the pulmonary vasculature in a patient with metastatic melanoma; Hum. Gene Ther.; 1994; 5:1089-1094.
McCluski et al., Molecular Medicine, 1999, "Route and Method of Delivery of DNA Vaccine Influence Immune Responses in Mice and Non-Human Primates".
Moldawer et al., Shock, vol. 12, No. 2, 1999, "Applications of Gene Therapy to Acute Inflammatory Diseases".
Teichert-Kuliszewska et al., Circ Res, 1998, "Role of Nitric Oxide in the Angiogenic Response in vitro to Basic Fibroblast Growth Factor".
Morbidelli et al., Adv Prostaglandin Thomboxane Leukot Res, 1995, "Nitric Oxide Modulates Angiogenesis Elicited by Prostaglandin E1 in Rabbit Cornea".

(Continued)

*Primary Examiner* — Robert M Kelly
(74) *Attorney, Agent, or Firm* — Ramey & Schwaller, LLP; William P. Ramey; Melissa D. Schwaller

(57) ABSTRACT

Cell based therapy comprises administration to the lung by injection into the blood system of viable, mammalian cells effective for alleviating or inhibiting pulmonary disorders. The cells may express a therapeutic transgene or the cells may be therapeutic in their own right by inducing regenerative effects.

5 Claims, 42 Drawing Sheets

Specification includes a Sequence Listing.

(56) References Cited

OTHER PUBLICATIONS

Symes et al., Ann Thorac Surg, 1999, Gene therapy with vascular endothelial growth factor for inoperable coronary artery disease?.
Falqui et al., Hum Gene Ther, 1999, "Reversal of diabetes in mice by implantation of human fibroblasts genetically engineered to release mature human insulin".
Chun et al., American Physiological Society, 1996, "Developmental expression of NOS isoforms in fetal rat lung: implications for transitional circulation and pulmonary angiogenesis".
Dunphy et al., Hum Gene Ther, 1999, "Reciprocal enhancement of gene transfer by combinatorial adenovirus transduction and plasmid DNA transfection in vitro and in vivo".
Zuidam et al., Int J Pharm., 1999, "Characterization of DNA-lipid complexes commonly for gene delivery".
Yao et al., J Biol Chem, 1999, "The transcription factor EGR-1 supresses transformation of human fibrosarcoma HT1080 cells by coordinated induction of transforming growth factor-beta 1, fibronectin, and plasminogen activator inhibitor-1".
Rosengart et al., Circulation, 1999, "Angiogenesis for therapy: phase I assessment of direct intramyocardial administration of an adenovirus vector expressing VEGF121 cDNA to individual with clinical significant severe coronary artery disease".
Kida et al., Nippon Rinsho, 1999, "A new medical treatment for thrombosis by genetic engineering".
Losordo et al., Am Heart J. 1999, "Gene therapy for myocardial angiogenesis".
Isner, Hosp Pract, 1999, "Manipulating angiogenesis against vascular disease".
Kalka et al., Med Klin, 1999, "Vascular endothelial factor (VEGF): therapeutic angiogenesis and vasculogenesis in the treatment of cardiovascular disease".
Safi et al., J. Mol Cell Dardiol, 1997, "Gene therapy with angiogenic factors: a new potential approach to the treatment of ischemic diseases".
Sachiko Kanki-Horimoto., Journal of American Heart Association, 2006, "Implantation of Mesenchymal Stem Cells Overexpressing Endothelial Nitric Oxide Synthase Improves Right Ventricular Impairments Caused by Pulmonary Hypertension".
Yidan D. Zhao, Journal of the American Heart Association, 2005, "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease".
Translation of reference 6 (Bunshikokyubyo, 1999, vol. 3, No. 2, pp. 89-96) "Pulmonary Hypertension".
XP-000915109 (Abstract).
Ziche, Marina et al., Advances in Prostaglandin, Thromboxane and Leukotriene Research, vol. 23, Nitric Oxide Modulates Angiogenesis Elicited by Prostaglandin E1 in Rabbit Cornea.
Ross, Gail et al., Human Gene Therapy 7:1781-1790 (Sep. 10, 1996); Gene Therapy in the United States: A Five-Year Status Report.
Campbell, Andrew I M et al., Circulation, vol. 104, No. 18, (Oct. 30, 2001); Cell-Based Gene Transfer of Vascular Endothelial Growth Factor Attenuates Monocrotaline-Induced Pulmonary Hypertension.
Campbell, Andrew I M et al., American Journal of Respiratory Cell and Molecular Biology, vol. 21, No. 5, Nov. 1999; Cell-Based Gene Transfer to the Pulmonary Vasculature: Endothelial Nitric Oxide Synthase Overexpression Inhibits Monocrotaline-Induced Pulmonary Hypertension.
Campbell, Andrew I M et al., Am. J. Respir. Cell Mol. Biol. vol. 21, pp. 567-575, 1999; Cell-Based Gene Transfer to the Pulmonary Vasculature Endothelial Nitric Oxide Synthase Overexpression Inhibits Monocrotaline-Induced Pulmonary Hypertension.
Tuder, et al., J. Clin. Invest, vol. 95, Apr. 1995, 1798-1807, Increased Gene Expression for VEGF and the VEGF Receptors KDR/FLK and Flt in Lungs Exposed to Acute or to Chronic Hypoxia.
Junker, et al., Blood, vol. 89, No. 12 Jun. 15, 1997: pp. 4299-4306, Hematopoietic Potential and Retroviral Transduction of CD34.
Lyerly, H. Kim, Annals of Surgery, Feb. 1996, vol. 223, Issue 2—Gene Therapy in Surgery.
DT Curiel, et al., Am J. Respir. Cell Mol. Biol., vol. 14, No. 1, Jan. 1996, 1-18, Gene Therapy Approaches for Inherited and Acquired Lung Diseases.
Coonrod, A., et al, Gene Therapy (1997) 4, 1313-1321, On the Mechanism of DNA Transfection: Efficient Gene Transfer Without Viruses.
Watanabe, Yoshifumi et al., Journal of Biochemistry, 1994, vol. 116, No. 6 1220-1226, Highly Efficient Transfection Into Primary Cultured Mouse Hepatocytes by Use of Cation-Liposomes: An Application for Immunization.
Efrat, Shimon, Society of the European Journal of Endocrinology (1998); Cell-Based Therapy for Insulin-Dependent Diabetes Mellitus.
Voelkel, Norbert, F., et al., The Journal of Clinical Investigation, Sep. 2000, vol. 106, No. 6, p. 733-738, Hypdxia-Induced Pulmonary Vascular Remodeling: A Model for What Human Disease?.
Mazurier. F., et al., J. Inherit Metab Dis., Jun. 1997; 20(2):247-257, Gene Transfer of the Uroporphyrinogen III Synthase CDNA Into Haematopoietic Progenitor Cells I Nview of a Future Gene Therapy in Congenital Erythropoietic Porphyria.
Melillo, Guido, 1997, Elseiver Science B.V., Gene Therapy for Collateral Vessel Development.
Tsurumi, Yukio et al., Curculation, 1996, American Heart Association Inc., 94: 3281-3290, Direct Intramuscular Gene Transfer of Naked DNA Encoding Vascular Endothelial Growth Factor Augments Collateral Development and Tissue Perfusion.
Majesky, Mark W., 1996, American Heart Association, 94:3062-3064, A Little VEGF Goes a Long Way . . . .
Van der Zee, Rien, et al., 1997, American Heart Association, 95:1030-1037, Vascular Endothelial Growth Factor/Vascular Permeability Factor Augments Nitric Oxide Release From Quiescent Rabbit and Human Vascular Endothelium.
Falqui, Luca, et al., J. Mol Med (1999) 77:250-253, Human Proinsulin Production in Primary Rat Hepatocytes After Retroviral Vector Gene Transfer.
Janssens, Stefan P. et al., J. Clin. Invest. vol. 98, No. 2, Jul. 1996, 317-324, Adenoviral-Mediated Transfer of the Human Endothelial Nitric Oxide Synthase Gene Reduced Acute Hypdxic Pulmonary Vasoconstriction in Rats.
Lewis, Basil, S., et al., 1997 Elsevier Science B.V., Cardiovascular Research 35 (1997) 490-497, Angiogenesis by Gene Therapy; A New Horizon for Myocardial Revascularization.
Ziche, Marina et al., J. Clinc. Invest, vol. 99, No. 11, Jun. 1997, 2625-2634, Nitric Oxide Synthase Lies Downstream From Vascular Endothelial Growth Factor-Induced But Not Basic Fibroblast Growth Factor-Induced Andiogenesis.
Wei, Yanzhang, et al., Stem Cells, 1995; 13:541-547, Directed Endothelial Differentiation of Cultured Embryonic Yolk Sac Cells In Vivo Provides a Novel Cell-Based System for Gene Therapy.
Dichek, David, A., et al., 1996, American Heart Association, Circulation 1996; 93:301-309, Enhanced In Vivo Antithrombotic Effects of Endothelial Cells Expressing Recombinant Plasminogen Activators Transduced With Retroviral Vectors.
Dunn, Peter, F., et al., 1996, American Heart Association, Circulation, 1996; 93:1439-1446, Seeding of Vascular Grafts With Genetically Modified Endothelial Cells.
Tzeng, Edith, et al., 1996, Molecular Medicine, vol. 2, No. 2, 211-225, Vascular Gene Transfer of the Human Inducible Nitric Oxide Synthase: Characterization of Activity and Effects on Myointimal Hyperplasia.
Valenzuela, David, M., et al., Biochemistry, vol. 96, pp. 1904-1909, Mar. 1999, Angiopoietins 3 and 4: Divergine Gene Counterparts in Mice and Humans.
Rodman, DM, et al., Am. J. Respir, Cell Mol. Biol., vol. 16, No. 6, Jun. 1997, 640-649, In Vivo Gene Delivery to the Pulmonary Circulation in Rats: Transgene Distribution and Vascular Inflammatory Response.
Baxevanis, Andreas D., et al., Interations of Coiled Coils in Transcription Factors: Where in the Specificity?

(56) References Cited

OTHER PUBLICATIONS

Yogalingam, Gouri et al., Evaluation of Fibroblast-Mediated Gene Therapy in a Feline Model of Mucopolysaccharidosis Type VI.
Ware, L.B. et al., The Acute Respiratory Distress Syndrome, The New England Journal of Medicine, May 4, 2000, vol. 342, No. 18, pp. 1334-1349, Massachusetts Medical Society, Waltham, MA, USA.
Gross, C.H. et al., Incidence of Acute Lung Injury in the United States, Crit Care Med, 2003, vol. 31, No. 6, pp. 1607-1611, Lippincott Williams & Wilkins, USA.
Mendez, J. L. et al., New Insights into the Pathology of Acute Respiratory Failure, 2005, Current Opinion in Critical Care, vol. 11, pp. 29-36, Lippincott Williams & Wilkins, USA.
Rubenfeld, G.D. et al., Incidence and Outcomes of Acute Lung Injury, The New England Journal of Medicine, Oct. 20, 2005, vol. 353, No. 16, pp. 1685-1693, Massachusetts Medical Society, Waltham, MA, USA.
Kitamura, Y. et al., Fas/Fasl-Dependent Apoptosis of Alveolar Cells After Lipopolysaccharide-Induced Lung Injury in Mice, American Journal of Respiratory and Critical Care Medicine, Mar. 12, 2000, vol. 163, pp. 762-769, USA.
Matute-Bello, G. et al., Sustained Lipopolysaccharide-Induced Lung Inflammation in Mice is Attenuated by Functional Deficiency of the Fas/Fas Ligand System, Clinical and Diagnostic Laboratory Immunology, Mar. 2004, vol. 11, No. 2, pp. 358-361, American Society for Microbiology, USA.
Rojas, M. et al., Endotoxin-Induced Lung Injury in Mice: Structural, Functional, and Biochemical Responses, The American Journal of Physiology—Lung Cellular and Molecular Physiology, Sep. 7, 2004, vol. 288, pp. L333-L341, American Physiological Society, USA.
Altemeier, W.A. et al., Modulation of Lipopolysaccharide-Induced Gene Transcription and Promotion of Lung Injury by Mechanical Ventilation, The Journal of Immunology, Mar. 28, 2005, vol. 175, p. 3369-3376, The American Association of Immunologists, Inc., USA.
Gharib, S.A. et al., Computational Identification of Key Biological Modules and Transcription Factors in Acute Lung Injury, American Journal of Respiratory and Critical Care Medicine, Sep. 20, 2005, vol. 173, pp. 653-658, USA.
Fan, J. et al., TLR4 Signaling Induces TLR2 Expression in Endothelial Cells Via Neutrophil NADPH Oxidase, The Journal of Clinical Investigation, Apr. 18, 2003, vol. 112, No. 8, pp. 1234-1243, USA.
Zhang; Shijia; et al., Comparison of the therapeutic effects of human and mouse adipose-derived stem cells in a murine model of lipopolysaccharide-induced acute lung injury, Stem Cell Research & Therapy, 2013, pp. 1-13, vol. 4, No. 13, http://stemcellres.com/content/4/1/13.
Bonfield, Tracey L., In Vivo Models of Lung Disease, Lung Diseases—Selected State of the Art Reviews, Dr. Elvisegran Malcolm Irusen Mar. 2012, pp. 407-428, InTech, ISBN: 978-953-51-0180-2.
Rittirsch, Daniel, et al., Acute Lung Injury Induced by Lipopolysaccharide Is Independent of Complement Activation, The Journal of Immunology, 2008, pp. 7664-7672, vol. 180, http://www.jimmunol.org/content/180/11/7664.
Non-Final Office Action dated May 31, 2019, U.S. Appl. No. 15/806,539, "Cell-Based Therapy for the Pulmonar System," filed Nov. 8, 2017.

* cited by examiner

FIG. 10 - hPGIS cDNA gel

FIG. 11 - Cell-based gene transfer using PGIS in experimental pulmonary hypertension (prevention protocol)

FIG. 12 - Cell-based gene transfer using PGIS in experimental pulmonary hypertension (prevention protocol)

FIG. 14 - hVEGF expression by PCR is shown after a single transfection protocol, contrasting the effect of different superfect to DNA ratios on transfection efficiency:

FIG. 15 - β-gal staining comparing a single transfection to a double protocol.

FIG. 16 - Morphology of isolated lung epithelial cells in primary cell culture, 5 days after isolation.

FIG. 17 - Fluorescent microscopy showing purity of isolated lung epithelial cells 25 A
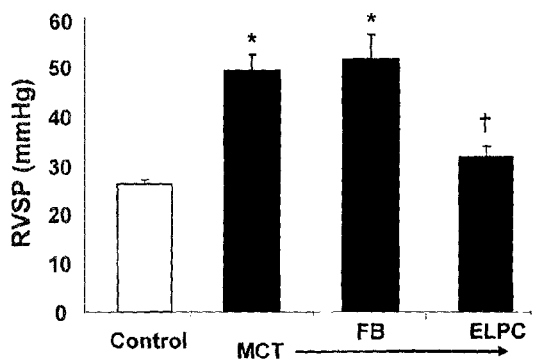
25 B
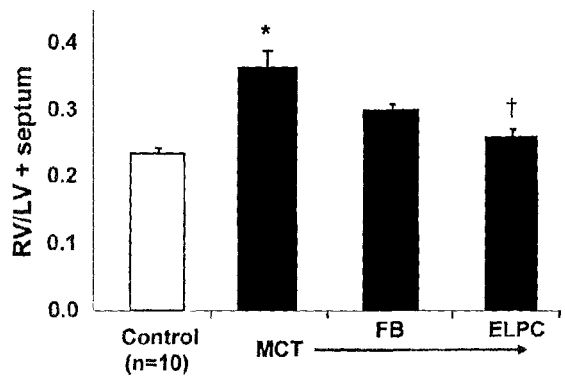
FIG. 25

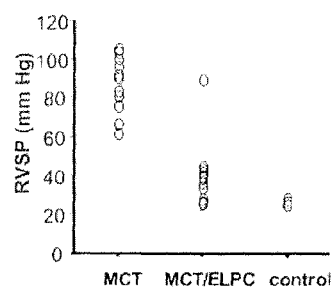
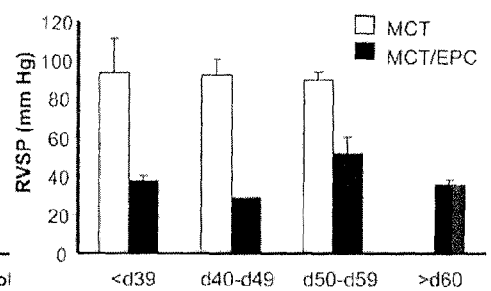
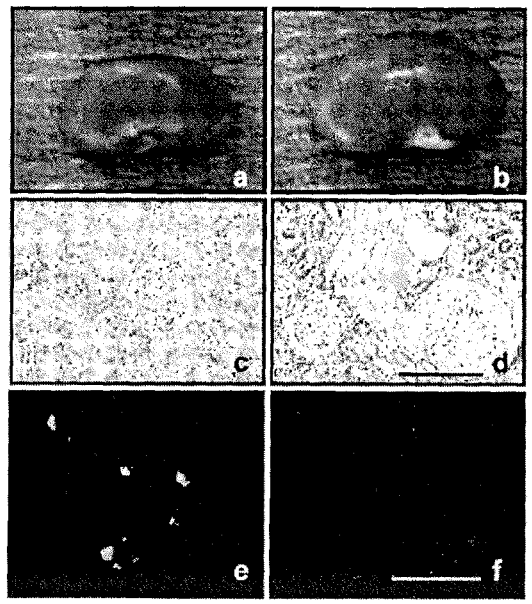
FIG. 26

27 A
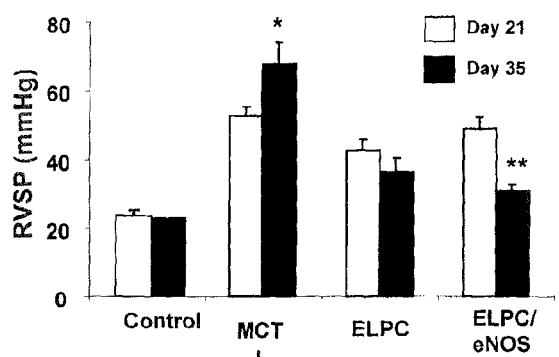
27 B
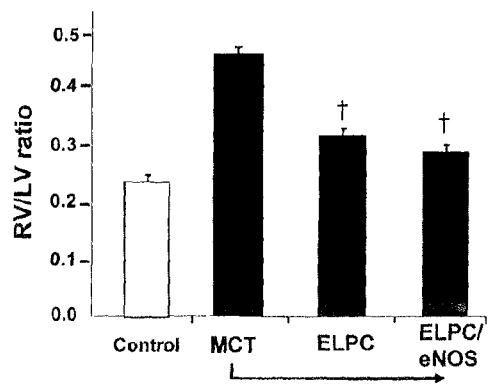
FIG. 27

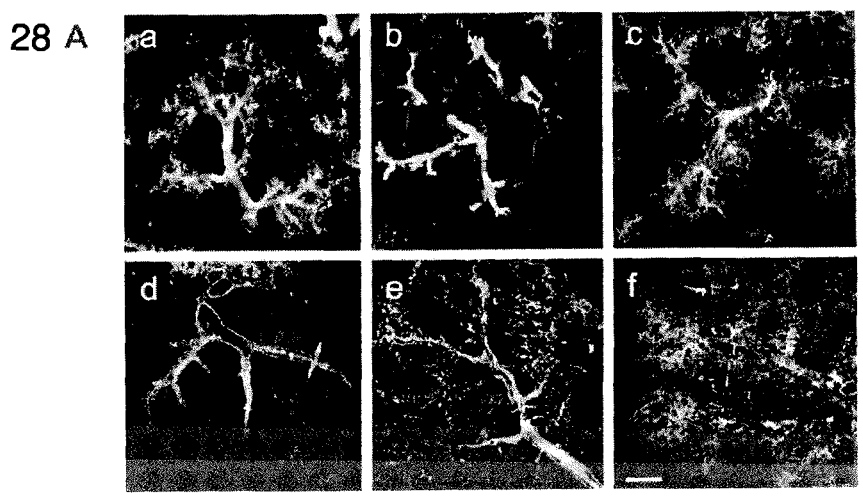
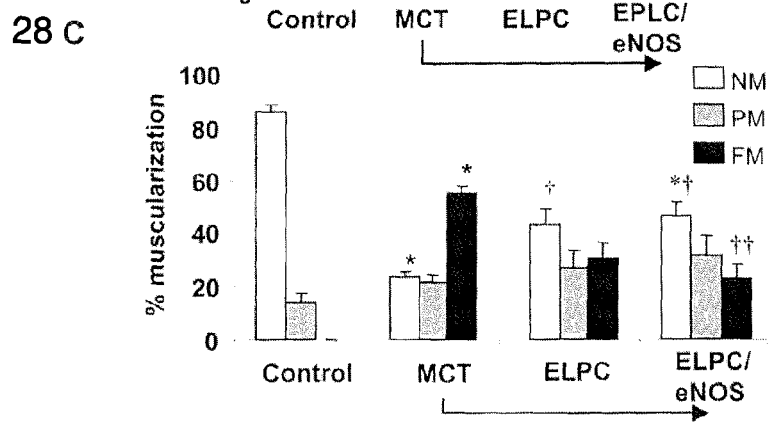
FIG. 28

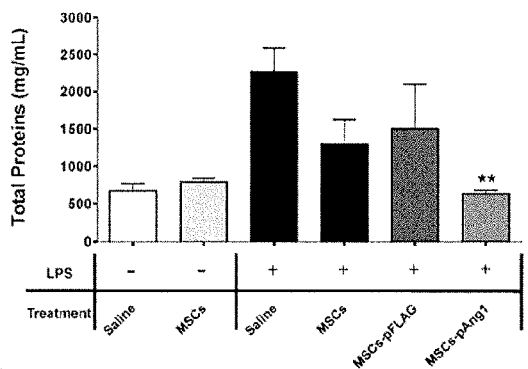
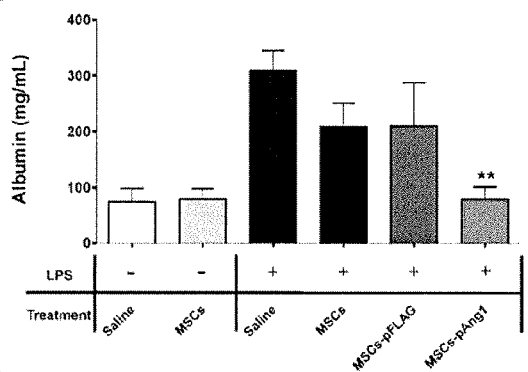
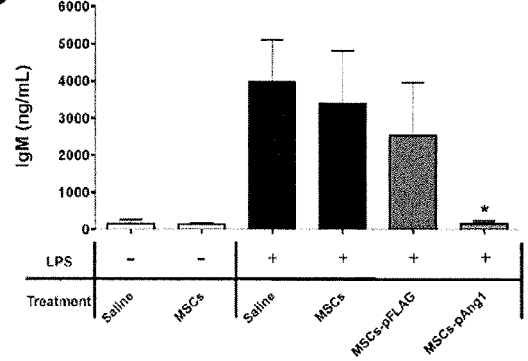
FIG. 33

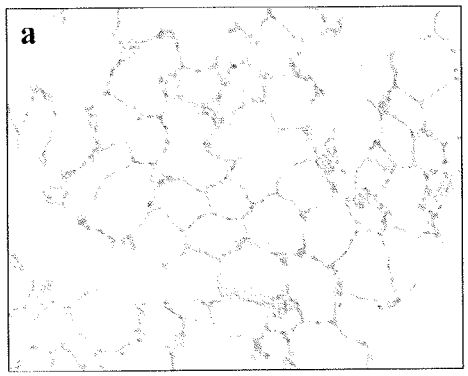
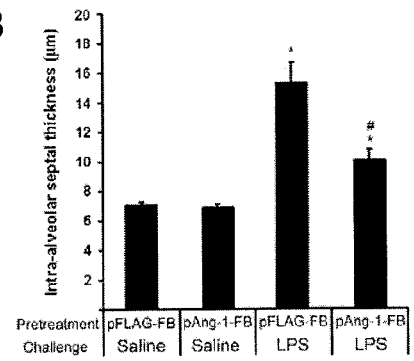
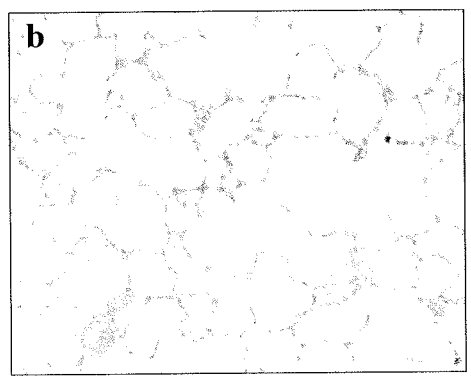
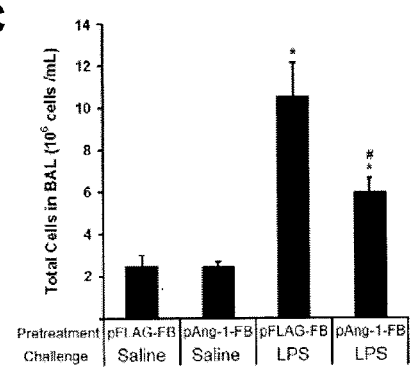
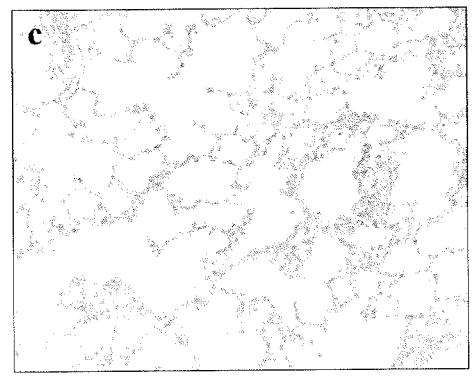
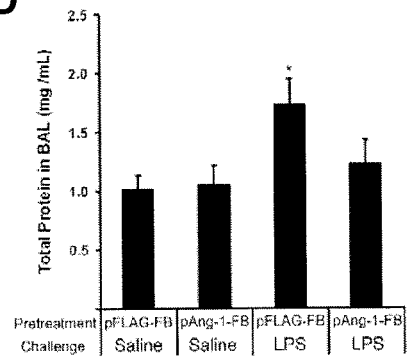
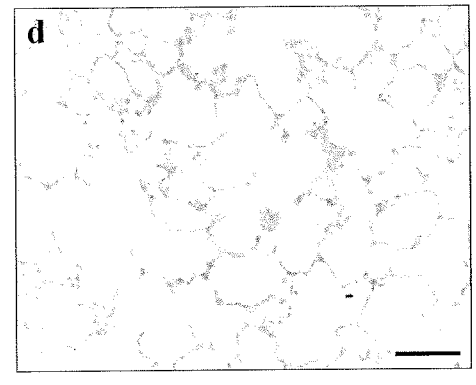
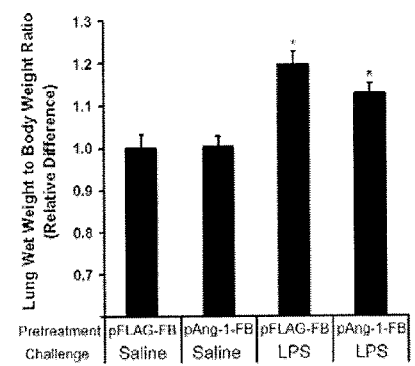
FIG. 36

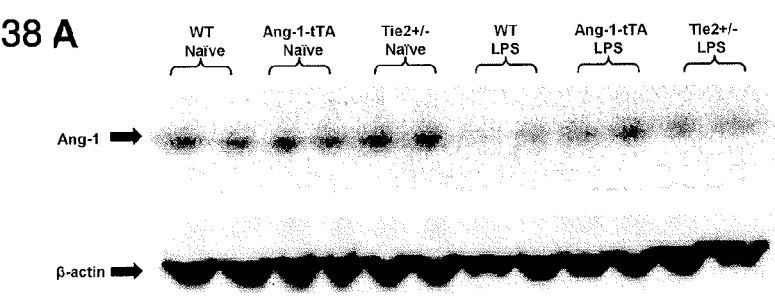
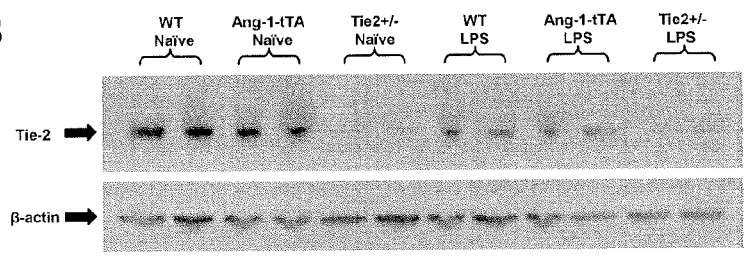
FIG. 38

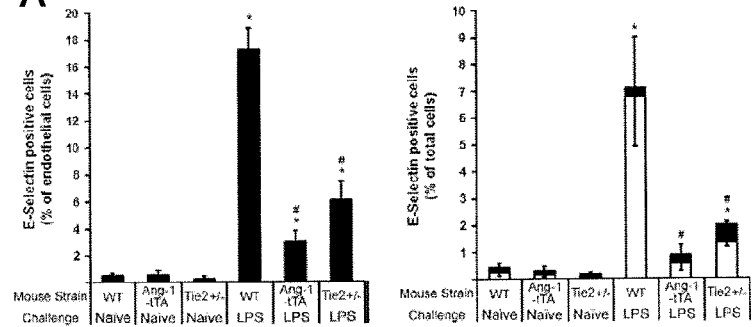
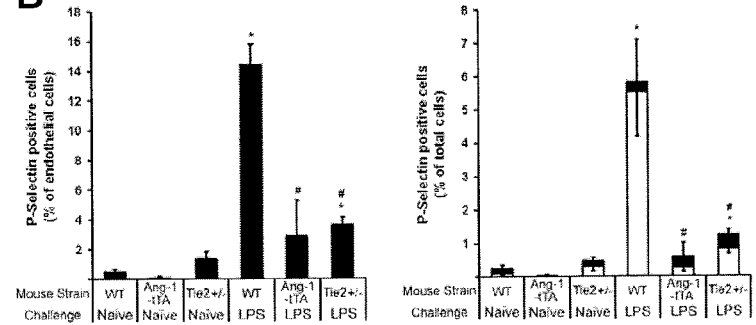
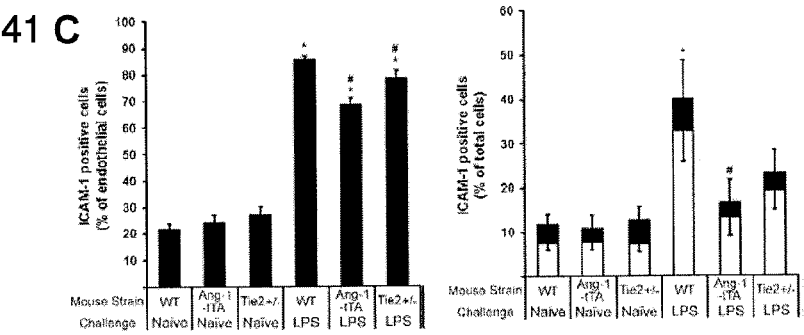
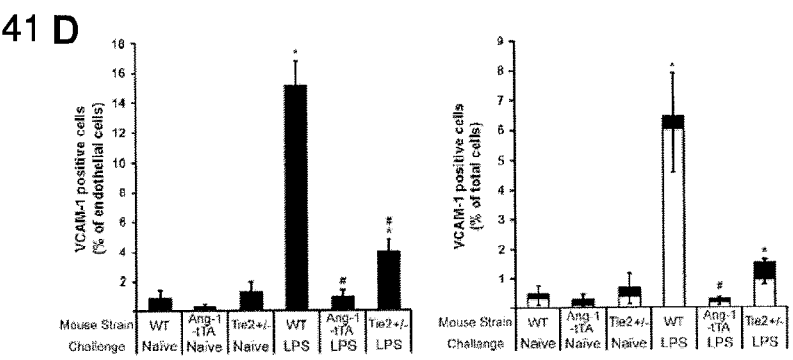
FIG. 41

42 A
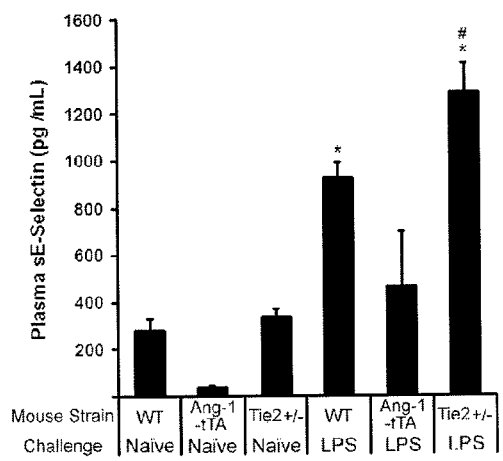
42 B
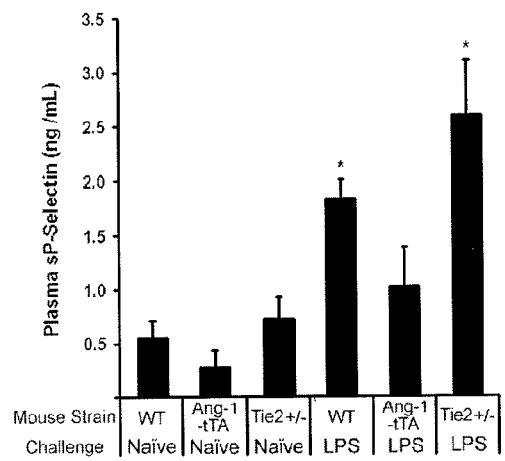
42 C
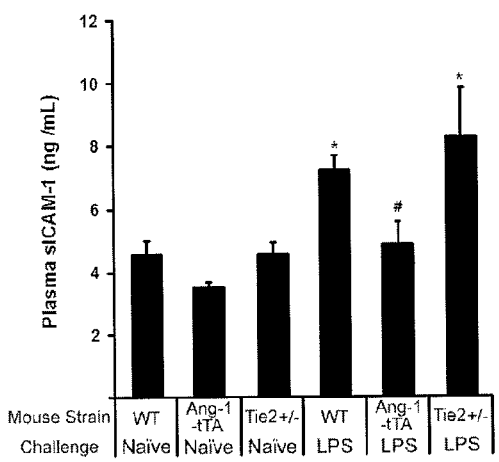
42 D
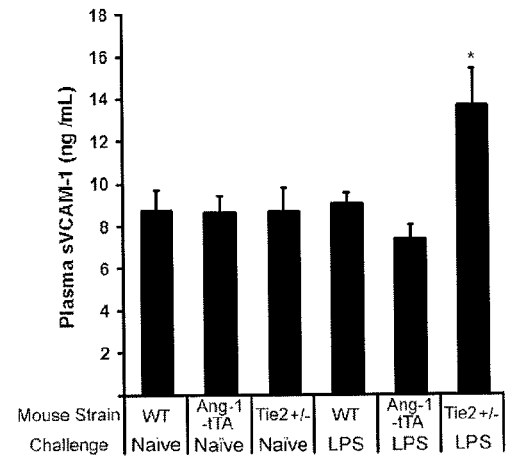
FIG. 42

CELL-BASED THERAPY FOR THE PULMONARY SYSTEM

CROSS-REFERENCE TO RELATED APPLICATION

This application is a continuation-in-part of U.S. patent application Ser. No. 14/303,748, filed Jun. 24, 2014, issued as U.S. Pat. No. 9,827,270, which is a continuation-in-part of U.S. patent application Ser. No. 11/696,039, filed Apr. 3, 2007, issued as U.S. Pat. No. 9,585,916. The entire disclosure of those applications is incorporated herein by reference.

FIELD OF THE INVENTION

This invention relates to medical treatments and composition and procedures useful therein. More specifically, it relates to cell-based therapy delivered to the pulmonary system of a mammalian patient.

BACKGROUND OF THE INVENTION

Cell-based gene transfer is a known, albeit relatively new and experimental, technique for conducting gene therapy on a patient. In this procedure, DNA sequences containing the genes which it is desired to introduce into the patient's body (the transgenes) are prepared extracellularly. e.g. by using enzymatic cleavage and subsequent recombination of DNA with insert DNA sequences. Mammalian cells such as the patient's own (i.e. autologous) or cells from another individual (i.e. allogenic) cells are then cultured in vitro and treated so as to take up the transgene in an expressible form. The transgenes may be foreign to the mammalian cell, additional copies of genes already present in the cell, to increase the amount of expression product of the gene or copies of normal genes which may be defective or missing in a particular patient. Then the cells containing the transgene are introduced into the patient, so that the gene may express the required gene products in the body, for therapeutic purposes. The take-up of the foreign gene by the cells in culture may be accomplished by genetic engineering techniques, e.g. by causing transfection of the cells with a virus containing the DNA of the gene to be transferred by lipofection, by electroporation, or by other accepted means to obtain transfected cells, such as the use of viral vectors. This is sometimes followed by selective culturing of the cells which have successfully taken up the transgene in an expressible form, so that administration of the cells to the patient can be limited to the transfected cells expressing the transgene. In other cases, all of the cells subject to the take-up process are administered.

This procedure has in the past required administration of the cells containing the transgene directly to the body organ requiring treatment with the expression product of the transgene. Thus, transfected cells in an appropriate medium have been directly injected into the liver or into the muscle requiring the treatment, or via the systemic arterial circulation to enter the organ requiring treatment.

Previous attempts to introduce such genetically modified cells into the systemic arterial circulation of a patient have encountered a number of problems. For example, there is difficulty in ensuring a sufficiently high assimilation of the genetically modified cells by the specific organ or body part where the gene expression product is required for best therapeutic benefit. This lack of specificity leads to the administration of excessive amounts of the genetically modified cells, which is not only wasteful and expensive, but also increases risks of side effects. In addition, many of the transplanted genetically modified cells do not survive when administered to the systemic arterial circulation, since they encounter relatively high arterial pressures. Infusion of particulate materials, including cells, to other systemic circulations such as the brain and the heart, may lead to adverse consequences due to embolization, i.e. ischemia and even infarction.

The acute respiratory distress syndrome (ARDS), the clinical correlate of severe acute lung injury (All) in humans, is an important cause of morbidity and mortality in critically ill patients (Ware, L. B., and M. A Matthay, 2000. N Engl J Med 342:1334-1349. Goss, C. H. et al. 2003. Crit Care Med 31: 1607-1611. Mendez, J. L. and RD. Hubmayr, 2005. Curr Opin Crit Care 11:29-36. Rubenfeld, G. D. et al 2005. N Engl J Med 353:1685-1693.). Infectious etiologies, such as sepsis and pneumonia (including influenza and SARS), are leading causes of ALI/ARDS (Ware, L. B., and M. A Matthay, 2000. Goss, C. H. et al. 2003). Histologically, ALI/ARDS in humans is characterized by a severe acute inflammatory response in the lungs and neutrophilic alveolitis (Ware. L. B., and M. A Matthay, 2000.). Inflammatory stimuli from microbial pathogens, such as endotoxin (lipopolysaccharide, LPS), are well recognized for their ability to induce pulmonary inflammation, and experimental administration of LPS, both systemically and intratracheally, has been used to induce pulmonary inflammation in animal models of ALI (Kitamura. Y, S. et al. 2001. Am J Respir Crit Care Med 163:762-769. Matute-Bello, G. et al. 2004. Clin Diagn Lab Immunol 11:358-361. Rojas, M. et al. 2005. Am J Physiol Lung Cell Mol Physiol 288: L333-341. Altemeier, W. A. et al. 2005. J Immunol 175:3369-3376. Gharib, S. A, et al. 2006. Am J Respir Crit Care Med 173:653-658).

The physiological hallmark of ARDS is disruption of the alveolar-capillary membrane barrier (i.e., pulmonary vascular leak), leading to development of non-cardiogenic pulmonary edema in which a proteinaceous exudate floods the alveolar spaces, impairs gas exchange, and precipitates respiratory failure (Ware, L. B., and M. A Matthay, 2000. Ware, L. B., and M. A Matthay, 2001. Am J Respir Crit. Care Med 163: 1376-1383. Guidot, D. M. et al. 2006. Am J Physiol Lung Cell Mol Physiol 291:L301-306.). Both alveolar epithelial and endothelial cell injury and/or death have been implicated in the pathogenesis of ALI/ARDS (Ware, L. B., and M. A Matthay, 2000). However, despite decades of research, few therapeutic strategies for clinical ARDS have emerged and current specific options for treatment are limited (Crimi, E., and A S. Slutsky, 2004. Best Pract Res Clin Anaesthesiol 18:477-492. The Acute Respiratory Distress Syndrome Network, 2000. N Engl J Med 342: 1301-1308. Matthay. M. A, et al. 2003. Am J Respir Crit Care Med 167: 1027-1035. Mehta, D. J. Bhattacharya. M. A Matthay, and A B. Malik, 2004. Am J Physiol Lung Cell Mol Physiol 287:L1081-1090. Slutsky, A S., and L. D. Hudson, 2006. N Engl J Med 354: 1839-1841). ARDS continues to be an important contributor to prolonged mechanical ventilation in the intensive care unit (ICU), and ARDS-associated mortality remains high at 30-50% despite optimal ICU supportive care (Ware. L. B., and M. A Matthay, 2000. The Acute Respiratory Distress Syndrome Network, 2000. Matthay, M. A. et al. 2003. Slutsky, A. S. and L. D. Hudson, 2006).

ARDS is a complex clinical syndrome which is initiated by injury to the lung, often in the setting of pneumonia and/or sepsis, and aggravated by ventilator-induced injury. Some of the early feature of ARDS can be reproduced by administration of bacterial endotoxin (LPS), which acts via Toll-like receptor 4 (TLR4), to increase the expression of inflammatory cytokines and chemokines, and upregulate leukocyte adhesion molecules, results in EC activation (Kitamura, Y, S. et al. 2001. Matute-Bello. G. et al. 2004. Rojas, M. et al. 2005. Altemeier. W. A. et al. 2005. Gharib. S. A, et al. 2006. Fan, J, et al. J Clin Invest 112: 1234-1243).

It is an object of the present invention to provide a novel procedure of cell based therapy or cell-based gene transfer to mammals, for the treatment of lung diseases or disorders.

It is a further and more specific object of the invention to provide novel procedures of cell-based gene therapy utilizing dermal (or other) fibroblast cells, EPCs, or MSCs, for treatment of lung diseases or disorders.

It is a further object of the invention to provide novel genetically engineered cells containing transgenes expressing angiogenic factors for treatment of lung diseases or disorders.

It is a further and more specific object of the invention to provide novel uses and novel means of administration of angiogenic factors in human patients for treatment of lung diseases or disorders.

It is a further object of the invention to treat or prevent pulmonary hypertension utilizing novel therapies, including cell therapy and cell-based gene therapy.

It is a further object of the present invention to treat or prevent Acute Respiratory Distress Syndrome (ARDS) utilizing novel therapies, including cell therapy and cell-based gene therapy.

SUMMARY OF THE INVENTION

The present invention is based upon the discovery that the pulmonary system of a mammal, including a human, offers a potentially attractive means of introducing genetically altered cells or regenerative cells into the body, for purposes of gene therapy, i.e. cell based gene transfer, or for pulmonary regeneration cell therapy. The pulmonary system has a number of unique features rendering it particularly suited to a cell-based gene transfer. Thus, low arterial pressure and high surface area with relatively low shear in the microcirculation of the lungs increase the chances of survival of the transplanted cells. High oxygenation in the micro-circulation of the ventilated lung also improves the viability of the transplanted cells.

Moreover, the pulmonary circulation functions as a natural filter, and is able to retain the infused cells efficiently and effectively. Also, the lung has a dual circulation (pulmonary arterial and bronchial). This is in contra-distinction to other systemic circulations, such as the brain and the heart, where the infusion of particulate materials such as cells could lead to the aforementioned adverse consequences. The lung presents a massive vascular system. The high surface area of the pulmonary endothelium allows the migration of the transplanted cells trapped in the micro-circulation across the endothelial layer to take up residence within the perivascular space.

The pulmonary circulation, unlike any other circulation in the body, receives the entire output of the heart. Accordingly, it offers the greatest opportunity to release a gene product into the circulation. This distinct property of the lung is particularly useful for pulmonary gene therapy and for the treatment of a systemic disorders, as well as a pulmonary disorder.

It is believed that the cells become lodged in the small artery-capillary transition regions of the pulmonary circulation system, following simple intravenous injection of the transfected or regenerative cells to the patient. Products administered intravenously move with the venous circulation to the right side of the heart and then to the lungs. The cells administered according to the invention appear to lodge in the small arteriolar-capillary transition regions of the circulatory system of the lungs, and then transmigrate from the intraluminal to the perivascular space. From there transfected cells can deliver expression products of the transgenes to the lungs, making the process to the present invention especially applicable to treatment of pulmonary disorders. Some factors, especially stable factors can be secreted to the general circulation for treatment of disorders of other body organs.

Certain cells may have therapeutic potential in their own right, such as bone marrow derived (mesenchymal) stem (stromal) cells (MSCs) or other cells with regenerative potential (e.g. endothelial progenitor cells or endothelial-like progenitor cells, adipose tissue derived mesenchymal stem cells, multipotent adult progenitor cells (MAPCs), side population (SP) cells, lung derived progenitor or stem cells, or embryonic stems cells (ESCs), among others) in which case administration of such cells even without the benefit of gene transfection may result in therapeutic effects.

Thus, according to a first aspect of the present invention, there is provided a process of conducting gene therapy in a mammalian patient, which comprises administering to the pulmonary system of the patient, genetically modified mammalian cells containing at least one expressible transgene which is capable of producing at least one gene product in the pulmonary circulation after administration thereto.

According to another, more specific aspect of the invention, there are provided genetically modified mammalian cells selected from fibroblasts, endothelial cells, smooth muscle cells, endothelial progenitor cells, endothelial-like progenitor cells, and mesenchymal stem cells, said cells containing at least one expressible transgene coding for a therapeutic factor.

A further aspect of the present invention provides the use in the preparation of a medicament for administration to a mammalian patient to alleviate symptoms of a disorder, of viable, transfected mammalian cells containing at least one expressible transgene coding for a therapeutic factor.

Yet another aspect of the present invention is a process of preparing genetic modifications of mammalian cells selected from fibroblasts, endothelial cells and progenitor cells, which comprises transfecting said mammalian cells with at least one gene coding for a therapeutic factor, to produce transfected cells capable of expressing said therapeutic factor in vivo.

An additional aspect of the present invention is the treatment of pulmonary hypertension (PH). Primary pulmonary hypertension (PPH), now referred to as idiopathic PAH (IPAH), and other causes of PH are associated with severe abnormalities in endothelial function, which likely play a critical role in its pathogenesis. The vasodilatory, anti-thrombotic and anti-proliferative factor, nitric oxide (NO) has been demonstrated to decrease pulmonary pressures in both experimental and clinical situations. However, long-term viral-based methods may cause significant local inflammation. Other, previous attempts to treat PPH have involved the use of prostacyclin, using continuous administration, but this is a difficult and expensive procedure, liable to give rise to side effects. Newer oral, inhaled or subcutaneously administered treatments have been recently introduced, but, again, these have limited efficacy and/or significant side effects which limit their use.

The present invention provides, from this additional aspect, a method of alleviating the symptoms of IPAH (and other causes of PH) which comprises administering to the pulmonary system of a patient suffering therefrom, at least one angiogenic factor, or a precursor or genetic product capable of producing and releasing into the pulmonary circulation at least one angiogenic factor. The method would be applicable to all "Group 1" WHO PAH including PAH associated with scleroderma, congenital heart disease, lupus (SLE), etc.

An embodiment of this additional aspect of the present invention is the delivery to a patient suffering from PPH of genetically modified cells containing a gene capable of expressing in vivo at least one angiogenic factor, by a process of cell-based gene transfer as described above. This additional aspect of invention, however, is not limited to any specific form of administration, but pertains generally to the use of angiogenic factors and precursors thereof which produce angiogenic factors in situ, in treating or alleviating the symptoms of PPH, delivered to the pulmonary circulation by any suitable means.

The invention provides a process of alleviating or inhibiting a disorder in a mammalian patient by conducting therapy which comprises administration to the lung by injection into the blood system of the mammalian patient suffering from a disorder, of viable mammalian cells effective for alleviating or inhibiting the disorder.

The mammalian cells may contain at least one expressed transgene, the transgene expressing a composition effective for alleviating or inhibiting the disorder.

In an embodiment, the disorder is a breathing disorder. Breathing disorders may be due to disorders of the lung or airways. In an embodiment, the transfected cells contain a transgene coding for Prostaglandin 1 Synthase (PGIS). The breathing disorder may be ARDS. The transfected cells may contain a transgene coding for Ang-1. The disorder may be cystic fibrosis. The transfected cells may contain a transgene coding for CFTR.

One aspect of the present invention is the treatment or prevention of ARDS through the administration of MSC cells. The MSC cells may be transfected or otherwise transformed to express Ang-1.

The invention further teaches genetically modified, viable cells genetically modified to contain an expressible transgene coding for PGIS. The cells may be fibroblasts. The cells may be for use in the treatment of pulmonary hypertension. The cells may be for use in the treatment of PPH.

The invention further teaches genetically modified, viable cells genetically modified to contain an expressible transgene coding for CFTR. The cells may be epithelial progenitor cells. The cells may be for use in the treatment of cystic fibrosis.

The invention further teaches a process of preparing transformants of mammalian cells, which comprises transfecting said mammalian cells with at least one gene coding for a factor selected from the group consisting of CFTR, PGIS, Ang-1, vascular endothelial growth factor family (VEGF A, B, C, PlGF), fibroblast growth factor, erythropoietin, hemoxygenase-1 (HO-1) or hemoxygenase-2 (HO-2), transforming growth factor beta (or other member of the TGF-beta super family including BMPs 1, 2, 4, 7 and their receptors BMPR2 or BMPR1) and platelet derived growth factors (A or B), to produce transformed cells capable of expressing said factor in vivo. The mammalian cells may be selected from the group consisting of endothelial cells, smooth muscle cells, progenitor cells such as endothelial progenitor cells (e.g. from bone marrow or peripheral blood), dermal fibroblasts, stem cells, mesenchymal stem cells, marrow stromal cells (MSC), epithelial cells, epithelial progenitor cells, and others.

The invention further teaches a process of alleviating or inhibiting a disorder in a mammalian patient by conducting therapy which comprises administration to the lung by injection into the blood system of the mammalian patient suffering from a disorder, of viable mammalian cells, wherein the mammalian cells are effective for tissue regeneration. The disorder may be a lung degenerative disorder. In embodiments of the invention, the mammalian cells are selected from the group consisting of progenitor cells such as endothelial progenitor cells (e.g. from bone marrow or peripheral blood), stem cells, mesenchymal stem cells, marrow stromal cells (MSC), epithelial cells and epithelial progenitor cells. The disorder may be pulmonary hypertension, chronic obstructive pulmonary disease, lung injury/ARDS, and pulmonary fibrosis.

In another embodiment, the invention teaches a process of alleviating or inhibiting pulmonary hypertension in a mammalian patient by conducting therapy which comprises administration to the mammalian patient an angiogenic factor or a gene which expresses an angiogenic factor. The angiogenic factor may be selected from the group consisting of vascular endothelial growth factor (VEGF) and its isoforms, fibroblast growth factor (FGF, acid and basic), angiopoietin-1 and other angiopoietins, erythropoietin, hemoxygenase, transforming growth factor-α (TGF-α), transforming growth factor-β (TGF-β) or other members of the TGF-β super family including BMPs 1, 2, 4, 7 and their receptors MBPR2 or MBPR1, hepatic growth factor (scatter factor), and hypoxia inducible factor (HIF).

In one embodiment, the invention teaches a process of alleviating or inhibiting the progression of pulmonary hypertension in a mammalian patient comprising administration to the lung by injection into the pulmonary circulation of the mammalian patient suffering from the disorder, of fibroblast cells; said cells having been transformed in vitro to express a transgene selected from the group consisting of: vascular endothelial growth factor, fibroblast growth factor, angiopoietin, hemoxygenase, transforming growth factor, hepatic growth factor, endothelial nitric oxide synthase, prostaglandin 1 synthase, Krupple-like factors (KLF-2, 4, and others) artificially engineered transcription factors providing the desired effects, and hypoxia inducible factor; and wherein said cells are further capable of lodging in the small arteriolar-capillary transition regions of the circulatory system within the lungs, wherein the administration results in alleviation or inhibition of progression of the pulmonary hypertension.

In another embodiment, the invention teaches a process for alleviating or inhibiting the progression of pulmonary hypertension in a mammalian patient comprising administration to the lung by injection into the pulmonary circulation of the mammalian patient suffering from the disorder, of smooth muscle cells, said cells having been transformed in vitro to express a transgene selected from the group consisting of: vascular endothelial growth factor and endothelial nitric oxide synthase; and wherein said cells are further capable of lodging in the small arteriolar-capillary transition regions of the circulatory system within the lungs, wherein the administration results in alleviation or inhibition of progression of the pulmonary hypertension.

In yet another embodiment, the present invention teaches a process for alleviating or inhibiting the progression of pulmonary hypertension in a mammalian patient comprising administration to the lung by injection into the pulmonary circulation of the mammalian patient suffering from the disorder, of cells selected from the group consisting of endothelial progenitor cells and endothelial like progenitor cells. In one embodiment, the cells may be allogenic. In another embodiment, the cells may be syngeneic. In another embodiment, the cells may be autologous. In a further embodiment, the cells may be transformed in vitro to express a transgene, for example, an endothelial nitric oxide synthase. The endothelial nitric oxide synthase may be human endothelial nitric oxide synthase. The transformation may be through any known means; in one embodiment, the transformation is through electroporation with eNOS cloned into a plasmid vector. In one embodiment, the pulmonary hypertension is associated with scleroderma. In another embodiment, the pulmonary hypertension is associated with congenital heart disease. In another embodiment, the pulmonary hypertension is associated with lupus (SLE). In another embodiment, the pulmonary hypertension is associated or caused by idiopathic PAH.

In yet an other embodiment, the present invention teaches a process for alleviating or inhibiting the progression of Acute Respiratory Distress Syndrome (ARDS) in a mammalian patient comprising administration to the lung by injection into the pulmonary circulation of the mammalian patient suffering from the disorder, of mesenchymal stem cells. In one embodiment, the cells are allogenic. In another embodiment, the cells are autologous. In a further embodiment, the cells have been transformed in vitro to express a transgene. In one embodiment, the transgene is angiopoietin-1. The transformation may be through any known means; in one embodiment, the transformation is through electroporation with angiopoietin-1 cloned into a plasmid vector.

In another embodiment, the present invention teaches a process of alleviating or inhibiting the progression of an acute respiratory distress syndrome (ARDS) in a mammalian patient comprising administering to the lung by injection into the pulmonary circulation of the patient of cells selected from the group consisting of smooth muscle cells, mesenchymal stem cells and fibroblast cells, said cells having been transformed in vitro to express Angiopoietin-1, wherein the administration results in alleviation or inhibition of the progression of the ARDS. In one embodiment, the fibroblast cells are skin fibroblasts. In one embodiment, the cells are allogenic. In one embodiment, the cells are syngenic. In one embodiment, the cells are autologous. The transformation may be through any known means; in one embodiment, the transformation is through electroporation with angiopoietin-1 cloned into a plasmid vector.

In a further embodiment, the invention teaches a process of alleviating a state selected from the group consisting of lung inflammation, septal edema, alveolar inflammation, and endothelial inflammation, in a mammalian patient, comprising administering to the lung by injection into the pulmonary circulation of the patient of cells selected from the group consisting of smooth muscle cells, mesenchymal stem cells, and fibroblast cells, said cells having been transformed in vitro to express Angiopoietin-1, wherein the administration results in alleviation of the state. The state may be, for example, the result of or caused by acute lung injury. For example, the state may be associated with acute respiratory distress syndrome.

In a further embodiment, the invention teaches a process of alleviating or inhibiting the progression of pulmonary hypertension in a mammalian patient comprising administration to the lung of a transgene selected from the group consisting of: vascular endothelial growth factor, fibroblast growth factor, angiopoeitin, hemoxygenase, transforming growth factor, hepatic growth factor, endothelial nitric oxide synthase, Angiopoietin-1, prostaglandin I synthase (PGIS) and hypoxia inducible factor; wherein the administration results in alleviation or inhibition of progression of the pulmonary hypertension. In one embodiment, the transgene is endothelial nitric oxide synthase. In another embodiment, the transgene is vascular endothelial growth factor. In another embodiment, the transgene is PGIS. In another embodiment, the transgene is Angiopoietin-1. In another embodiment, the pulmonary hypertension is associated with or caused by scleroderma, congenital heart disease, lupus (SLE) or idiopathic PAH.

In a further embodiment, the invention teaches a process for alleviating or inhibiting the progression of Acute Respiratory Distress Syndrome (ARDS) in a mammalian patient comprising administration to the lung of a transgene selected from the group consisting of Angiopoietin-1 and vascular endothelial growth factor.

In a further embodiment/the invention teaches a process of alleviating a state selected from the group consisting of lung inflammation/septal edema/alveolar inflammation/and endothelial inflammation/in a mammalian patient/comprising administering to the lung a transgene selected from the group consisting of Angiopoietin-1 and vascular endothelial growth factor. In one aspect/the state is a result of, or caused by, acute lung injury. In another aspect/the state is associated with acute respiratory distress syndrome.

DESCRIPTION OF THE PREFERRED EMBODIMENTS

A wide variety of transgenes encoding therapeutic factors can be used in the processes and products of the present invention. While treatment of pulmonary system disorders is a primary focus of the invention, it is not limited to such treatments. Therapeutic factors expressed in the lung by the transgenes released into and delivered by the circulation of other body organs downstream of the lungs are within the scope of this invention. Transgenes expressing therapeutic factors such as Factor VIII for treatment of classical haemophelia, and other clotting factors for treating various bleeding disorders may be used. Other examples include:

transgenes expressing hormones, for example growth hormone for treatment of hypopituitary dysfunction, insulin, (thyroid stimulating hormone (TSH) for treatment hypothyroidism following pituitary failure, and other hormones;

transgenes expressing beneficial lipoproteins such as Apo A1 and other proteins/enzymes participating in lipid metabolism such as lipoprotein lipase;

transgenes expressing prostacyclin synthase or other transgenes that produce vasoactive substances;

transgenes expressing anti-oxidants and free radical scavengers;

transgenes expressing soluble cytokine receptors to neutralize actions of damaging levels of immune mediators, for example soluble TNFγ receptor, or cytokine receptor antagonists, for example IL1ra;

transgenes expressing soluble adhesion molecules, for example ICAM-1, to interrupt pathological cell adhesion processes such as those which occur in inflammatory diseases;

transgenes expressing soluble receptors for viruses to inhibit infection of cells, e.g. CD4. CXCR4, CCR5 for HIV;

transgenes expressing cytokines, for example IL-2, to activate immune responses for combating infections; the cystic fibrosis gene, as a transgene.

Other examples of transgenes for use in the cell based therapy of the invention include transgenes encoding for:

elastase inhibitors for use in treating pulmonary vascular disease such as pulmonary hypertension or systemic vascular disease;

tissue inhibiting metalloproteins for use in treating atherosclerosis or arterial aneurysms potassium channels or potassium channel modulators for use in treating pulmonary hypertension anti-oxidants such as superoxide dismutase for use in treating pulmonary hypertension, ARDS and pulmonary fibrosis anti-inflammatory factors such as cytokines, IL-10 and IL-4 for use in treating inflammatory vascular disease such as atherosclerosis or arterial aneurysms The transfected cells lodged in the lung and containing transgenes expressing such factors and other products will act as a systemic source of the appropriate factor.

In some instances, certain cell types, on their own, for example Endothelial Progenitor Cells. Mesenchymal Stem Cells, or Endothelial Progenitor-like Cells, can be therapeutic absent genetic modification to overexpress, or express, these transgenes.

One preferred aspect of the present invention is the treatment of pulmonary hypertension (PH). Primary pulmonary hypertension (PPH) and other causes of PH are associated with severe abnormalities in endothelial function, which likely play a critical role in its pathogenesis. The vasodilatory, anti-thrombotic and anti-proliferative factor, nitric oxide (NO) has been demonstrated to decrease pulmonary pressures in both experimental and clinical situations. However, long-term viral-based methods may cause significant local inflammation. Other, previous attempts to treat PPH have involved the use of prostacyclin, using continuous administration, but this is a difficult and expensive procedure, liable to give rise to side effects.

The present invention provides, from this second preferred aspect, a method of alleviating the symptoms of PPH (and other causes of PH) which comprises administering to the pulmonary system of a patient suffering therefrom transformed mammalian fibroblast cells from dermal or other origins, endothelial cells or progenitor cells, i.e. Endothelial Progenitor Cells, or Endothelial Progenitor-like Cells derived from bone marrow or isolated from the systemic circulation, said transfected cells including at least one expressible transgene coding for an angiogenic factor for release thereof into the pulmonary circulation.

Specific examples of useful angiogenic factors for delivery by way of transgenes in cells, or by way of other routes of the additional aspect of this invention include vascular endothelial growth factor (VEGF) in all of its various known forms, i.e. VEGF165 which is the commonest and is preferred for use herein. VEGF205. VEGF189, VEGF121, VEGFB and VEGFC (collectively referred to herein as VEGF); fibroblast growth factor (FGF, acid and basic), angiopoietin-1 and other angiopoietins, transforming growth factor-a (TGF-a), transforming growth factor-β (TGF-β) or other members of the TGF-β super family, including BMPs 1, 2, 4, 7 and their receptors BMPR2 or BMPR1, and hepatic growth factor (scatter factor) and hypoxia inducible factor (HIF). VEGF is the preferred angiogenic factor, on account of the greater experience with this factor and its level of effective expression in practice. Specific examples of useful vasoactive factors for delivery by way of transgenes in cells, or by way of other routes of the additional aspect of this invention include nitric oxide synthase (NOS), endothelial nitric oxide synthase (eNOS). PGIS, and hemoxygenase. DNA sequences constituting the genes for these factors are known, and they can be prepared by the standard methods of recombinant DNA technologies (for example enzymatic cleavage and recombination of DNA), and introduced into mammalian cells, in expressible form, by standard genetic engineering techniques such as those mentioned above (viral transfection, electroporation, lipofection, use of polycationic proteins, etc).

In an additional aspect of the invention, angiogenic factors can be administered directly to the patient, e.g. by direct infusion of the factor, into the vasculature. They can also be administered to the patient by processes of inhalation, whereby a replication-deficient recombinant virus coding for the angiogenic factor is introduced into the patient by inhalation in aerosol form, or by intravenous or arterial injection of the DNA constituting the gene for the factor itself (although this is inefficient). Such administration methods, including injection or inhalation, can also be used for cells transfected with the angiogenic factors. Administration methods as used in known treatments of cystic fibrosis can be adopted.

Angiogenic factors such as those mentioned above have previously been proposed for use as therapeutic substances in treatment of vascular disease. It is not to be predicted from this work, however, that such angiogenic factors would also be useful in treatment of pulmonary hypertension. Whilst it is not intended that the scope of the present invention should be limited to any particular theory or mode of operation, it appears that angiogenic growth factors may also have properties in addition to their ability to induce new blood vessel formation. These other properties apparently include the ability to increase nitric oxide production and activity, and/or decrease the production of endothelin-1, in the pulmonary circulation, so as to improve the balance of pulmonary cell nitric oxide in endothelin-1 production.

In preparing cells for transfection and subsequent introduction into a patient's pulmonary system, it is preferred to start with somatic mammalian cells obtained from the eventual recipient (i.e. autologous cells) of the cell-based gene transfer treatment of then present invention, however, it is also possible that in other instances there may be advantages to using cells derived from another individual (i.e. allogenic cells). A wide variety of different cell types may be used, including fibroblasts, endothelial cells, smooth muscle cells, progenitor cells (e.g. from bone marrow or peripheral blood), fibroblasts, such as dermal fibroblasts, endothelial progenitor cells (EPCs), endothelial-like progenitor cells (ELPC's), mesenchymal cells, marrow stromal cells (MSC), and epithelial cells, and others. Dermal fibroblasts are simply and readily obtained from the patient's exterior skin layers, readied for in vitro culturing by standard techniques. Endothelial cells are harvested from the eventual recipient. e.g. by removal of a saphenous vein and culture of the endothelial cells. Progenitor cells can be obtained from bone marrow biopsies or aspiration, or isolated from the circulating blood, and cultured in vitro. The culture methods are standard culture techniques with special precautions for culturing of human cells with the intent of re-implantation. With certain cell types, such as MSCs. EPCs or ELPCs, the cells alone have efficacious properties without transfection, and may be used either alone, or, for synergistic effect, transfected or otherwise expressing an angiogenic factor as described above. The EPCs MSCs or ELPCs may be autologous, syngenic, or even allogenic.

One embodiment of the present invention uses dermal fibroblasts from the patient as the cells for gene transfer. Given the fact that the logical choice of cell types for one skilled in the art to make would be a cell type naturally found in the patient's pulmonary system, such as smooth muscle cells, the use of fibroblasts is counter-intuitive. Surprisingly, it has been found that fibroblasts are eminently suitable for this work, exhibiting significant and unexpected advantages over cells such as smooth muscle cells. They turn out to be easier to grow in culture, and easier to transfect with a transgene, given the appropriate selection of technique. They yield a higher proportion of transfectants, and a higher degree of expression of the angiogenic factors in vivo, after introduction into the patient's pulmonary system. The anticipated greater risk with fibroblasts of possibly causing fibrosis in the pulmonary system, as compared with smooth muscle cells, has not materialized.

The somatic gene transfer in vitro to the recipient cells, i.e. the genetic engineering, is performed by standard and commercially available approaches to achieve gene transfer, as outlined above. Preferably, the method includes the use of poly cationic proteins (e.g. SUPERFECT™) or lipofection (e.g. by use of GENEFECTOR™), agents available commercially and which enhance gene transfer. However, other methods besides lipofection and polycationic protein use, such as, electroporation, viral methods of gene transfer including adeno and retro viruses, may be employed. These methods and techniques are well known to those skilled in the art, and are readily adapted for use in the process of the present invention. Lipofection is a commonly used technique, for use with dermal fibroblast host cells, whereas the use of polycationic proteins is preferred for use with smooth muscle cells. Electroporation can also be used as it is more easily applied in the context of human therapy. Different methods can be selected based on whether transient or more permanent expression of the transgene is desired.

The re-introduction of the genetically engineered cells into the pulmonary circulation can be accomplished by infusion of the cells either into a peripheral vein or a central vein, from where they move with the circulation to the pulmonary system as previously described, and become lodged in the smallest arterioles of the vascular bed of the lungs. Direct injection into the pulmonary circulation can also be adopted, for example through a Swan Ganz catheter. Injection into the right ventricle or right atrium may be carried out using the pacing port of a Swan Ganz catheter. The infusion can be done either in a bolus form i.e. injection of all the cells during a short period of time, or it may be accomplished by a continuous infusion of small numbers of cells over a long period of time, or alternatively by administration of limited size boluses on several occasions over a period of time. Re-introduction of genetically engineered cells into the lungs can also be accomplished through inhalation of the cells using known pulmonary administration methods, such as an inhaler.

While the transfected cells themselves are largely or completely retained in the pulmonary circulation, and especially in the arterioles of the patient's lungs, the expression products of the transgenes thereof are not restricted in this manner. They can be expressed and secreted from the transfected cells, and travel through the normal circulation of the patient to other, downstream body organs where they can exert a therapeutic effect. Thus, while a preferred use of the process of the invention is in the treatment of pulmonary disorders, since the expression products initially contact the patient's pulmonary system, it is not limited to such treatments. The vectors can contain transgenes expressing products designed for treatment of other body organs of the patient. Such products expressed in the pulmonary system will target the other, predetermined organs and be delivered thereto by the natural circulation system of the patient.

Another preferred embodiment is the treatment of Acute Respiratory Distress Syndrome (ARDS). This ARDS results as a consequence of acute lung injury (ALI) that may have been caused by pneumonia, sepsis, or acute lung injury from another source. The treatment of the ARDS may include decreasing lung inflammation, decreasing septal edema, decreasing alveolar and/or endothelial inflammation, or alleviating another symptom of the ARDS. With certain cell types, such as mesenchymal and stem cells, the administration of the cells alone may treat the ARDS. Another embodiment comprises use of smooth muscle cells MSCs or fibroblast cells such as dermal fibroblasts, transformed to express a transgene, for example, Ang-1.

The invention is further described for illustrative purposes, in the following specific, non-limiting Examples.

BRIEF DESCRIPTION OF THE DRAWINGS

The invention will now be described, by way of example only, with reference to the accompanying drawings, in which:

FIGS. 1B and 1C respectively illustrate multiple cell-shaped fluorescent signals at fifteen minutes and 48 hours after jugular injection as described in Example 5;

FIGS. 2B and 2C respectively show the staining in the lung at 48 hours and 14 days following injection, as described in Example 6;

FIG. 5B shows similar results as FIG. 5A in animals transfected with the control vector, pcDNA 3.1 as described in Example 7;

FIG. 5C shows similar results as FIG. 5A following cell-based gene transfer of VEGF as described in Example 7:

FIG. 24 (e-g) show sections of lung 3 days post-administration of ELPCs: e shows ELPC cells trapped within distal arterioles; f shows engrafting of ELPCs into the endothelial layer of distal precapillary arterioles, g shows complete luminal incorporation. FIG. 24 (h-i) show sections of lung 21 days post-administration.

FIG. 25 is a bar graph showing the effect of early ELPC injection on right ventricular systolic pressure (A) and the ratio of right ventricular to left ventricular weight (RV/LV) (B) at end study (day 21)(prevention protocol). Rats treated with ELPCs exhibited a significantly lower RVSP with no significant decrease in RV/LV ratio ($P<0.001$).

FIG. 26 shows persistence of effect over a longer time period. RSVP in rats injected with fibroblasts versus ELPCs are shown at day 21 (A) and at a longer time periods (B). FIG. 26C shows histological examination of kidneys (a, b, c, d) and lungs (e-f) in MCT-ELPC-treated rats (b, d, e) versus controls (a, c, f).

FIG. 27(A) shows RVSP at 21 days after MCT and 14 days after cell therapy (day 35), in animals treated with MGT, ELPC, or ELPC cells transduced with and expressing eNOS. ELPC inhibited progression of RSVP, with eNOS-transduced ELPC's resulting in significantly lower RSVP levels. Rats receiving eNOS-ELPCs or ELPCs alone had markedly reduced hypertrophy (B).

FIG. 28A shows representative confocal projection images of lung sections perfused with fluorescent microspheres suspended in agarose and immunostained for α-smooth muscle action (SMA), a: control rats; b: rats treated with MCT (21 days); c: animals receiving ELPCs (prevention model); d: rats treated with MCT (35 days); e: animals receiving ELPCs (reversal model); f: animals receiving eNOS-transduced ELPCs.

FIG. 28B shows summary data for pulmonary microvascular perfusion for animals treated in the prevention (open bars) and reversal (closed bars) protocols (LEPC treated and eNOS-transduced ELPC treated animals).

FIG. 28C shows proportion of small pulmonary arterioles that are nonmuscularized (NM), partially muscularized (PM) or fully muscularized (FM) in the reverse protocol (ELPC treated and eNOS-transduced ELPC treated animals).

FIG. 30A shows the total cell count on BAL fluid to evaluate lung airspace inflammation. There was a 19-fold increase in total inflammatory cells in BAL fluid collected 3 days after LPS, which was reduced by 53% in MSCs-treated mice (non-/null-transfected), and by 96% with Ang-1-transfected MSCs (MSCs-pAng1). Group comparisons were analyzed by one-way ANOVA with Dunnett's post hoc test. *$p<0.05$ and **$p<0.01$, compare between LPS/Saline vs. each treated group (MSC5, MSC5-pFLAG, or MSCs-pAng1), n=5 per group.

FIG. 30B shows histological evaluation of therapeutic potential of MSCs and MSC-pAng1 on LPS-induced lung injury in mice. Representative images of hematoxylin and eosin stained lung sections from six experimental groups. Lungs were inflation-fixed with 4% paraformaldehyde, paraffin embedded, and then cut into 5-micron thick sections before being stained. Photomicrographs were obtained with a Nikon Eclipse E800 microscope with a 40× objective. Scale bar 20 µm.

FIG. 33 shows the effect of MSCs and MSCs-pAng1 on LPS-induced ALI Therapeutic efficacy was assessed by measurement of total protein, albumin, and 1 gM (biomarkers of pulmonary vascular leak resulting from disruption of the alveolar-capillary membrane barrier) in BAL fluid. FIG. 33A shows total protein concentration was measured by Bradford assay; FIG. 33B shows albumin, measured using a mouse-specific albumin ELISA; and FIG. 33C shows IgM as measured using a mouse IgM ELISA kit. Group comparisons were analyzed by one-way ANOVA with Dunnett's post hoc test.*p<0.05 and**p<0.01, LPS/Saline vs. each treated group (MSCs. MSCs-pFLAG, or MSCs-pAng1), n=5 per group.

FIG. 34A shows labelled MSCs (indicated by white arrows) in 5-IJm, PFA-fixed lung sections from LPS-injured mice sacrificed at 15 minutes (initial retention). FIG. 34B shows three-dimensional lung section from an animal that received labelled MSCs. Lung was inflated, stored in OCT, and cut into 50-µm thick section. Z-series images (30 sections, total thickness of the tissue scanned=17.71 µm) were collected with a 63× oil objective and projected in different axes, as shown. FIG. 34C shows pictures taken in z axis with a 20× objective, then stacked using Leica Confocal software. FIG. 34D shows flow cytometry of lung lobes (left upper and all right lobes), enzyme-digested into single cells then analyzed, n=5 per group. Scale bar=20 µm.

FIG. 35A, panels a and b show immunofluorescent staining for von Willebrand Factor and CMTMR-labeled Ang-1 transfected fibroblasts. FIG. 35A, panels c and d show immunofluorescent staining for Ang-1. A proportion of CMTMR-labeled Ang-1 transfected fibroblasts cells also expressed Ang-1 48 hours after injection (d). FIG. 35B shows quantitative real-time RT-PCR analysis of total Ang-1 mRNA levels, and shows a 53% reduction following LPS exposure that was restored by pretreatment with pAng-1 transfected cells. FIG. 35C shows that plasmid Ang-1 mRNA was undetectable in animals pretreated with pFLAG-transfected cells, while plasmid Ang-1 levels were similar in both groups that receive injection of pAng-1-transfected cells. FIG. 35D shows quantitative real-time RT-PCR analysis of Tie2 mRNA levels. The figures show a 59% reduction following LPS exposure that was partially restored by pretreatment with pAng-1 transfected cells. FIG. 35E shows immunoprecipitation and Western Blot analysis demonstrating that both Tie2 protein and phosphorylated Tie2 protein were decreased following LPS exposure and partially restored by pretreatment with pAng-1 transfected cells. * denotes significance of differences vs. pFLAG-transfected fibroblast injected rats challenged with saline; p<0.05. # denotes significance of differences vs. pFLAG-transfected fibroblast injected rats challenged with LPS; P<0.05. N=10/group. Scale bars=100 µm.

FIG. 36 shows Angiopoietin-1 cell therapy attenuating intra-alveolar septal thickness and airspace inflammation in rats. FIG. 36A shows representative hematoxylin and eosin stained lung sections demonstrating normal lung morphology in saline challenged rats after injection of either pFLAG-transfected cells (panel a) or pAng-1-transfected cells (panel b). The increased edema and infiltration observed in LPS challenged rats pretreated with pFLAG-transfected cells (panel c) was reduced in LPS challenged rats pretreated with pAng-1-transfected cells (panel d). FIG. 36B shows quantification of intra-alveolar septal thickness demonstrating that the LPS-induced 2-fold increase in septal thickness was significantly attenuated by pretreatment with pAng-1-transfected cells. FIG. 36C shows that the total number of cells in BALF was increased 4-fold following LPS challenge and pretreatment with pFLAG-transfected cells, but was significantly reduced by pretreatment with pAng-1-transfected cells.

FIG. 36D shows that total protein in BALF was increased 73% following challenge and pretreatment with pFLAG-transfected cells and tended to be reduced by pretreatment with pAng-1-transfected cells. FIG. 36E shows that lung wet weight to body weight ration was increased 20% following LPS challenge and pretreatment with pFLAG-transfected cells and tended to be reduced by pretreatment with pAng-1-transfected cells. * denotes significance of differences vs. pFLAG-transfected fibroblast injected rats challenged with saline; p<0.05. # denotes significance of differences vs. pFLAG-transfected fibroblast injected rats challenged with LPS; p<0.05. N=10/group. Scale bar=100 µm.

FIG. 37A shows quantitative real-time RT-PCR analysis of total ICAM-1 mRNA levels, which showed a 2-fold increase following LPS that was not affected by pretreatment with pAng-1-transfected cells. Western blot analysis of ICAM-1 showed no detectable difference in ICAM-1 expression between all experimental groups. FIG. 37B shows quantitative real-time RE-PCR analysis of total VCAM-1 mRNA levels showing a 2-fold increase following PLS that was not affected by pretreatment with pAng-1-transfected cells. Western blot analysis of VCAM-1 showed no detectable difference in VACM-1 expression between all experimental groups. FIG. 37C shows quantitative real-time RT-PCR analysis of total E-Selectin mRNA levels showing a 22-fold increase following LPS that was significantly attenuated by pretreatment with pAng-1-transfected cells. Western blot analysis of E-Selectin showed similar expression to mRNA levels. FIG. 37D shows quantitative real-time RT-PCR analysis of total P-Selectin mRNA levels showing a 32-fold increase following LPS that was not affected by pretreatment with pAng-1-transfected cells. Western blot analysis of P-Selectin was not performed due to lack of commercially-available antibodies. * denotes significance of differences vs. pFLAG-transfected fibroblast injected rats challenged with saline; p<0.05. # denotes significance of differences vs. pFLAG-transfected fibroblast injected rats challenged with LPS: p<0.05. N=10/group.

FIG. 38 shows angiopoietin-1 and Tie2 expression in a transgenic mouse model of ALI. FIG. 38A shows Western Blot analysis demonstrating that Ang-1 was reduced wildtype mice following LPS challenge compared to naïve but restored to naïve levels in both Ang-1-tTA binary transgenic and Tie2+/− mice. FIG. 38B shows that Tie2 protein is lower in Tie2 haploinsufficient mice compared to wildtype and Ang-1-tTA mice. Tie2 protein was reduced in wildtype mice and Ang-1-tTA mice following LPS challenge compared to naïve, but remained higher compared to Tie2+/−.

FIG. 39A shows representative hematoxylin and eosin stained lung sections, demonstrating normal lung morphology in naïve wildtype mice (panel a), Ang-1-tTA binary transgenic mice (panel b) and Tie2+/− mice (panel c). The increased edema and infiltration observed in LPS challenged wildtype mice (panel d) was attenuated in Ang-1-tTA binary transgenic mice (panel e) and exacerbated in Tie+/− mice (panel f). FIG. 39B shows quantification of intra-alveolar septal thickness demonstrating that the LPS-induced 2.7-fold increase in septal thickness is significantly attenuated in Ang-1-tTA binary transgenic mice and exacerbated in Tie2+/− mice. FIG. 39C shows the total number of cells in BALF, which was increased 11-fold following LPS challenge in wildtype mice, but was significantly reduced in Ang-1-tTA mice and increased in Tie2+/− mice. FIG. 39D shows that total protein in BALF was increased 3-fold following LPS challenge in wildtype mice and was significantly reduced in Ang-1-tTA mice and increased in Tie2+/− mice. * denotes significance vs. wildtype naïve mice; p<0.05. # denotes significance of differences vs. wildtype LPS challenged mice; p<0.05. N=5/group. Scale bar=100 μm.

FIG. 40A shows that the LPS-induced increase TNF-α was significantly attenuated in Ang-1-tTA binary transgenic mice compared to wildtype. FIG. 40B shows that the increased LPS-induced increase in BALF IL-β was significantly attenuated in Ang-1-tTA mice compared to wildtype. FIG. 40C shows that the LPS-induced increase in BALF IL-6 was significantly attenuated in Ang-1-tTA binary transgenic mice and significantly exaggerated in Tie2+/− mice compared to wildtype. * denotes significance of differences vs. wildtype naïve mice; p<0.05. # denotes significance of differences vs. wildtype LPS challenged mice; p<0.05. N=5/group.

FIG. 41 shows that Ang-1 overexpression reduces endothelial expression of adhesion molecules. FIG. 41A shows flow cytometric analysis, showing that the percentage of endothelial cells positive for E-Selectin expression increased 34-fold following LPS in wildtype mice and was reduced in Ang-10-tTA mice (left panel). The majority of total lung cells expressing E-Selectin were endothelial cells (right panel; endothelial cells indicated by open bars; non-endothelial cells indicated by closed bars). FIGS. 41B, 41C and 41D show that similarly, percentage of endothelial cells positive for P-Selectin, ICAM-1 and VCAM-1 expression was increased following LPS in wildtype mice and this was reduced in Ang-1-tTA transgenic mice (left panels). Again, the majority of total lung cells expressing adhesion molecules was endothelial cells (right panels; endothelial cells indicated by open bars; non-endothelial cells indicated by closed bars). * denotes significance of differences vs. wildtype naïve mice; p<0.05. # denotes significance of differences vs. wildtype LPS challenged mice; p<0.05. N=5/group.

FIG. 42 shows that Tie2 deficiency increased circulating levels of soluble adhesion molecules. FIGS. 42A, 42B and 42C show that soluble E-Selectin, P-Selectin and ICAM-1 were increased following LPS in wildtype mice and these were reduced in Ang-1-tTA binary transgenic mice and exaggerated in Tie2+/− mice. FIG. 42D shows that soluble VCAM-1 was unchanged following LPS in WT and Ang-1-tTA mice, but increased in Tie2+/− mice exposed to LPS compared to all other groups. * denotes significance of difference vs. wildtype naïve mice; p<0.05. # denotes significantly different wildtype LPS challenged mice: p<0.05. N=5/group.

EXAMPLE 1—PULMONARY ARTERY EXPLANT CULTURE

Figure 1:
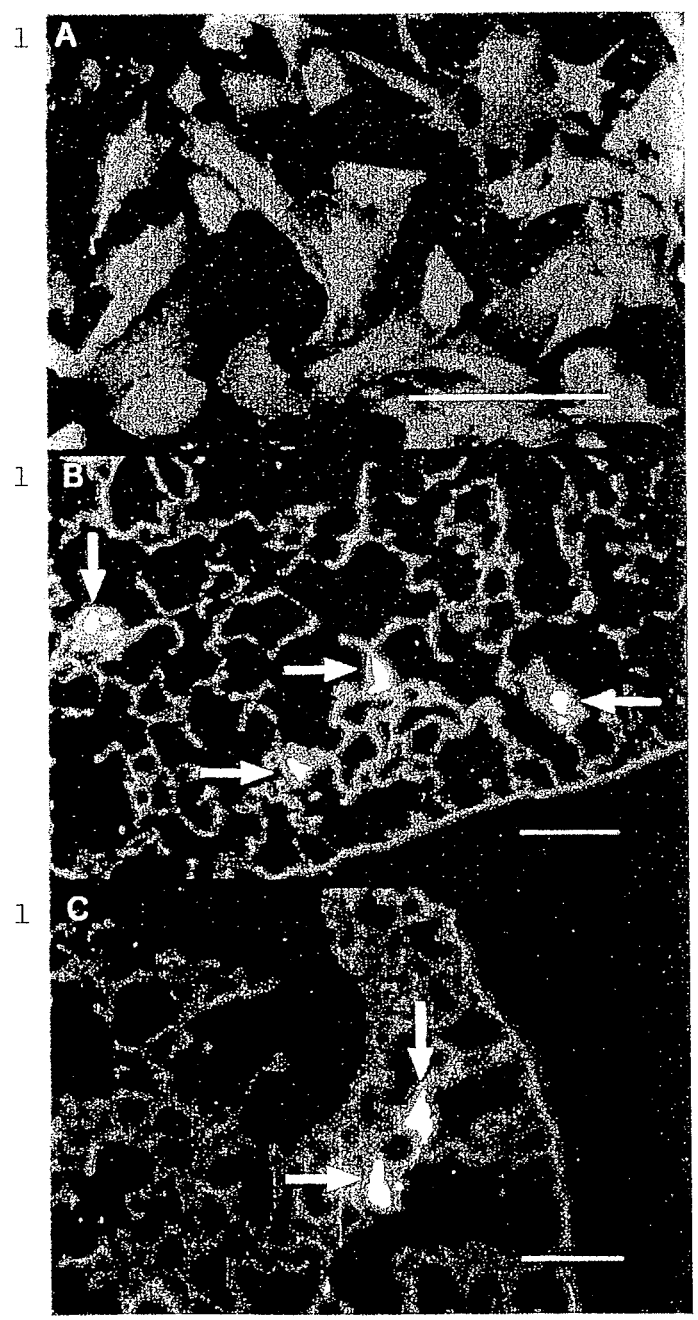
FIG. 1: 1A illustrates fluorescence of pulmonary artery smooth muscle cells immediately following incubation with the viable fluorophore CMTMR, as described below in Example 2.

Fisher 344 rats (Charles River Co.) were obtained at 21 days of age and were sacrificed by overdose with ketamine and xylazine. The main pulmonary artery was excised and transferred immediately into a phosphate-buffered saline (PBS) solution containing 2% penicillamine and streptomycin (Gibco BRL. Burlington, Ontario). The adventitia was carefully removed with sterile forceps, the artery opened longitudinally and the endothelium removed by abrasion of the intimal surface with a scalpel. The vessel was cut into approximately 4 millimeter square pieces which were placed intimal surface down on individual fibronectin-coated (Sigma Chemical Co., Mississauga, Ontario) tissue culture plates (Falcon, Becton Dickinson Canada. Mississauga, Ontario). The explants were then grown in Dulbecco's Modified Eagle Media with 10% fetal calf serum (FCS) and 2% penicillamine and streptomycin (all Gibco BRL), in a humidified environment with 95% O2 and 5% CO2 at 37° C., with the media being changed every second day. Explants were passaged using 0.05% trypsin/EDTA (Gibco BRL) once many cells of a thin, fusiform smooth muscle cell phenotype could be clearly seen growing from the pulmonary artery segment, at which time the remaining explanted tissue was removed. The cells were then grown in DMEM with 10% FCS and 2% penicillamine and streptomycin until they were to be used in further experiments.

EXAMPLE 2-ALPHA-SMOOTH MUSCLE ACTIN AND VON

Willebrand Factor Fluorescent Staining

To confirm their smooth muscle cell identity and rule out endothelial cell contamination, cells at the third passage were plated onto cover slips and grown until 70% confluent, at which time they were fixed in acetone at room temperature for 10 minutes. The cells were incubated with FCS for 30 minutes at 3 rC to block non-specific bonding sites, and then with a monoclonal anti-alpha-actin antibody (5 micrograms/millilitre) (Boehringer Mannheim) and a rabbit-derived polyclonal anti-von Willebrand Factor antibody (1:200 dilution) (Sigma) for 60 minutes at 3 rC in a covered humidified chamber. Negative control cover slips were incubated with PBS for the same duration of time. The cover slips were then washed in PBS, and incubated for 60 minutes at room temperature in a PBS solution containing a Cy3-conjugated donkey anti-mouse 1 gG antibody (1:200 dilution) (Jackson ImmunoResearch Laboratories), a fluorescein isothiocyanate (FITC)-conjugated goat anti-rabbit 1 gG antibody (1:200) (Jackson ImmunoResearch Laboratories), and Hoescht 33258 (Sigma), a fluorescent nuclear counterstain. The cover slips were again washed with PBS, and mounted using a 1:1 solution of PBS and gycerol. Slides were examined using an Olympus BX50 epifluorescent microscope with standard fluorescein, rhodamine and auto-fluorescent emission and excitation filters. For each cover slip the immunofluorescence for action, vWF, and for the nuclear counterstain Hoescht was indicated as positive or negative.

All of the explant derived cultures were found to be at least 97% pure smooth muscle cell with very rare endothelial contamination. This could be attributed to the vigorous debridement of the endothelial lining during the initiation of the explant, and early passaging with removal of the residual explant material.

Fluorescent Cell Labeling—Cells between the fifth and ninth passages were grown until 80% confluent and were then labeled with the viable fluorophore, chloromethyl trimethyl rhodamine (CMTMR. Molecular Probes Inc., Eugene, Oreg.). CMTMR affords a very accurate method of detecting ex vivi labeled cells, as the molecule undergoes irreversible esterification and glucoronidation after passing into the cytoplasm of a cell and thereby generates a membrane-impermeable final product. This active fluorophore is then unable to diffuse from the original labeled cell into adjacent cells or structures, and may be detected in vivo for several months, according to the manufacturer. The fluorescent probe was prepared by dissolving the lyophilized product in dimethyl sulfoxide (DMSO) to a concentration of 10 millimolar. This solution was stored at −20° C., an diluted to a final concentration of 25 micromolar in serum-free DMEM immediately prior to use. Cells were exposed to the labeling agent for 45 minutes, and were then washed with PBS twice and the regular media (DMEM with 10% FCS and 2% penicillin and streptomycin) replaced. The cells were grown overnight and harvested 24 hours later for injection into the internal jugular vein of recipient Fisher 344 rats.

A series of in vitro experiments was also performed by plating the cells on cover slips and the incubating them with the fluorophore to determine the quality and duration of fluorescence over time. Immediately after incubation with the fluorophore, CMTMR, at a concentration of 25 micromolar, 100% of cultured cells were found to fluoresce intensely when examined under a rhodamine filter (FIG. 1A). The white scale bar in FIG. 1A is 50 microns in length. Cells were also examined 48 hours and 7 days after labeling, and despite numerous cell divisions 100% of the cells present on the cover slip continued to fluoresce brightly (data not shown).

EXAMPLE 3—EX VIVO CELL TRANSFECTION WITH THE CMV-(3GAL PLASMID

The vector CMV-β Gal (Clontech Inc., Palo Alto, Calif.), which contains the beta-galactosidase gene under the control of the cytomegalovirus enhancer/promoter sequence, was used as a reporter gene to follow the course of in vivo transgene expression. The full-length coding sequence of VEGF165 was generated by performing a reverse transcription polymerase chain reaction using total RNA extracted from human aortic smooth muscle cells and the following sequence specific primers: sense 5' TCGGGCCTC-CGAAACCATGA 3' (SEQ ID. NO. 1), antisense 5' CCTG-GTGAGAGATCTGGTTC 3' (SEQ ID. NO. 2). This generated a 649 bp fragment which was cloned into the pGEM-T vector (Promega, Madison, Wis.), and sequenced to confirm identity. The fragment was then cloned into the expression vector pcDNA 3.1 at the EcoR1 restriction site, and correct orientation determined using a differential digest. The insert deficient vector (pcDNA 3.1) was used as a control for the monocrotaline experiments. All plasmid DNA was introduced into a JM109 strain of *E. Coli* via the heat-shock method of transformation, and bacteria was cultured overnight in LB media containing 100 micrograms/millilitre of ampicillin. The plasmid was then purified using an endotoxin-free purification kit according to the manufacturer's instructions (Qiagen Endotoxin-Free Maxi Kit. Qiagen Inc., Mississauga. Ontario), producing plasmid DNA with an A260/A280 ratio of greater than 1.75, and a concentration of at least 1.0 micrograms/microliter. Smooth muscle cells between the fifth and ninth passages were transfected using Superfect (Qiagen Inc., Mississauga, Ontario). This method was used to avoid the use of viral vectors and simultaneously obtain significant in vitro transfection efficiencies. The Superfect product is composed of charged polycations around which the plasmid DNA coils in a manner similar to histone-genomic DNA interactions. This Superfect-DNA complex then interacts with cell surface receptors and is actively transported into the cytoplasm, after which the plasmid DNA can translocate to the nucleus. This technique allows the transfection reaction to be performed in the presence of serum (an important consideration in sensitive primary cell lines), and produces no toxic metabolites.

Cells between the fifth and ninth passages were trypsinized the day prior to transfection to obtain a density of $5 \times 10^5$ cells/dish. The following day, 5 micrograms of plasmid DNA was mixed with 300 microlitres of serum-free DMEM in a sterile microcentrifuge tube. The plasmid-media solution was then vortexed with 50 microlitres of Superfect transfection agent (Qiagen), after which the tubes were incubated for 10 minutes at room temperature. The transfection mixture was then combined with 3 milliliters of DMEM with 10% FCS and 2% penicillin and streptomycin and applied to the culture dishes after the cells had been washed with PBS. The solution was allowed to incubate at 37° C. for 4 hours, and the cells were then washed with PBS twice and the standard media replaced. The transfected cells were allowed to grow overnight and were then harvested 24 hours later for animal injection. For every series of transfection reactions that were performed, one 100 millimeter dish of pulmonary artery smooth muscle cells was stained in vitro, to provide an estimate of the transfection efficiency of the total series.

In a total of 15 separate transfection reactions using the pCMV-α Gal plasmid, an average transfection efficiency of 11.4% was obtained with the primary pulmonary artery smooth muscle cells. No staining was seen in mock transfected cultures.

EXAMPLE 4—ANIMAL SURGERY

All animal procedures were approved by the Animal Care Committee of St. Michael's Hospital, Toronto. Canada. Six week old Fisher 344 rats (Charles River Co., St. Constant, Quebec) were anesthetized by intraperitoneal injection of xylazine (4.6 milligrams/kilogram) and ketamine (70 milligrams/kilogram), and the cervical area shaved and cleaned with iodine and ethanol. A midcervical incision was made with a scalpel and the right internal, external and common jugular veins identified. Plastic tubing of 0.02 millimetres external diameter was connected to a 23 gauge needle and flushed with sterile saline (Baxter). Thus tubing was then used to cannulate the external jugular vein and was introduced approximately 5 centimetres into the vein to what was estimated to be the superior vena caval level, and rapid venous blood return was used to confirm the catheter location.

For experiments to determine the time course of cell survival and transgene expression in the lung, pulmonary artery smooth muscle cells which had been labeled with the fluorophore CMTMR, or transfected with the plasmid vector CMV-a Gal, were trypsinized, and centrifuged at 850 rpm for 5 minutes. The excise media was removed and the pellet of cells was resuspended in a total volume of 2 millilitres of phosphate-buffered saline (PBS). A 50 microlitre aliquot of these resuspended cells was then taken and counted on a hemocytometer grid to determine the total number of cells present per millilitre of PBS. The solution was then divided into 1 millilitre aliquots of approximately 500,000 cells and transferred in a sterile manner to the animal care facility. These cells were then resuspended by gentle vortexing and injected into the animals via the external jugular vein catheter. The solution was infused slowly over one to two minutes and the catheter was then flushed again with sterile saline prior to removal. The external jugular vein was ligated, the incision closed with 3-0 interrupted absorbable sutures, and the animals allowed to recover from surgery.

EXAMPLE 5—DETECTION OF FLUORESCENTLY-LABELED CELLS IN TISSUE

At 15 minutes, 48 hours, 7 days, or 14 days after delivery of labeled cells (n=5 for each time-point except for 15 minutes where n=4), or saline injection (negative control, n=6), the animals were sacrificed by anesthetic overdose, and the chest cavity was opened. The pulmonary artery and trachea were flushed with saline, and the right and left lungs excised. Transverse slices were taken from the basal, medial and apical segments of both lungs, and specimens obtained from the liver, spleen, kidney and gastroenemius muscle. Tissue specimens were embedded in OCT compound (Sakura Finetek U.S.A. Inc., Torrance, Calif.) en face, and then flash frozen in liquid nitrogen. Ten micron sections were cut from these frozen blocks at 2 different tissue levels separated by at least 200 microns, and these sections were then examined under a fluorescent microscope using a rhodamine filter, and the number of intensely fluorescing cells was counted in each en face tissue specimen.

To provide an estimate of the total number of labeled cells present within the entire lung, the total number of fluorescent cells were counted in each lung section and averaged over the number of sections counted. A mathematical approximation could be made of the total number of cells present within the lung by utilizing Simpson's rule for the volume of a truncated cone. This equation bases the total volume of a cone on the relative areas of 3 different sections such that:

volume=[(areabasal section+areamiddle section)× height of the lung]/3+[areaapical section/2× height of the lung/3]+[8/6×(height of the lung/3)3].

The height of the lung was measured after organ harvesting, and the area of each transverse section was determined by planimetry. The average number of cells present in the three sections, divided by the total volume of these sections yielded an estimate of the cell number per unit volume. By multiplying this number by the total lung volume an estimate of the total number of cells within the lung could be obtained. To correct for the appearance of a single cell in multiple adjacent lung sections, rats were injected with 500.000 CMTMR labeled cells and sacrificed acutely. The lungs were prepared, harvested and embedded in the usual manner, and twenty serial sections, each 5 microns in thickness, were taken through the lung parenchyma. Each section was examined using a rhodamine filter and distinct individual cells were identified and their presence determined on adjacent sections. The number of 5 micron sections in which a single cell could be identified was counted and the average dimensions of a pulmonary artery smooth muscle cell in vivo was obtained. The average diameter observed was 16.4±1.22 microns. Therefore, the total number of cells calculated using the Simpson's formula was multiplied by 0.61 to correct for the presence of 1 cell in, on average, each 1.64 ten micron sections.

Approximately 57±5% of the labeled cells could be identified within the lung 15 minutes after intravenous delivery, as shown by white arrows in FIG. 1B. Most of these cells appeared to be lodged in the capillary circulation at the alveolar level. By 48 hours after cell delivery, a significant decrease in the total number of fluorescent cells identified was noted (34±7%, p<0.01), and the location of the cells also appeared to have changed. Many bright fluorescent signals were now identified within the pulmonary parenchyma, or were lodged within the wall of small vascular structures as shown by the white arrows in FIG. 1C. The white scale bar in FIGS. 1B and 1C is 50 microns in length. At 7 and 14 days after injection, a further decrease in cell number was noted (16±3% and 15±5% respectively, both p<0.001 as compared to 15 minute time-point), however the cells appeared to remain in approximately the same location. No brightly fluorescent signals were seen in any of the lungs injected with non-labeled smooth muscle cells.

In the spleen, liver and skeletal muscle tissue no fluorescent signals were identified. In 2 out of 4 kidneys examined at 48 hours following injection, irregular fluorescent signals could be identified. None of these appeared to conform to the shape of a whole cell, and were presumed to represent those cells that were sheared or destroyed during cell injection or shortly thereafter. In addition, no fluorescent signals were identified in any organ outside of the lung 7 days after injection.

EXAMPLE 6—DETECTION OF BETA-GALACTOSIDASE EXPRESSION IN TISSUE

At three time points after cell-based gene transfer (48 hours, 7 days, and 14 days), animals (n=7 for each time-point) were sacrificed and the chest opened. The pulmonary artery was flushed with saline and the trachea was cannulated and flushed with 2% paraformaldehyde until the lungs were well inflated. Transverse slices were taken from the basal, medial and apical segments of both lungs, and specimens obtained from the liver, spleen, kidney and gastroenemius muscle of certain animals. The specimens were incubated in 2% paraformaldehyde with 0.2% glutaraldehyde for 1 hour, and then rinsed in PBS. The tissue was then incubated for 18 hours at 3 rC with a chromogen solution containing 0.2% 5-bromo-4-chloro-3-indolyl-a-D-galactoside (X-Gal, Boehringer Mannheim, Laval, Quebec), 5 millimolar potassium ferrocyanide (Sigma), 5 millimolar potassium ferricyanide (Sigma), and 2 millimolar magnesium chloride (Sigma), all dissolved in phosphate buffered saline. The specimens were then rinsed in PBS, embedded in OCT compound (Miles Laboratories), cut into 10 micron sections, and counterstained with neutral red.

The en face sections were examined microscopically, and the number of intensely blue staining cells was determined. As one dish of cells was used for in vitro staining to determine the transfection efficiency for each reaction series, an estimate of the percentage of cells that were transfected with the reporter gene plasmid pCMV-α Gal could be made for every animal. Using this information and the mathematical calculation described for approximating the number of fluorescent cells present, an estimate could be made of the total number of transfected cells remaining at the time of animal sacrifice.

Figure 2:
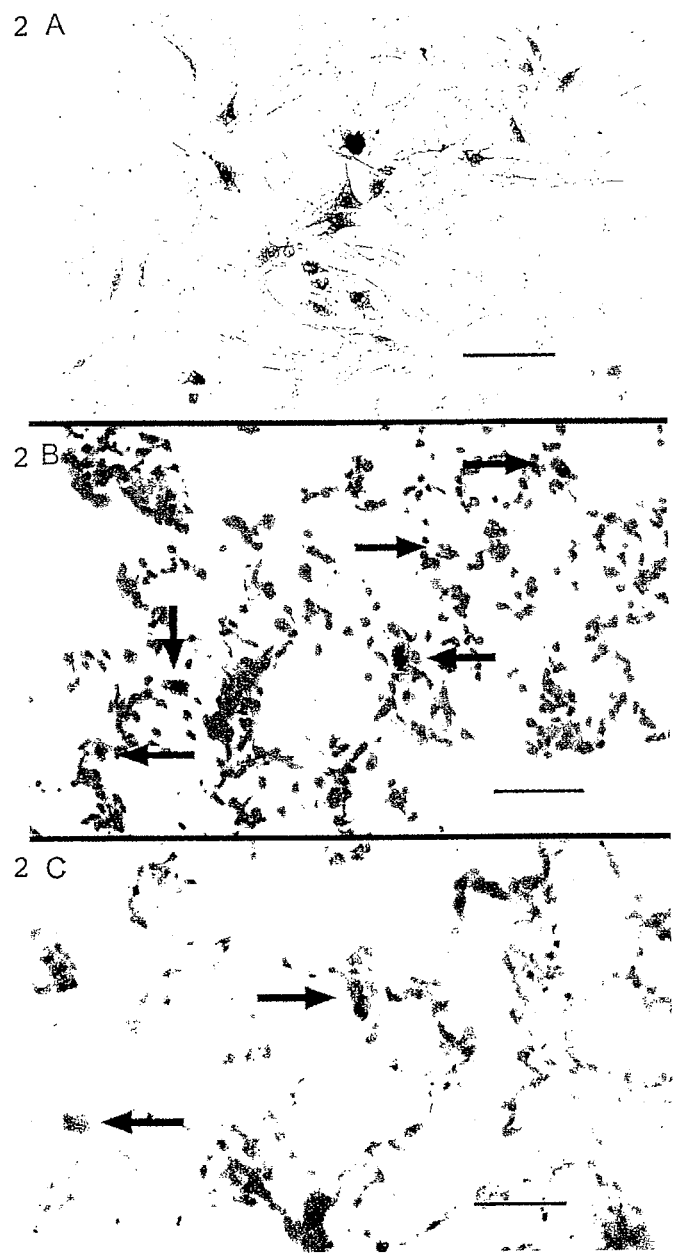
FIG. 2: 2A shows that a transfection efficiency of about 15% could be obtained with the primary pulmonary artery smooth muscle cells in vitro, discussed in Example 6.

In a total of 15 separate transfection reactions using the pCMV-α Gal plasmid, an average transfection efficiency of 13±0.5% was obtained with the primary pulmonary artery smooth muscle cells in vitro, and is 15% in FIG. 2: 2A. No staining was seen in mock transfected cultures.

Following incubation with the X-Gal chromogen solution, microscopic evidence of cell-based transgene expression could be clearly seen at 48 hours after injection of pCMV-α Gal transfected smooth muscle cells into the internal jugular vein (n=7), with multiple intense blue staining cells being seen throughout the lung (FIG. 2B), representing approximately 36±6% of the original transfected cells that were injected. As with the fluorescently-labeled cells, most of the beta-galactosidase expressing cells appeared to be lodged within the distal microvasculature. For example, in FIG. 2B, the staining cells are predominantly located in alveolar septae adjacent to small vessels, indicated by black arrows. By seven days after injection (n=4), a decline in the number of beta-galactosidase positive cells was noted (28±6%), and the intensity of staining also appeared to decrease. Again, the cells appeared to have either migrated into the pulmonary parenchyma or vascular wall. Fourteen days (n=6) after cell-based gene transfer, no further decrease in the number of cells identified was noted, but the intensity of beta-galactosidase staining of each cell had decreased further, as shown by the black arrows in FIG. 2C, which shows the remaining cells apparently located within the pulmonary parenchyma. The black scale bar in FIGS. 2A to 2C is 50 microns in length. No evidence of beta-galactosidase expression was detected in any of the lungs from animals (n=4, 3 at 7 days and 1 at 14 days) injected with non-transfected smooth muscle cells. At all three time-points, no evidence of pulmonary pathology, as determined by the presence of an abnormal polymorphonuclear or lymphocytic infiltrate, septal thickening or alveolar destruction, could be detected.

In the spleen and skeletal muscle of animals injected with transfected or non-transfected smooth muscle cells, no blue staining cells could be identified. Liver and renal specimens from animals injected with either transfected (n=5) or non-transfected (n=3) smooth muscle cells would occasionally show faint blue staining across the cut edge of the tissue (n=2 for each group), but no intense staining was seen at any time-point, and no staining was seen further than one high power field into the tissue.

EXAMPLE 7—MONOCROTALINE PREVENTION STUDIES

To determine if cell-based gene transfer of VEGF165 would be capable of inhibiting the development of pulmonary hypertension in an animal model of disease, pulmonary artery smooth muscle cells which had been transfected with either pVEGF or pcDNA 3.1 were trypsinized and divided into aliquots of 500.000 cells.

Monocrotaline is a plant alkaloid, a metabolite of which damages the pulmonary endothelium, providing an animal model of pulmonary hypertension.

Six to eight week old Fisher 344 rats were then anesthetized and injected subcutaneously with either 80 milligrams/kilogram of monocrotaline (n=13) (Aldrich Chemical Co., Milwaukee, Wis.) alone, or with monocrotaline and, via a catheter in the external jugular vein, either 500.000 pVEGF (n=15), or pcDNA 3.1 (n=13) transfected cells. The vein was tied off, the incision closed in the normal fashion, and the animals allowed to recover. At 28 days after injection, animals were reanesthetized, and a Millar microtip catheter reinserted via the right internal jugular vein into the right ventricle. The right ventricular systolic pressure was recorded, and the catheter was then inserted into the ascending aorta and the systemic arterial pressure recorded. The animals were then sacrificed and the hearts excised. The right ventricular (RV) to left ventricular plus septal (LV) weight ratios (RV/LV ratio) were determined as an indicator of hypertrophic response to long-standing pulmonary hypertension. Lungs were flushed via the pulmonary artery with sterile phosphate-buffered saline, and were gently insufflated with 2% paraformaldehyde via the trachea. Pulmonary segments were then either snap frozen in liquid nitrogen for subsequent RNA extraction, or were fixed via immersion in 2% paraformaldehyde for paraffin embedding and sectioning. The right ventricular systolic pressures and RV/LV ratios were compared between the pVEGF, pcDNA 3.1, and monocrotaline alone groups;

RNA extracted from rat lungs was quantified, and 5 micrograms of total RNA from each animal was reverse transcribed using the murine maloney leukemia virus reverse-transcriptase, and an aliquot of the resulting eDNA was amplified with the polymerase chain reaction (PCR) using the following sequence-specific primers: sense 5' CGCTACTGGCTTATCGAAATTAAT ACGACTCAC 3' (SEQ ID. NO. 3), antisense 5' GGCCITTGGTGAGGTIT-GATCCGCATAAT 3' (SEQ ID. NO. 4), for 30 cycles with an annealing temperature of 65° C. Ten microlitres of a fifty microlitre reaction were run on a 1.5% agarose gel. The upstream primer was located within the T7 priming site of the pcDNA 3.1 vector and therefore should not anneal with any endogenous RNA transcript, and the downstream primer was located within exon 4 of the coding region of VEGF. Therefore, the successful PCR reaction would selectively amplify only exogenous VEGF RNA. To control for RNA quantity and quality, a second aliquot of the same reverse transcription reaction was amplified with the following primers for the constitutively-expressed gene GAPDH: sense 5' CTCTAAGGCTGTGGGCAAGGTCAT 3' (SEQ ID. NO. 5), ', antisense 5' GAGATCCACCACCCTGTT-GCTGTA 3' (SEQ ID. NO.6). This reaction was carried out for 25 cycles with an annealing temperature of 58° C. Ten microlitres of a fifty microlitre reaction were run on a 1.5% agarose gel, and compared to the signal obtained from the VEGF PCR.

Paraformaldehyde fixed rat lungs were cut perpendicular to their long axis and were paraffin-embedded en face. Sections were obtained and stained using the elastin-von Giessen's (EVG) technique. The sections were assessed by a blinded observer who measured all vessels with a perceptible media within each cross-section under 40× magnification using the C+ computer imaging system. The medial area of each vessel was determined and an average was obtained for each vessel size from 0 to 30, 30 to 60, 60 to 90, 90 to 120, and greater than 120 microns in external diameter, for each animal. The averages from each size were compared between the pVEGF, pcDNA 3.1, and monocrotaline alone groups.

Figure 3:
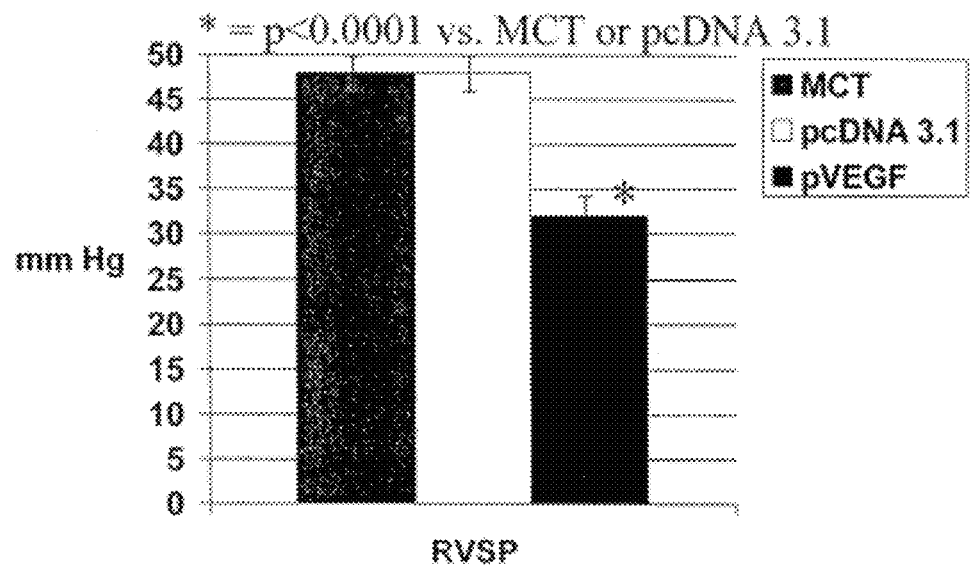
FIG. 3 provides a graphic representation of right ventricular systolic pressure four weeks after monocrotaline injection and cell-based gene transfer as described in Example 7.

Four weeks following monocrotaline injection (n=11) alone, the right ventricular systolic pressure was increased to 48±2 mm Hg, and there was no improvement in those animals who received the pcDNA 3.1 transfected cells (n=10) with the average RVSP remaining at 48±2 mm Hg. However, in those animals treated with the pVEGF transfected cells (n=15) the RV pressure was significantly decreased to 32±2 mm Hg (p<0.0001). In this regard, see FIG. 3, which shows right ventricular systolic pressure (RVSP) graphed for the monocrotaline alone (MCT), the control vector transfected (pcDNA 3.1) and the animals injected with the VEGF transfected smooth muscle cells (pVEGF). Four weeks after injection of the pulmonary endothelial toxin monocrotaline and transfected cells, the RVSP was increased to 48 mm Hg in the MCT and pcDNA 3.1 groups, but was significantly decreased to 32 mm Hg in the pVEGF transfected animals.

Figure 4:
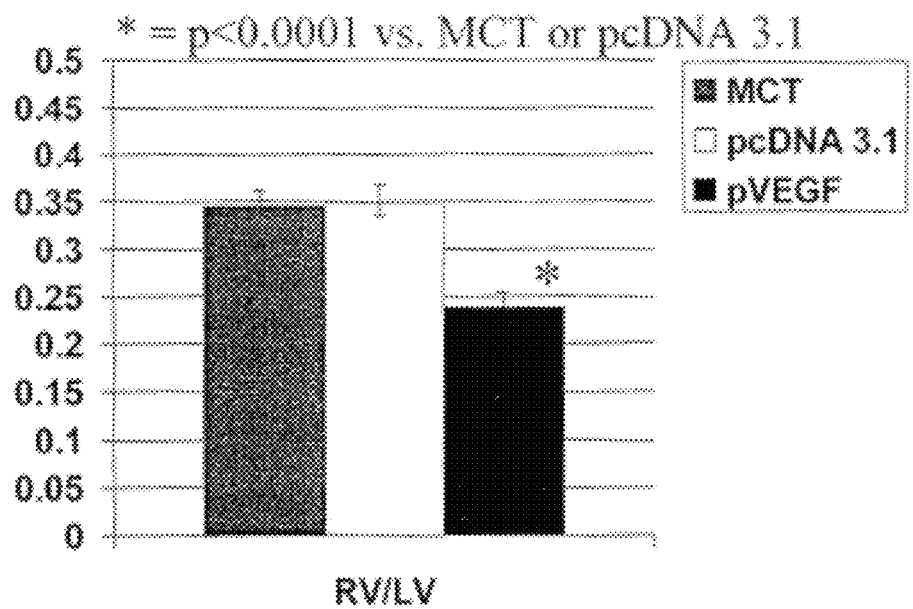
FIG. 4 provides a graphic representation of right ventricular to left ventricular plus septal weight ratio four weeks after monocrotaline injection and cell-based gene transfer as described in Example 7.

As anticipated from the long-standing pulmonary hypertension, the RV/LV ratio was significantly elevated from baseline following monocrotaline injection (n=13) to 0.345±0.015 and was very similar in the pcDNA 3.1 transfected group (n=13, 0.349±0.015, p>0.8). Following VEGF gene transfer (n=12) the ratio was significantly reduced to 0.238±0.012 (p<0.0001). No difference in aortic pressure was noted. See FIG. 4, in which the right ventricular to left ventricular plus septal weight ratio (RV/LV ratio) is used as a measure of long-standing pulmonary and right ventricular hypertension. Four weeks after injection of the pulmonary endothelial toxin monocrotaline and transfected cells, the RV/LV ratio is significantly elevated to 0.345 in the MGT group and 0.349 in the pcDNA 3.1 group, but was decreased to 0.238 in the pVEGF transfected animals.

Figure 5:
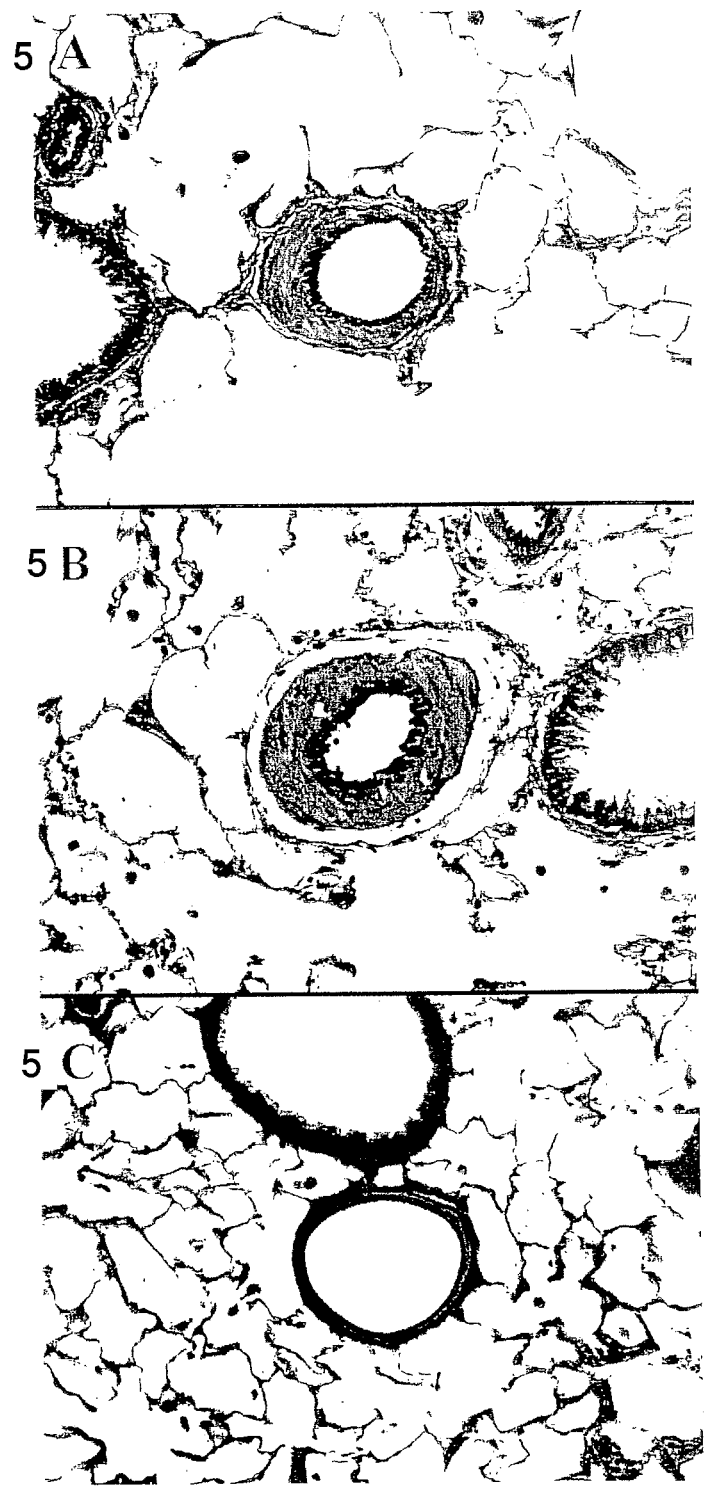
FIG. 5: 5A illustrates the smooth muscle hypertrophic and hyperplastic response observed in mid-sized pulmonary vessels four weeks following subcutaneous injection of monocrotaline as described in Example 7.
Figure 6:
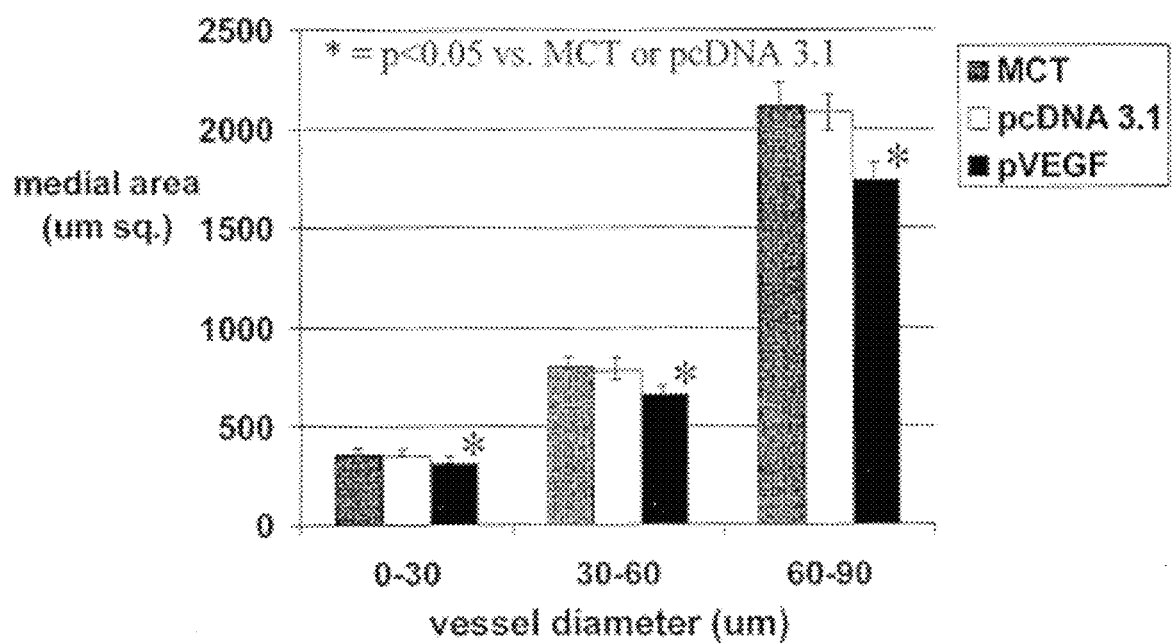
FIG. 6 is a graphic representation of medial area following monocrotaline injection and gene transfer as described in Example 7.

Morphometric analysis of the tissue sections revealed that in both the monocrotaline alone and the pcDNA 3.1 treated groups, the medial area for the vessel groups from 0 to 30, 30 to 60 and 60 to 90 microns was significantly increased, as compared to the VEGF treated animals (p<0.05). In this regard, see FIGS. 5A to 5C showing that four weeks following subcutaneous injection of the pulmonary endothelial toxin, monocrotaline, a marked smooth muscle hypertrophic and hyperplastic response was observed in the mid-sized pulmonary vessels (FIG. 5A). Similar results were seen in animals transfected with the control vector, pcDNA 3.1 (FIG. 5B). Following cell-based gene transfer of VEGF, a significant decrease in medial thickness and area was observed in vessels of 0 to 90 microns external diameter (FIG. 5C). See also FIG. 6, which shows that a significant attenuation of medial area was detected in those animals treated with monocrotaline and VEGF, as compared to those who received monocrotaline alone or monocrotaline and the null transfected cells (pcDNA 3.1).

Figure 7:
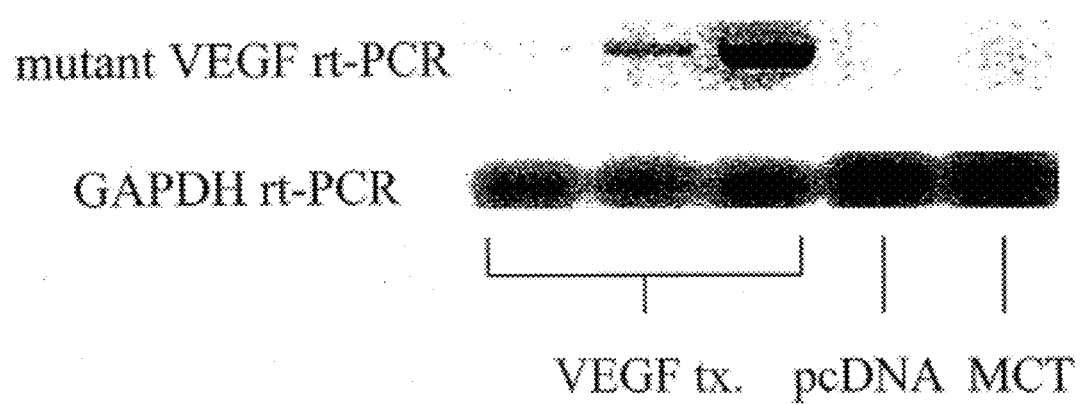
FIG. 7 graphically represents results obtained by selectively amplifying the exogenous VEGF transcript as described in Example 7.

Using the viral-based primers, the exogenous VEGF transcript was selectively amplified using the polymerase chain reaction. In this regard, see FIG. 7 which shows that, in animals injected with the VEGF transfected cells, a variable but consistently detectable signal could be detected at the correct size (lanes 1-3), however no signal was detectable in either the monocrotaline alone or control transfected animals (lanes 4 and 5). RNA quality and loading was assessed by amplifying the house-keeping gene GAPDH, which was consistently present in all samples. This demonstrates that the foreign RNA was being transcribed 28 days after cell-based gene transfer and that potentially the presence of the transcript, and presumably the translated protein, was causally related to the lowering of RVSP in the VEGF treated animals.

EXAMPLE 8—MONOCROTALINE REVERSAL STUDIES

To determine if cell-based gene transfer of VEGF165 would be capable of reversing or preventing the progression of established pulmonary hypertension in an animal model of disease, six to eight week old Fisher 344 rats were injected subcutaneously with 80 milligrams/kilogram of monocrotaline. Fourteen days after monocrotaline injection the animals were anesthetized and a Millar catheter was passed into the right ventricle and the RV pressure recorded. Pulmonary artery smooth muscle cells transfected with either pVEGF (n=10) or pcDNA 3.1 (n=8) were then injected in aliquots of 500.000 cells into the external jugular vein, and the animals allowed to recover. At 28 days after monocrotaline injection, and 14 days after cell-based gene transfer, the animals were reanesthetized, and a Millar microtip catheter reinserted via the right internal jugular vein into the right ventricle. The right ventricular systolic pressure (RVSP) was recorded, and the catheter was then inserted into the ascending aorta and the systemic arterial pressure recorded. The animals were then sacrificed and the hearts excised. The RV/LV ratios were determined as an indicator of hypertrophic response to long-standing pulmonary hypertension. The right ventricular systolic pressures and RV/LV ratios were compared between the pVEGF and pcDNA 3.1 groups.

Figure 8:
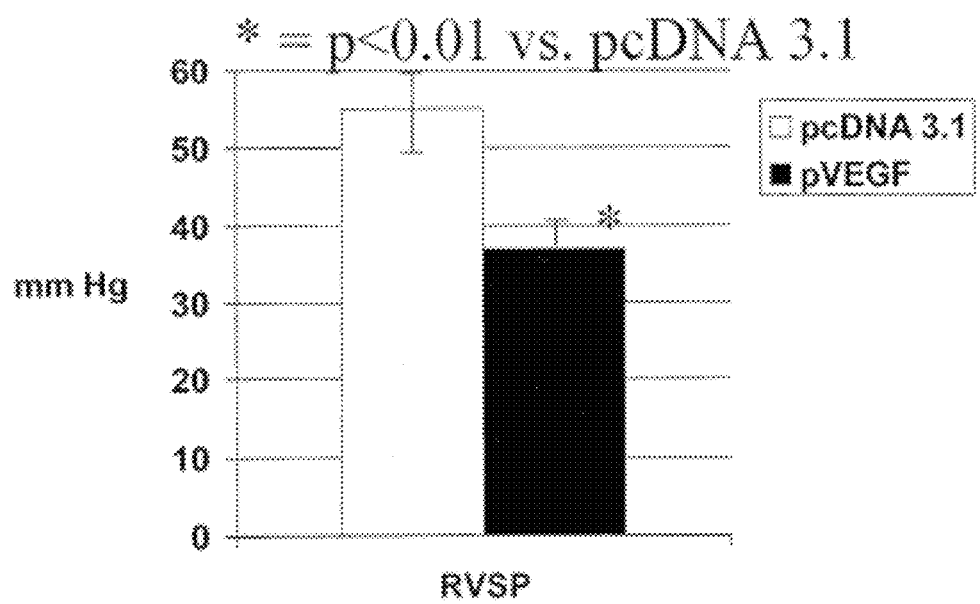
FIG. 8 provides a graphic representation of right ventricular systolic pressure following monocrotaline injection and delayed gene transfer as described in Example 8.

Two weeks after monocrotaline injection, the RVSP was elevated to 27±1 mm Hg. In the animals who received pcDNA 3.1 transfected cells the pressure was further increased to 55±5 mm Hg at four weeks after monocrotaline delivery. However, in the pVEGF treated animals the RVSP had only increased to 37±3 mm Hg (p<0.01). In this regard, see FIG. 8 in which the right ventricular systolic pressure (RVSP) is graphed for the animals injected with the control vector transfected (pcDNA 3.1) and the VEGF transfected smooth muscle cells (pVEGF), 14 days after monocrotaline injection. Four weeks after injection of the pulmonary endothelial toxin monocrotaline, the RVSP was increased to 55 mm Hg in the pcDNA 3.1 group, but was significantly decreased to 37 mm Hg in the pVEGF transfected animals.

Figure 9:
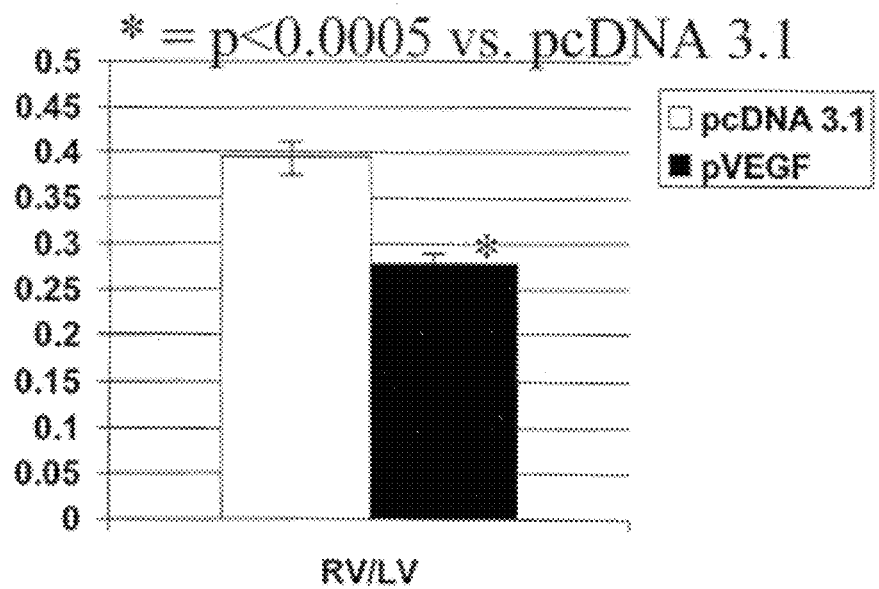
FIG. 9 provides a graphic representation of right ventricular to left ventricular plus septal weight ratio following monocrotaline injection and delayed gene transfer (reversal experiments) as described in Example 8.

The RV/LV ratio was significantly elevated in the pcDNA group to 0.395±0.022, but following VEGF gene transfer the ratio was significantly reduced to 0.278±0.012 (p<0.0005). Again no difference in aortic pressure was noted. In this regard, see FIG. 9, in which the right ventricular to left ventricular plus septal ratio (RV/LV) is graphed for the animals injected with the control vector transfected (pcDNA 3.1) and the VEGF transfected smooth muscle cells (pVEGF), 14 days after monocrotaline injection. Four weeks after injection of monocrotaline, the ratio was increased to 0.395 in the pcDNA 3.1 group, but was significantly decreased to 0.278 in the pVEGF transfected animals.

EXAMPLE 9—TREATMENT OF PULMONARY HYPERTENSION WITH NITRIC OXIDE Synthase Introduced by Cell Based Gene Transfer Pulmonary artery smooth muscle cells (SMC) were harvested from Fisher 344 rats, and transfected in vitro with the full-length coding sequence for endothelial nitric oxide synthase (eNOS) under the control of the CMV enhancer/promoter. Thirteen syngeneic rats were injected with 80 mg/kg of monocrotaline subcutaneously, and of these, 7 were randomized to receive eNOS transfected SMC ($5 \times 10^5$) via the jugular vein, 28 days later right ventricular (RV) pressure was measured by means of a Millar micro-tip catheter and pulmonary histology examined.

ENOS gene transfer significantly reduced systolic RV pressure from 52+/−6 mm Hg in control animals (monocrotaline alone, n=6) to 33+/−7 in the eNOS treated animals (n=7, p=−0.001). Similarly, RV diastolic pressures were reduced from 15+/−7 mm Hg in the controls, to 4+/−3 in the eNOS treated animals (p=0.0055). In addition, there was a significant attenuation of the vascular hypertrophy and neomuscularization of small vessels in the animals treated with eNOS.

Cell-based gene transfer of the nitric oxide synthase to the pulmonary vasculature is thus an effective treatment strategy in the monocrotaline model of PPH. It offers a novel approach with possibilities for human therapy.

Statistical Analysis

Data are presented as means±standard error of the mean. Differences in right ventricular pressures. RV/LV ratios, and medial area in the pVEGF, pcDNA 3.1, and monocrotaline transfected animals were assessed by means of an analysis of variance (ANOVA), with a post-hoc analysis using the Bonferroni correction, for the prevention experiments. Unpaired t-tests were used to compare differences in right ventricular pressures and RV/LV ratios in the pVEGF and pcDNA 3.1 treated animals, for the reversal experiments. Differences in the number of fluorescently labeled cells or transfected cells over time were assessed by means of an analysis of variance (ANOVA), with a post-hoc analysis using a Fisher's Protected Least Significant Difference test. In all instances, a value of p<0.05 was accepted to denote statistical significance.

EXAMPLE 10—SKIN FIBROBLAST EXPLANT CULTURE

Fisher 344 rats (Charles River Co.) were obtained at 21 days of age and were sacrificed by overdose with ketamine and xylazine. The hair was carefully shaved and the back skin was excised and transferred immediately into a phosphate-buffered saline (PBS) solution containing 2% penicillamine and streptomycin (Gibco BRL, Burlington, Ontario). The epidermal and deep fat and connective tissue was removed using a scalpel. The dermal tissue was cut into approximately 4 millimeter square pieces which were placed on individual fibronectin-coated (Sigma Chemical Co., Mississauga, Ontario) tissue culture plates (Falcon, Becton Dickinson Canada, Mississauga, Ontario). The explants were then grown in Dulbecco's Modified Eagle Media with 20% fetal calf serum (FCS) and 2% penicillamine and streptomycin (all Gibco BRL), in a humidified environment with 95% 02 and 5% C02 at 3 rC, with the media being changed every second day. Explants were passaged using 0.05% trypsin/EDTA (Gibco BRL) once many thin, spindle-shaped cells could clearly be seen growing from the dermal explant and the remaining explanted tissue was removed. The cells were then grown in DMEM with 20% FCS and 2% penicillamine and streptomycin until they were to be used in further experiments.

The purity of the cells as to effective type was checked, using antibodies and standard staining techniques, to determine the approximate number of available, effective cells of fibroblast lineage.

Fluorescent cell labeling of the cells was conducted as described in Example 1, followed by in vitro experiments to determine fluorescence, also as described in Example 1.

EXAMPLE 11—EX VIVO FIBROBLAST CELL TRANSFECTION WITH THE CMV-A Gal Plasmid

The vector CMV-α Gal (Clontech Inc., Palo Alto, Calif.), which contains the beta-galactosidase gene under the control of the cytomegalovirus enhancer/promoter sequence, was used as a reporter gene to follow the course of in vivo transgene expression. Fibroblasts were grown to 70 to 80% confluence. The optimal ratio of liposome to DNA was determined to be 6 µg of liposome/1 µg of DNA. Cells were washed with DMEM medium (no additives) and 6.4 mls of DMEM was added to each 100 mm plate. 200 µl of Genefector (Vennova Inc., Pablo Beach Fla.) was diluted in 0.8 mls of DMEM and mixed with 16 µg of DNA (CMV-α Gal) also diluted in 0.8 ml of DMEM. The liposome solution was then added dropwise over the entire surface of the plate, which was gently shaken and incubated at 30° C. for eight hours. This method was used to avoid the use of viral vectors and simultaneously obtain significant in vitro transfection efficiencies. The Genefector product is an optimized liposome preparation. This Genefector-DNA complex then interacts with cell surface and is transported into the cytoplasm, after which the plasmid DNA can translocate to the nucleus.

Then the transfection medium was replaced with 20% FBS, with 2% penicillin/streptomycin in M199 media and incubated for 24 to 48 hours. This method resulted in transfection efficiencies between 40 and 60%.

EXAMPLE 12—ANIMAL SURGERY AND DETECTION OF FLUORESCENTLY-LABELED Cells in Tissue Animal surgery followed by introduction of dermal fibroblast cells labeled with CMTMR or transfected with plasmid vector CMV-Gal, was conducted as described in Examples 4 and 5, and the fluorescently labeled fibroblast cells in tissue were similarly detected.

At 30 minutes or 24 hours after delivery of labeled cells (n=3 for each time-point), or saline injection (negative control, n=3), the animals were sacrificed by anesthetic overdose, and the chest cavity was opened. The pulmonary artery and trachea were flushed with saline, and the right and left lungs excised. Transverse slices were taken from the basal, medial and apical segments of both lungs, and specimens obtained from the liver, spleen, kidney and gastronemius muscle. Tissue specimens were embedded in OCT compound (Sakura Finetek U.S.A. Inc., Torrance, Calif.) en face, and then flash frozen in liquid nitrogen. Ten micron sections were cut from these frozen blocks at 2 different tissue levels separated by at least 200 microns, and these sections were then examined under a fluorescent microscope using a rhodamine filter, and the number of intensely fluorescing cells was counted in each en face tissue specimen.

The estimate of the total number of labeled cells present within the entire lung was obtained as described in Example 5.

Thirty minutes after fibroblast delivery, 373±36 CMTMR-labeled cells 1 cm2 were identified within the lung sections, which represented approximately 60% of the total number of cells injected. After 24 hours there was only a slight decrease in CMTMR-labeled cells to 317±4/cm2 or 85% of the 30-minute value, indicating excellent survival of transplanted cells. The survival of CMTMR-labeled cells at later time points of 2, 4, 7, and 14 days and 1, 2, 3 and 6 months are also evaluated to establish the time course of transplanted cell survival in the lungs of recipient rats. No brightly fluorescent signals were seen in any of the lungs injected with non-labeled smooth muscle cells.

In the spleen, liver and skeletal muscle tissue no fluorescent signals were identified. In 2 out of 4 kidneys examined, irregular fluorescent signals could be identified. None of these appeared to conform to the shape of a whole cell, and were presumed to represent those cells that were sheared or destroyed during cell injection or shortly thereafter. In addition, no fluorescent signals were identified in any organ outside of the lung 7 days after injection.

EXAMPLE 13 MONOCROTALINE PREVENTION STUDIES WITH TRANSFECTED Dermal Fibroblasts The procedure of Example 7 was largely repeated to determine if cell-based gene transfer of VEGF165 in dermal fibroblasts would be capable of inhibiting the development of pulmonary hypertension in an animal model of the disease, dermal fibroblasts which had been transfected with either pVEGF or pcDNA 3.1 (an empty vector) were prepared as described above. The full-length coding sequence of VEGF165 was generated by performing a reverse transcription polymerase chain reaction using total RNA extracted from human aortic smooth muscle cells and the following sequence specific primers: sense 5' TCGGGC-CTCCGAAACCATGA 3' (SEQ ID. NO. 7), antisense 5' CCTGGTGAGAGATCTGGTTC 3'(SEQ ID. NO. 8). This generated a 649 bp fragment which was cloned into the pGEM-T vector (Promega, Madison, Wis.), and sequenced to confirm identity. The fragment was then cloned into the expression vector pcDNA 3.1 at the EcoR1 restriction site, and correct orientation determined using a differential digest. The insert deficient vector (pcDNA 3.1) was used as a control for the monocrotaline experiments. All plasmid DNA was introduced into a JM109 strain of E. Coli via the heat-shock method of transformation, and bacteria were cultured overnight in LB media containing 100 micrograms/millilitre of ampicillin. The plasmid was then purified using an endotoxin-free purification kit according to the manufacturer's instructions (Qiagen Endotoxin-Free Maxi Kit, Qiagen Inc., Mississauga, Ontario), producing plasmid DNA with an A260/A280 ratio of greater than 1.75, and a concentration of at least 1.0 micrograms/microliter.

Transfected dermal fibroblasts were trypsinized and divided into aliquots of 500,000 cells. Six to eight week old Fisher 344 rats were then anesthetized and injected subcutaneously with either 80 milligrams/kilogram of monocrotaline (n=13) (Aldrich Chemical Co., Milwaukee, Wis.) alone, or with monocrotaline and, via a catheter in the external jugular vein, either 500,000 pVEGF (n=5), or pcDNA 3.1 (n=3) transfected cells.

Following the procedure described in Example 7, the vein was tied off, the incision closed in the normal fashion, and the animals allowed to recover. At 28 days after injection, animals were re-anesthetized, and a Millar microtip catheter reinserted via the right internal jugular vein into the right ventricle. The right ventricular systolic pressure was recorded, and the catheter was then inserted into the ascending aorta and the systemic arterial pressure recorded. The animals were then sacrificed and the hearts excised. The right ventricular (RV) to left ventricular plus septal (LV) weight ratios (RV/LV ratio) were determined as an indicator of hypertrophic response to long-standing pulmonary hypertension. Lungs were flushed via the pulmonary artery with sterile phosphate-buffered saline, and were gently insufflated with 2% paraformaldehyde via the trachea. Pulmonary segments were then either snap frozen in liquid nitrogen for subsequent RNA extraction, or were fixed via immersion in 2% paraformaldehyde for paraffin embedding and sectioning. The right ventricular systolic pressures and RV/LV ratios were compared between the pVEGF, pcDNA 3.1, and monocrotaline alone groups.

RNA extracted from rat lungs was quantified, and 5 micrograms of total RNA from each animal was reverse transcribed using the murine maloney leukemia virus reverse-transcriptase, and an aliquot of the resulting eDNA was amplified with the polymerase chain reaction (PCR) using the following sequence-specific primers: sense 5' CGCTACTGGCTTATCGAAATTAAT ACGACTCAC 3' (SEQ ID. NO. 9), antisense 5' GGCCTTGGTGAGGTIT-GATCCGCATAAT 3' (SEQ ID. NO. 10), for 30 cycles with an annealing temperature of 65° C. Ten microlitres of a fifty microlitre reaction were run on a 1.5% agarose gel. The upstream primer was located within the T7 priming site of the pcDNA 3.1 vector and therefore should not anneal with any endogenous RNA transcript, and the downstream primer was located within exon 4 of the coding region of VEGF. Therefore, the successful PCR reaction would selectively amplify only exogenous VEGF RNA. To control for RNA quantity and quality, a second aliquot of the same reverse transcription reaction was amplified with the following primers for the constitutively-expressed gene GAPDH: sense 5' CTCTAAGGCTGTGGGCAAGGTCAT 3' (SEQ ID. NO. 11), antisense 5' GAGATCCACCACCCTGTT-GCTGTA 3' (SEQ ID. NO. 12). This reaction was carried out for 25 cycles with an annealing temperature of 58° C. Ten microlitres of a fifty microlitre reaction were run on a 1.5% agarose gel, and compared to the signal obtained from the VEGF PCR.

Paraformaldehyde fixed rat lungs were cut perpendicular to their long axis and were paraffin-embedded en face. Sections were obtained and stained using the elastin-von Giessen's (EVG) technique. The sections were assessed by a blinded observer who measured all vessels with a perceptible media within each cross-section under 40× magnification using the C+ computer imaging system. The medial area of each vessel was determined and an average was obtained for each vessel size from 0 to 30, 30 to 60, 60 to 90, 90 to 120, and greater than 120 microns in external diameter, for each animal. The averages from each size were compared between the pVEGF, pcDNA 3.1, and monocrotaline alone groups.

Four weeks following monocrotaline injection (n=11) alone, the right ventricular systolic pressure was increased to 48±2 mm Hg, and there was no improvement in those animals who received the pcDNA 3.1 transfected cells (n=3) with the average RVSP remaining at 48±2 mm Hg. However, in those animals treated with the pVEGF transfected fibroblasts (n=5) the RV pressure was significantly decreased to 32±2 mm Hg ($p<0.0001$).

As anticipated from the long-standing pulmonary hypertension, the RV/LV ratio was significantly elevated from baseline following monocrotaline injection (n=13) to 0.345±0.015 and was very similar in the pcDNA 3.1 transfected group (n=3). Following VEGF gene transfer (n=5) the ratio was significantly lower than the pcDNA 3.1 transfected group. No difference in aortic pressure was noted. Four weeks after injection of the pulmonary endothelial toxin monocrotaline and transfected cells, the RV/LV ratio is significantly elevated in the MCT group and in the pcDNA 3.1 group, but was lower in the pVEGF transfected animals.

Morphometric analysis of the tissue sections revealed that in both the monocrotaline alone and the pcDNA 3.1 treated groups, the medial area for the vessel groups from 0 to 30, 30 to 60 and 60 to 90 microns was significantly increased, as compared to the VEGF treated animals. Similar results were seen in animals transfected with the control vector, pcDNA 3.1. Following cell-based gene transfer of VEGF, a significant decrease in medial thickness and area was observed in vessels of 0 to 90 microns external diameter.

Using the plasmid-based primers, the exogenous VEGF transcript was selectively amplified using the polymerase chain reaction. RNA quality and loading was assessed by amplifying the house-keeping gene GAPDH, which was consistently present in all samples. This demonstrated that the foreign RNA was being transcribed 28 days after cell-based gene transfer and that potentially the presence of the transcript, and presumably the translated protein, was causally related to the lowering of RVSP in the VEGF treated animals.

Blood taken from the animals by left ventricular puncture immediately before sacrifice was analyzed for pH, oxygen loading (pO2), carbon dioxide loading (pCO2) and % saturation. The results are given below.

Blood Analysis Data

VEGF/Fibroblast Transfected Animals

|  | pH | pCO2 | pO2 | % Sat'n |
|---|---|---|---|---|
| Mean (of 5 animals) | 7.374 | 51.2 | 78.3 | 86.58 |
| Standard deviation, SD | 0.0502 | 5.699 | 17.89 | 9.867 | cDNA/Fibroblast Transfected Animals

|  | pH | pCO2 | pO2 |  |
| --- | --- | --- | --- | --- |
| Mean (of 3 animals) | 7.35 | 58.333 | 60.8 | 74.4 |
| SD | 0.02 | 3.761 | 7.615 | 7.882 |

These results indicate preliminarily that arterial O2 tension and saturation are better in the VEGF transfected group than in animals receiving null-transfected cells. This is consistent with the improvement in pulmonary hemodynamics and lung vascular morphology, and argues against significant right to left shifting as might occur in pulmonary arterial to venous shunts.

The creation of "shunting"—formation of new passageways between the arteries and the capillaries of the pulmonary system, by-passing the veins and thereby limiting the blood oxygen up-take, does not occur to any problematic extent, according to indications.

Discussion

The present invention represents evidence of successful non-viral gene transfer to the pulmonary vasculature using various types of transfected cells e.g. smooth muscle cells and dermal fibroblasts, and provides a demonstration of potential therapeutic efficacy of an angiogenic strategy in the treatment of PH using this approach. This method of delivery was associated with a high percentage of cells being retained within the lung at 48 hours, as determined by both the fluorescence labeling technique and by the reporter gene studies using beta-galactosidase, and with moderate but persistent gene expression over 14 days. These results roughly parallel what has previously been demonstrated with a viral-based method of intravascular gene delivery to the pulmonary vasculature (see Schachtner, S. K., J. J. Rome, R. F. Hoyt, Jr., K. D. Newman, R. Virmani, D. A. Dichek, 1995. In vivo adenovirus-mediated gene transfer via the pulmonary artery of rats. Circ. Res. 76:701-709; and Rodman. D. M., H. San, R. Simari, D. Stephan. F. Tanner, Z. Yang, G. J. Nabel, E. G. Nabel, 1997. In vivo gene delivery to the pulmonary circulation in rats: transgene distribution and vascular inflammatory response. Am. J. Respir. Cell Mol. Bioi. 16:640-649).

However, the cell-based technique provided by the present invention avoids the use of a potentially immunogenic viral construct, was not associated with any significant pulmonary or systemic inflammation, and permits more selective transgene expression within the pulmonary microvasculature, and in particular the targeting of transgene expression localized to the distal pulmonary arteriolar region, which is primarily responsible for determining pulmonary vascular resistance, and therefore PH.

The present invention addresses several key questions related to the feasibility of a cell-based gene transfer approach for the pulmonary circulation, including the survival of genetically engineered cells and the selectivity of their localization and transgene expression within the lungs. As demonstrated above in Example 6, implanted cells were efficiently retained by the lungs.

The finding that most of the cells appeared to lodge within small pulmonary arterioles is consistent with the normal physiological role the lung plays as an anatomical filter, and thus it would be expected that relatively large particles such as resuspended cells would become lodged within the pulmonary microvasculature. However, this 'targeting' of cells to the pre-capillary resistance vessel bed in a highly selective manner may prove very useful in the treatment for certain pulmonary vascular disorders. The overexpression of a vasoactive gene at the distal arteriolar level could provide a highly localized effect in a vascular region critical in the control of pulmonary vascular resistance and could amplify the biological consequences of gene transfer. In fact, the localized reduction in RVSP seen in monocrotaline-treated animals receiving VEGF transfected cells, occurred without a corresponding decrease in systemic pressures, highlighting the specificity of this method of transfection. This approach may therefore offer significant advantages over other pulmonary selective gene transfer strategies such as endotracheal gene delivery, which results in predominantly bronchial overexpression, or catheter-based pulmonary vascular gene transfer, which produces diffuse macrovascular and systemic overexpression (see Rodman, D. M., H. San, R. Simari. D. Stephan, F. Tanner, Z. Yang, G. J. Nabel, E. G. Nabel. 1997. In vivo gene delivery to the pulmonary circulation in rats: transgene distribution and vascular inflammatory response. Am. J. Respir. Cell Mol. Bioi. 16:640-649; and Nabel. E. G., Z. Yang. D. Muller, A. E. Chang. X. Gao, L. Huang, K. J. Cho. G. J. Nabel, 1994. Safety and toxicity of catheter gene delivery to the pulmonary vasculature in a patient with metastatic melanoma. Hum. Gene Ther. 5:1089-1094).

This significant effect occurred despite an overall relatively low mass of organ-specific transfection, and was likely due to the fact that the transfected cells were targeted, based on their size, to the precapillary pulmonary resistance vessels which play a critical role in controlling pulmonary pressure. This method of pulmonary vascular gene transfer may have benefits over existing techniques by minimizing the overall "load" of foreign transgene that is delivered to the body and may thereby theoretically reduce the incidence of undesired side-effects.

EXAMPLE 14—EX VIVO SMOOTH MUSCLE CELL TRANSFECTION WITH Prostacyclin Synthase

Endothelial cell (EC) injury and dysfunction is believed to be an early event in PPH. Activation of endothelial cells has been found in diverse animal models of PH, including the rat chronic hypoxia and monocrotaline (MCT) models, as well PH induced by endotoxin, diaphragmatic hernia, or air-induced chronic pulmonary hypertension. EC dysfunction may in turn give rise to an imbalance of vasodilatory and vasoconstrictive agents. An altered ratio of thromboxane to prostaglandin and increased plasma endothelin-1 (ET-1) levels have all been reported in PPH. It is well recognized that there is a pathological remodeling of the pulmonary vasculature, characterized by intimal fibrosis, medial hypertrophy, and adventitial proliferation in late stage. Administration of $PGI_2$ analogues has been shown to result in the effective treatment of PPH in a number of clinical studies. Therefore, the rate limiting enzyme in the pathway for $PGI_2$ biosynthesis, prostaglandin I synthase (PGIS) is attractive target for cell-based gene therapy.

PGIS Gene Therapy in Experimental PH:

Prostacyclin synthase (PGIS), is a key enzyme involved in the production of prostacyclin, catalyzing the conversion of $PGH_2$ to $PGI_2$ (prostacyclin), a potent vessel dilator and cell growth inhibitor. This enzyme has also been shown to be downregulated in patients with severe PH. Experiments in PH animal models have demonstrated that PGIS can protect against the development PH, and slow its progression, suggesting that PGIS is a promising agent for treatment of pulmonary hypertension. Clinical studies using intravenous infusion (Fiolan), subcutaneous injection (Remodulin) or inhalation (Iloprost) have all reported benefit in patients with PAH.

The objective was to clone the full-length human PGIS eDNA and test its production activity.

Cloning and Verification of Activity of hPGIS:

RT-PCR was used to amplify the hPGIS eDNA from a human smooth muscle library. Primers QW9 and QW18 were designed to yield a full-length eDNA product, with an expected size of 1.5 kb (see FIG. 10), which corresponds to the size of hPGIS eDNA. Primers QW18 and QW9, inner primers, are used for the second-stage of PCR to amplify hPGIS eDNA.

QW9: 5'-CGA GCA CGT GGATCC ATC-3' (SEQ ID. NO. 13; antisense or PGIS eDNA, position 1532-1515; Tm=58 (BamH I site underlined)

QW18: 5'-CAT GGATCC GCG ATG GCT TGG GCC-3' (SEQ ID. NO. 14; sense, for cloning hPGIS eDNA, position −5-12; Tm=60) (BamH I site underlined)

Figure 10:
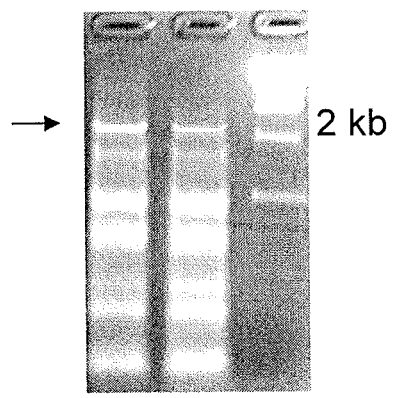
FIG. 10 is a gel showing a band of 1.5 kb (arrowhead: lanes 1 and 2).

FIG. 10 shows a band of 1.5 kb (arrowhead) was amplified (lanes 1 and 2). Lane 3 is a DNA size marker.

The 1.5 kb fragment was isolated and cloned into the pVAX1 vector. The resulting plasmid grown in competent *E. Coli* and purified by Maxiprep. The insert was released by restriction enzyme digestion and sequenced. One clone was shown to be 100% homologous with hPGIS with the kozak sequence immediately upstream of the start codon (ATG), and a stop codon at position 1500. Transfection of hPGIS eDNA in COS-1 cells: The hPGIS eDNA was successfully expressed in COS-1 cells with a molecular weight of about 50 kD. Biological activity of hPGIS: 6-keto PGF1 alpha, the stable metabolite of $PGI_2$, was detected by ELISA in conditioned medium of human SMCs transfected with hPGIS in two different experiments (see table). In both assays, transfected cells produced about 2-3-fold greater levels of PGI2 than control (mock) transfected cells.

6-keto PGF2-alpha levels in HASMCs in 2% FCS (pg/ml)

| N | pVAX-1 | pVAX-hPGIS |
|---|--------|------------|
| 4 h | 772 | 1533 |
| 8 h | 1782 | 3778 |

6 keto PGF2-a levels in HASMCs in 2% FCS (pg/ml)

EXAMPLE 15—MONOCROTALINE STUDIES WITH SMOOTH MUSCLE CELLS Transfected with PGIS

The objective was to test the efficacy of cell-based gene therapy with human PGIS in the rat MGT model in comparison with eNOS and VEGF.

Figure 11:
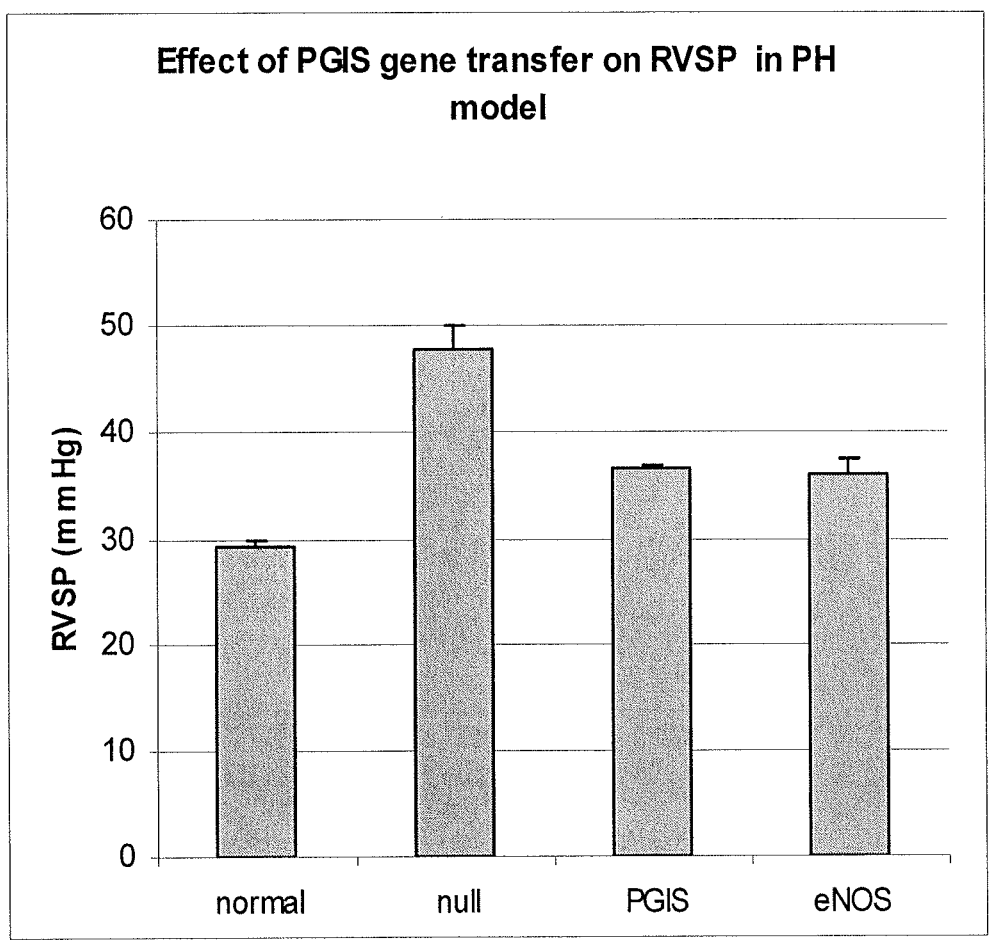
FIG. 11 is a bar graph showing cell-based gene transfer using PGIS and eNOS in experimental pulmonary hypertension.
Figure 12:
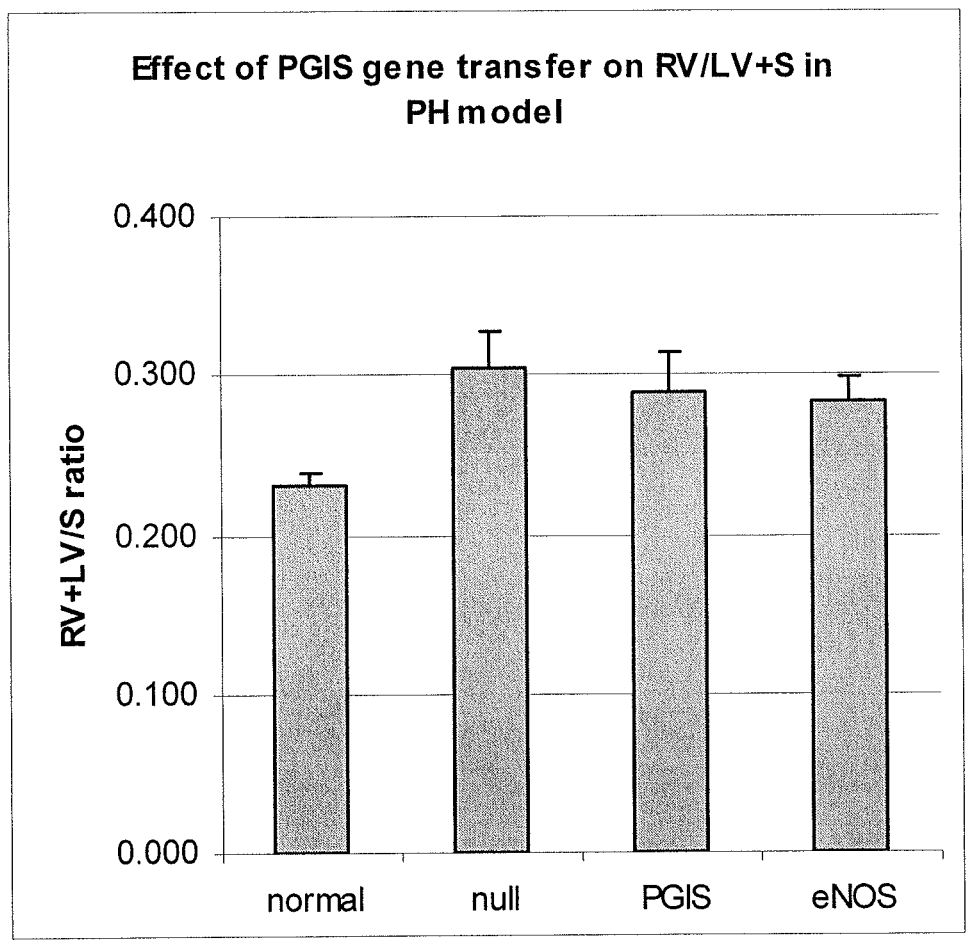
FIG. 12 is a bar graph showing cell-based gene transfer using PGIS and eNOS in experimental pulmonary hypertension.

FIGS. 11 and 12 show cell-based gene transfer using PGIS in experimental pulmonary hypertension (prevention protocol).

An experiment was completed testing the effect of cell based gene therapy using hPGIS (n=6) and eNOS (n=6) compared with null transfected animals (n=7). Gene therapy was given together with MGT (70 mg/kg) and all animals received a total of 1.5 million cells in 3 divided doses. Unfortunately, the mortality rate was higher than expected in the PGIS group likely due to biological variation in the sensitivity of this batch of rats (2/6 for PGIS: 0/6 for eNOS and 0/7 for null). The hemodynamic data for animals surviving until end-study are presented in FIGS. 11 and 12. Animals receiving MGT together with null transfected fibroblasts (FBs) exhibited elevated RVSP, indicative of PH (47.8±2.2 mmHg). In the MCT treated rats which received 3 doses of PGIS transfected FBs, RVSP was reduced to 36.6±0.263 mmHg, and the benefit appeared similar in this series to rats treated with eNOS gene transfer. The RV/LV was 0.3 in MCT treated group, compared to 0.28 in group received three dosing of PGIS (RV/LV in normal rat is 0.23) (see FIG. 12).

Conclusions:

PGIS gene transfer may improve pulmonary hemodynamics in experimental PH to a degree similar to that seen with eNOS.

EXAMPLE 16—CELL BASED GENE THERAPY IN ESTABLISHED PULMONARY Hypertension Using Reversal Protocol The present inventor has demonstrated that cell-based gene therapy can prevent monocrotaline (MGT) induced pulmonary hypertension using the VEGF and eNOS transgene. The efficacy cell-based gene therapy was assessed in experimental models of established PH, so that the ability of this treatment to reverse structural and functional abnormalities of the pulmonary circulation could be shown.

Objectives:

To study the efficacy of cell-based gene transfer to reverse established PH in the MGT model.

Methods and Results:

These studies employed a modification of the standard MGT experimental protocol previously validated with experiments using eNOS gene transfer and VEGF gene transfer in examples set out above. Briefly, MGT was injected as usual, and at day 21 post MGT the animals were then anaesthetized and RVSP was recorded. Rats are then randomly assigned as normal (n=40), to receive null-transfected (pcDNA, n=32) or cells transfected with an active transgene (VEGF, n=20: eNOS, n=36), and then survived until day 35, at which time RVSP is remeasured, and the rats are sacrificed morphometric, functional and molecular assessments. In the present studies, human VEGF165 was used since it was hypothesized that reversal of PH must involve regeneration of occluded pulmonary arterioles. Again, animals were treated with a total of 1.5 million cells, delivered in 3 divided doses.

Figure 13:
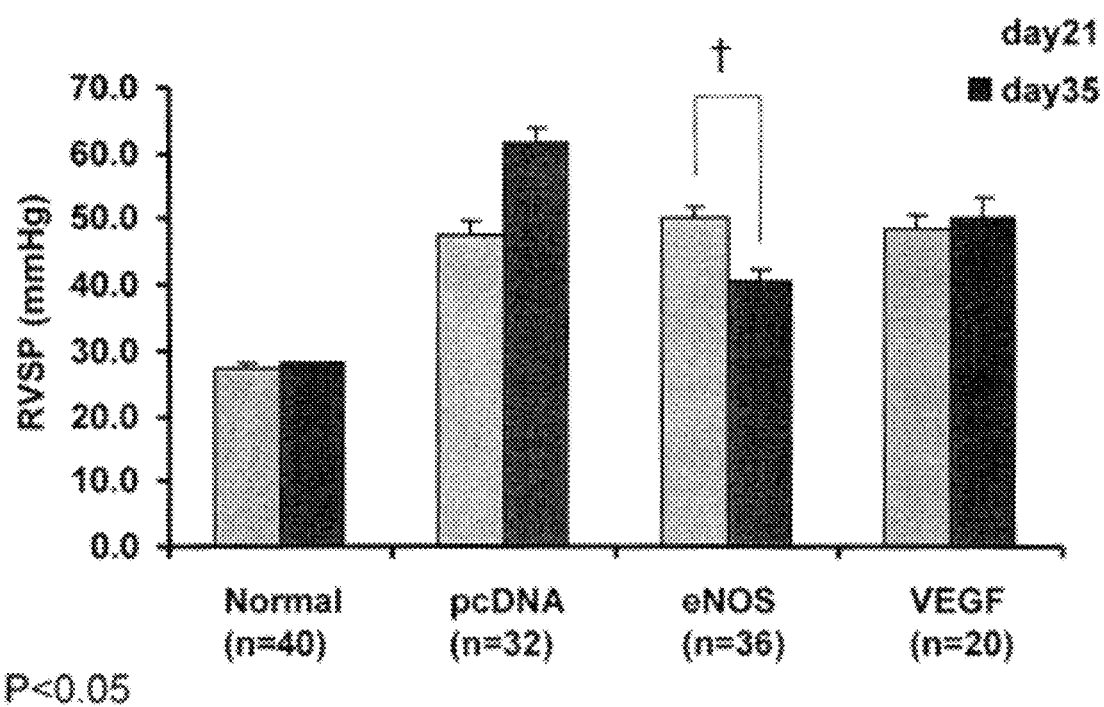
FIG. 13 is a bar graph showing cell-based gene transfer using VEGF or eNOS in experimental pulmonary hypertension.

As shown in FIG. 13, at day 21 (i.e. prior to gene therapy). RVSP was similarly elevated in the control (null) and VEGF and eNOS transfected groups (approximately 40 mm Hg). In the MCT treated with null transfected FBs, there was a further significant increase in RVSP at day 35 (51.6±4 mmHg, p<0.05), indicating progression of PH. In the MGT-treated rats receiving VEGF transfected FBs. RVSP demonstrate a trend towards reduction as compared to the null transfected FBs. In the MGT-treated rats receiving eNOS transfected FBs, RVSP demonstrate a trend towards significant reduction (p<0.05 vs. normal). RV/LV was increased in the MCT-null vector group (0.29), however this was reduced to 0.27 in the group receiving VEGF (RV/LV in normal rat is 0.25). The weight gain is 84 g in normal group and reduced to 48 g in MCT treated group. Weight gain tended to increase to 58 gin the VEGF treated group.

Conclusions:

In this series, cell-based gene therapy VEGF prevented further progression of established PH. Cell based GT with NOS effectively reversed hemodynamic abnormalities in established PH and resulted in the regeneration of continuity of the pulmonary microcirculation.

EXAMPLE 17—OPTIMIZATION OF NONVIRAL TRANSFECTION EFFICIENCY FOR Fibroblasts

Figure 14:
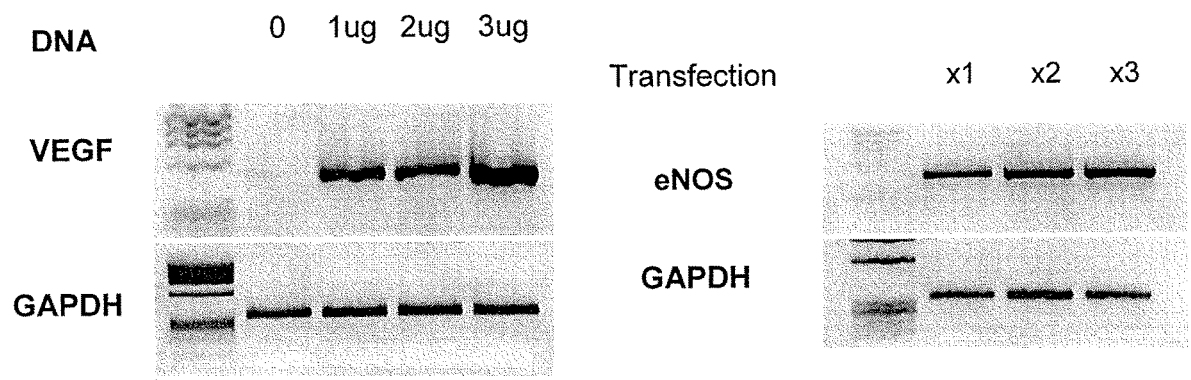
FIG. 14 is a gel showing the results of multiple transfections using the eDNA for eNOS.
Figure 15:
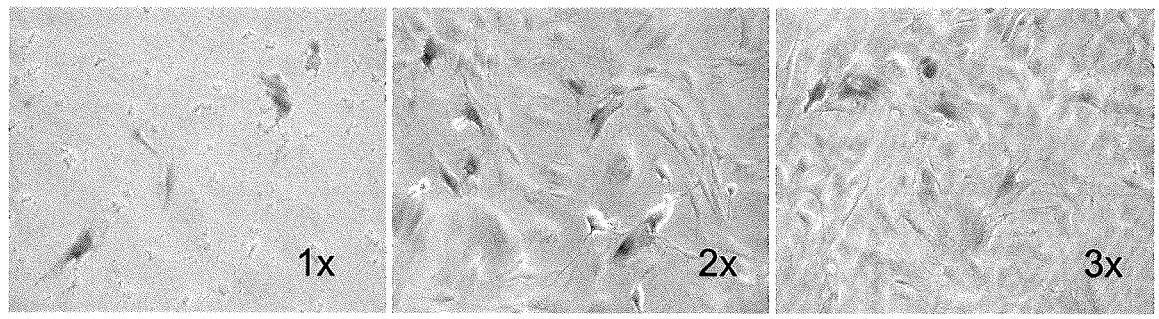
FIG. 15 are photographs comparing a single transfection to a double protocol.

This Example sets out the utility of sequential transfection with b-cationic proteins (Superfect).
Objective:
To establish a standard operating protocol (SOP) for optimal transient transfection of rat and human FBs using nonviral methods of gene transfer and sequential gene transfer.
Methodology:
i) Cell preparation: Rat FBs were plated 12-24 hours prior to transfection resulting in a confluence of 60-80%. For 35 mm plates used for practice transfection that is 50.000 cells, T-75 is 1,000,000 cells. Growths conditions are DMEM (Gibco, #119950065) containing 15% serum (Sigma. F-2442) at 37° C. in 5% $CO_2$
ii) Transfection protocol: the following were mixed in a 50 ml Falcon tube (falcon, cat. #352070):
a) 500 ul DMEM medium, no serum or anti-biotic
b) 7 ug plasmid DNA, i.e. vector plus insert.
c) 50 ul superfect (Qiagen, cat #301307, 3 mg/ml)
The mixture was then added to each T-75 flask (superfect/DNA complex).
Superfect/DNA complex is incubated for 5-10 minutes upon which added 5 ml of DMEM containing 15% serum and added to the cell population for 5-8 hours.
In "double transfection" protocols, cells that have been already transfected, are re-plated as described above and re-transfected 48 hours after the first transfection procedure. This time interval has been determine to be optimal in studies (data not shown). In the "triple transfection" protocol, a third transfection is performed again after a 48 hour "recovery interval". This approach has the theoretical advantage of allowing transfection of a separate population of cells from those susceptible in the first transfection, while avoiding significant toxicity which would otherwise occur.
Measurements:
To determine the cell number and DNA/superfect ratios that give the best results, two methods have been selected:
i) RT-PCR, genes selected for measurement,
ii) VEGF165, B-gal, eNOS and the house keeping gene GAPDH.
Primers for these genes are:

```
Exogenous VEGF:
VHF1
                                        (SEQ ID No 15)
5'-cgc tac tgg ctt atc gaa att aat acg act cac, VHF2
                                        (SEQ ID No 16)
5'-ggc ctt ggt gag gtt tga tcc gca taa t;

exogenous eNOS:
VHF1, NHR ®
                                        (SEQ ID No 17)
5'-cgc tct ccc taa gct ggt agg tgc c;

β-gal:
β-gal (1)
                                        (SEQ ID No 18)
5'- tgt acc cgc ggc cgc aat tcc, β-gal (2)
                                        (SEQ ID No 19)
5'-att cgc gct tgg cct tcc tgt agc c;

GAPDH:
GDH1
                                        (SEQ ID No 20)
5' ctc taa ggc tgt ggg caa ggt cat, GDH2
                                        (SEQ ID No 21)
5' gag atc cac cac cct gtt gct gta.
``` ii) β-gal staining was used to determine best results for percent of cells transfected.
Results:
FIG. 14 shows the results of multiple transfections using the cDNA for eNOS.
There is a near linear increase in transfection efficiency with each sequential transfection, whereas cell viability is not reduced.
In FIG. 14, the hVEGF expression by PCR is shown after a single transfection protocol, contrasting the effect of different superfect to DNA ratios on transfection efficiency: lane 1, non-transfected cells: lane 2, 1 μg DNA: 10 μl superfect: lane 3, 2 μg DNA: 10 μl superfect; and finally lane 4, 3 μg DNA: 10 μl superfect. Keeping the superfect constant and increasing the amount of DNA appears to yield a larger signal.
β-gal staining is shown in FIG. 15 comparing a single transfection to a double protocol. Double transfection results in about twice the number of cells staining positive with LacZ.
Conclusions:
Sequential transfection using ?-cationic proteins (Superfect) resulted in a near linear increase in transfection efficiency, measured both by number of cells expressing a reporter gene (LacZ) and amount of plasmid DNA (quantitative PCR), without an increase in toxicity.

EXAMPLE 18-CELL-BASED GENE TRANSFER FOR CYSTIC

Fibrosis Introduction and Rationale:
Cystic fibrosis is an autosomal recessive disorder caused by the production of a defective chloride channel, CFTR, primarily expressed in epithelial cells and submucosal gland cells, and affecting multiple organs. This genetic defect impairs transepithelial salt transport, mucous viscosity, and ion flux in organs such as the salivary glands, pancreas, gastrointestinal tract, reproductive tract, and most importantly, the lungs. The defect in the pulmonary epithelium results in highly viscous mucous, causing plugging of the tracheobronchial tree, thus interfering with normal respiratory function and increasing susceptibility to lung infections.
Our laboratory has developed a novel and highly selective method for targeting gene transfer to the pulmonary vasculature using transfected smooth muscle cells or fibroblasts injected via the systemic circulation. We have shown that these cells are efficiently filtered by the distal arteriolar (pre-capillary) bed and rapidly translocate through the endothelial basement membrane to take up residence within the perivascular space. Therefore, it appears that these cells are able to recognize their appropriate location within the lung tissue.
The present inventor has found that pulmonary cell types are able to "home" to their appropriate tissue locations, possibly by recognizing specific matrix components through unique integrin interactions. In the present research project, it is shown that injected pulmonary alveolar type II cells can translocate through the vascular and epithelial basement membranes and localize to the luminal side of the epithelial basement membrane. This would then enables transvascular delivery of genetically engineered epithelial cells useful in treating genetic disorders of airway function, such as cystic fibrosis, which can then be tested in a CFTR knockout mouse model.

Hypothesis:

Isolated epithelial cells from the lungs of syngeneic rats will migrate to a bronchial/bronchiolar location of normal rats when injected into the pulmonary circulation.

Objectives:

1. To establish a primary cell culture of lung epithelial cells obtained from syngeneic Fisher-344 rats.
2. To follow the in vivo migration of transplanted, CMTMR-labeled epithelial cells upon delivery into the pulmonary bed through the right external jugular vein. The presence of these cells and their location will be evaluated over a period of one week, with rats sacrificed at 1, 2, 3, and 7 days.
3. To assess the ability of transfected epithelial cells to express a reporter transgene in situ after grafting into the tracheobronchial system.

Results:

Transplanted epithelial cells can indeed migrate to their bronchioalveolar location.

Figure 16:
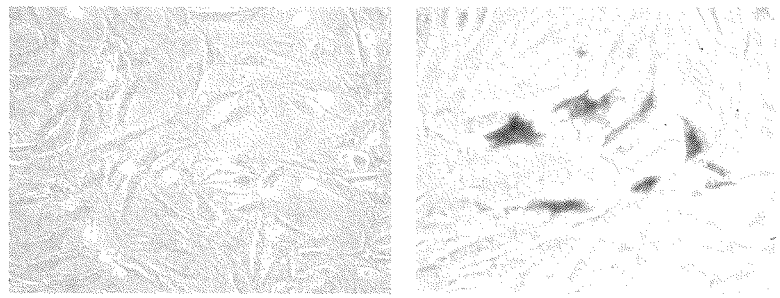
FIG. 16 is a photograph which indicates the morphology of isolated lung epithelial cells in primary cell culture, 5 days after isolation.
Figure 17:
FIG. 17 is a photograph which shows fluorescent microscopy showing purity of isolated lung epithelial cells.

The results are summarized in the FIG. 16 which indicates the morphology of isolated lung epithelial cells in primary cell culture, 5 days after isolation. Right-hand panel shows transfection of the isolated lung "epithelial" cells with β-Gal. FIG. 17 shows fluorescent microscopy showing purity of isolated lung epithelial cells.

Green indicates positive staining for the type II epithelial marker SPAn; Blue represents nuclear staining with Dapi.

Unlike traditional virally-based gene therapy, a cell-based gene therapy approach is less likely to provoke an immunological response and lowers/eliminates the risk of insertional mutagenesis.

EXAMPLE 19-CELL-BASED GENE TRANSFER IN ADULT RESPIRATORY Distress Syndrome (ARDS)

The angiopoietin system appears to play a critical role in the maintenance of normal endothelial homeostasis, in part by reducing endothelial permeability and preventing extravasation of plasma proteins. Acute lung injury caused by a wide variety of insults (including ventilation-induced lung injury) results in increased pulmonary capillary permeability and pulmonary edema without any increase in capillary or left atrial pressures: so called "low pressure edema" or ARDS. This is the single most common pulmonary complication of ICU patients, and accounts for a tremendous burden of morbidity and mortality. Angiopoietin-1 is a recently identified ligand of the endothelium-specific tyrosine kinase receptor Tie-2. It is involved in the maturation of blood vessel and is very potent in reducing the hyper-permeability response to inflammatory stimuli.

Cell based gene transfer with Angiopoietin-1 (Ang-1) reduced lung edema in an animal model of ARDS. The Angiopoietin-1 gene was introduced into rats prior to exposure to either LPS (which serves as model for sepsis) or high volume mechanical ventilation. Both of these stimulations would normally be expected to induce pulmonary edema. It is involved in the angiogenic phase of embryonic vascular development with major defects in the interaction of endothelial cells, with the surrounding mesenchymal cells and extracellular matrix evident in Ang1 knockout mice.

Objectives:

The main objectives were (1) to show that transfer of a gene (angiopoietin-1) using a cell-based transfer system could reduce the formation of pulmonary edema that occurs with the systemic inflammation response induced by administration of mechanical ventilation and (2) to show that this method of gene delivery was suitable to treat disorders which diffusely affect the alveoli and/or capillaries in the lung.

Methods:

Preparation of the Cells Transfected with Angiopoeitin 1 Gene:

21 day old Fisher 344 rats were sacrificed by overdose of IP injection of pentobarbital (50 mg). The pulmonary artery was dissected out, and smooth muscle cells were cultured and transfected with the gene following the established protocol.

Intravenous Delivery of Transfected Cells. Untransfected Cell or Normal Saline:

Fisher 344 rats (body weight 200-250 gram) were anesthetized with IP xylazine (5 mg/kg) and ketamine (70 mg/kg). A midline cervical incision was made after cleaning and shaving the area, and the common and external jugular veins identified. Animals were randomized to received Angiopoeitin 1, untransfected cell or normal saline. Using a 23-gauge needle, a 1 mm tube was introduced into the external jugular vein, and through this approximately 500000 cells transfected with the Angiopoeitin 1 gene, untransfected cell (pcDNA3.1) as a control group and 1 cc normal saline as a sham group were infused. The animals were allowed to recover for 24 hours.

Induction of Pulmonary Edema:

The rats were mechanically ventilated in order to stimulate pulmonary edema. The rats were anesthetized with ketamine (75 mg/kg) and xylazine (15 mg/kg). A mid-cervical incision was made, the trachea exposed and incised. A 16 G catheter was inserted into the trachea, through which the animal was ventilated. The tail vein was cannulated, and an IV infusion of ketamine (20 mg/hr) xylazine (2 mg/hr) and the muscle relaxant, pancuronium (0.2 mg/hr) was commenced. The pancuronium is necessary in order to suppress any spontaneous respiratory effort that might interfere with the function of the ventilator. Mechanical ventilation was commenced, using a rodent ventilator, with room air, tidal volume 20 ml/kg, zero positive end expiratory pressure and respiration rate 27/bpm. The carotid artery was cannulated with 24 G angiocatheter and connected to BP monitor with a three-way stock. We recorded the mean artery pressure, peak airway pressure, plateau airway pressure and measured the artery blood gas at baseline, 0.5, 1, 2 and 3 hour during the ventilation. After 3 hours ventilation, the animals were sacrificed by IV injection of pentobarbital, and the lungs processed as above to obtain the wet/dry weight ratio.

Results (A) Healthy Lung Model:

|  | Baseline | 1 hour | 2 hour | 3 hour |
| --- | --- | --- | --- | --- |
| Ang | 112 | 121 | 112 | 110 |
| Con (pc DNA) | 97.66667 | 103.3333 | 93 | 86.66667 |

*Mean artery pressure (mmHg) change during the ventilation

-continued

|  | Baseline | 1 hour | 2 hour | 3 hour |
|---|---|---|---|---|
| Ang | 21.16667 | 19.93333 | 21.16667 | 21.6 |
| Cont (pc DNA) | 22.26667 | 22.86667 | 22.66667 | 22.06667 |

*Peak airway pressure (cm H20) change during the ventilation

|  | Baseline | 1 hour | 2 hour | 3 hour |
|---|---|---|---|---|
| Ang | 17.33333 | 16.66667 | 17.83333 | 18 |
| Con (pc DNA) | 18.33333 | 18.83333 | 18.83333 | 18.16667 |

*Plateau airway pressure (cm H20) change during the ventilation

|  | Body Weight (gm) | Wet Weight (gm) | Dry Weight (gm) | W/D Weight ratio (gm) |
|---|---|---|---|---|
| Ang | 240 | 1.029 | 0.222 | 4.635135 |
| Ang | 240 | 1.07 | 0.212 | 5.04717 |
| Ang | 227 | 1.077 | 0.215 | 5.009302 |
| Mean Value | 235.6667 | 1.058667 | 0.216333 | 4.897202 |
| Con (pc DNA) | 243 | 1.115 | 0.226 | 4.933628 |
| Con (pc DNA) | 236 | 1.226 | 0.217 | 5.64977 |
| Con (pc DNA) | 235 | 1.268 | 0.225 | 5.635556 |
| Mean Value | 238 | 1.203 | 0.222667 | 5.406318 | n = 3 in both group
no significant difference except trend in W/D ratio in both group (p value = 0.1329)

Figure 18:
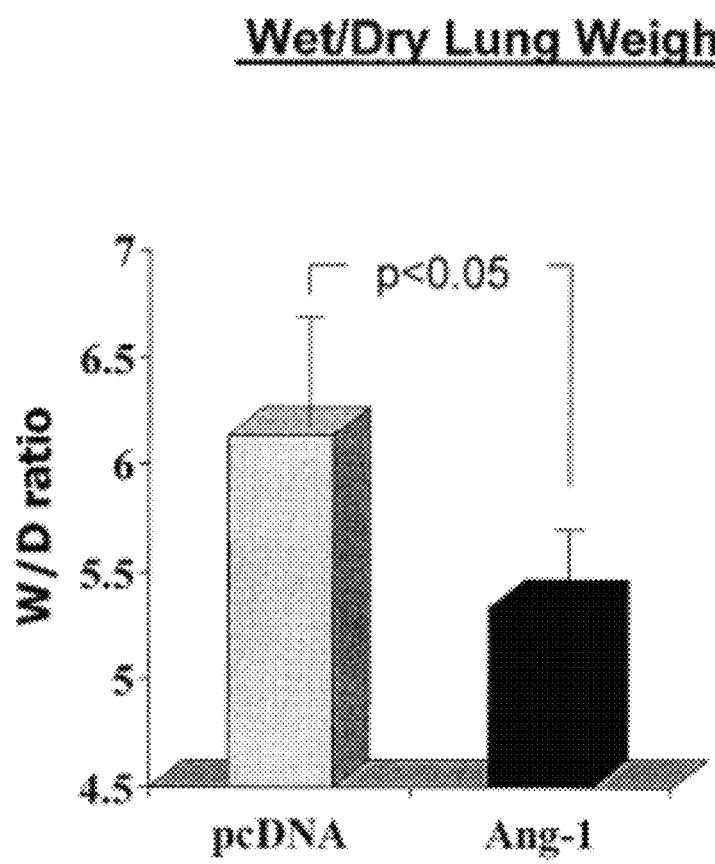
FIG. 18 is a bar graph showing decrease in Wet/Dry lung weight by use of gene therapy.
Figure 19:
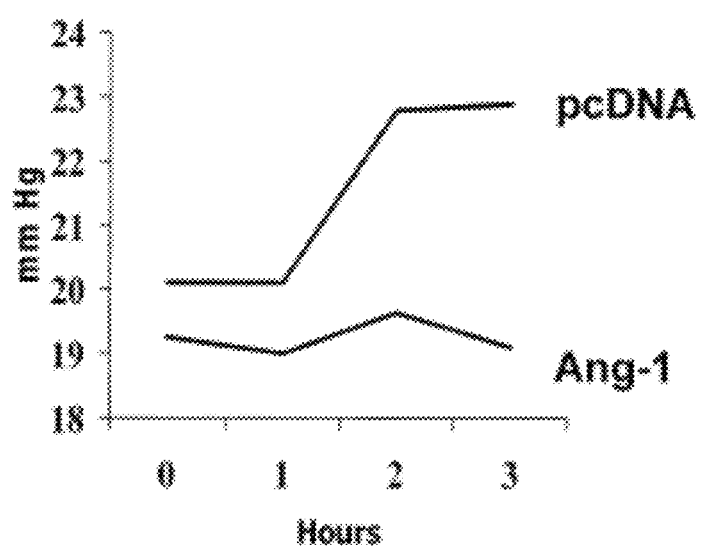
FIG. 19 is a bar graph showing decrease in peak airway pressure by use of gene therapy.
Figure 20:
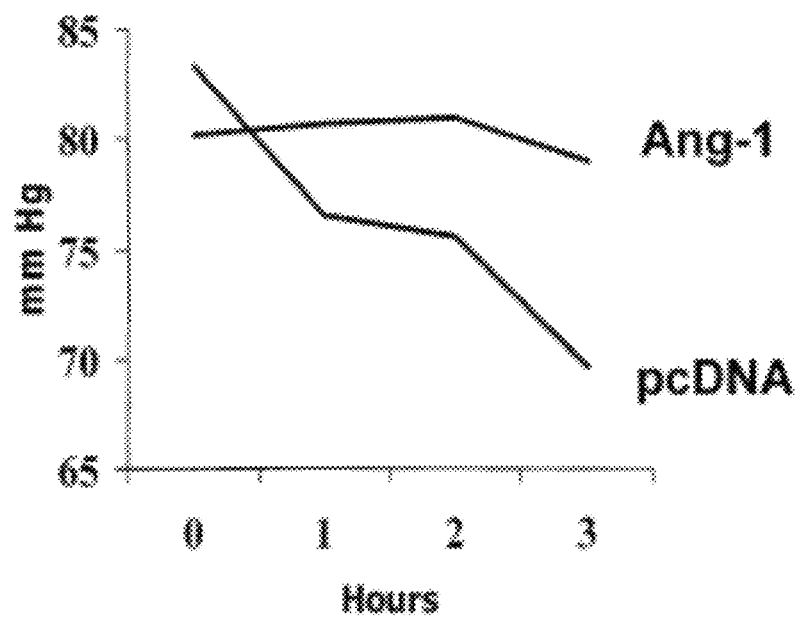
FIG. 20 is a bar graph showing maintenance of partial oxygen pressure as compared to the null vector, by use of gene therapy.

FIGS. 18 to 20 show a summary of the results of Ang-1 gene therapy for ARDS using the ventilator induced lung injury model. FIG. 18 shows a significant decrease in Wet/Dry lung weight by use of gene therapy. FIG. 19 shows a significant decrease in peak airway pressure by use of gene therapy. FIG. 20 shows maintenance of partial oxygen pressure as compared to the null vector, by use of gene therapy.

As shown in the tables above, and in FIGS. 18 to 20, there was reduced lung wet to dry weight ration in animals receiving Ang-1 gene therapy, consistent with a reduction in permeability. Thus this treatment approach reduces pulmonary edema and capillary permeability in this model of ARDS.

EXAMPLE 20—CELL BASED GENE THERAPY IN ESTABLISHED Pulmonary Hypertension Using Multiple Injections The objective was to test the efficacy of multiple injections of cell-based gene therapy with eNOS.

An experiment was completed testing the effect of cell based gene therapy using eNOS (n=6) compared with null transfected animals (n=11) and normal animals (n=5). Gene therapy was given together with MCT (70 mg/kg) and all animals received a total of 1.5 million cells in 3 divided doses.

Figure 21:
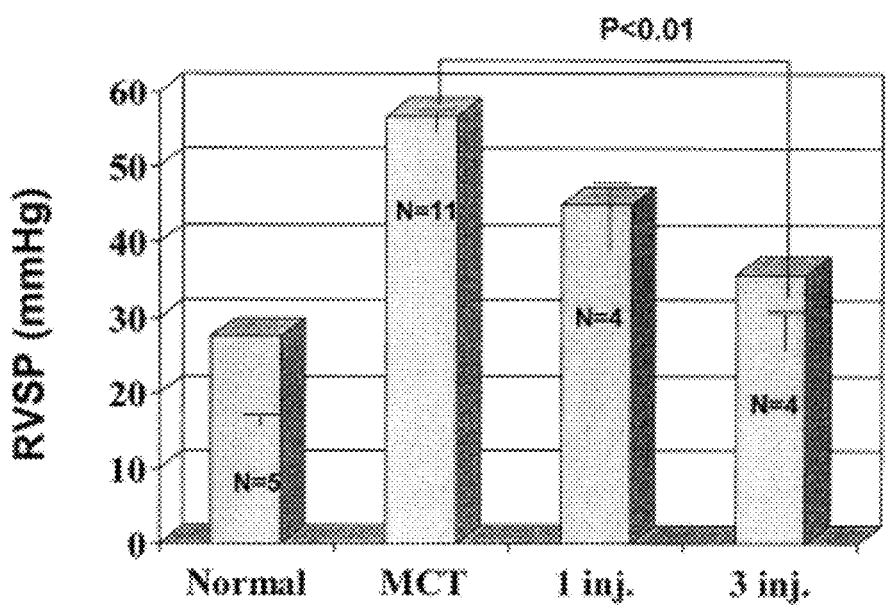
FIG. 21 is a bar graph showing that dosing cell-based endothelial NOS gene transfer inhibits MCT-induced PH and the effect of multiple injections, measured by RVSP.
Figure 22:
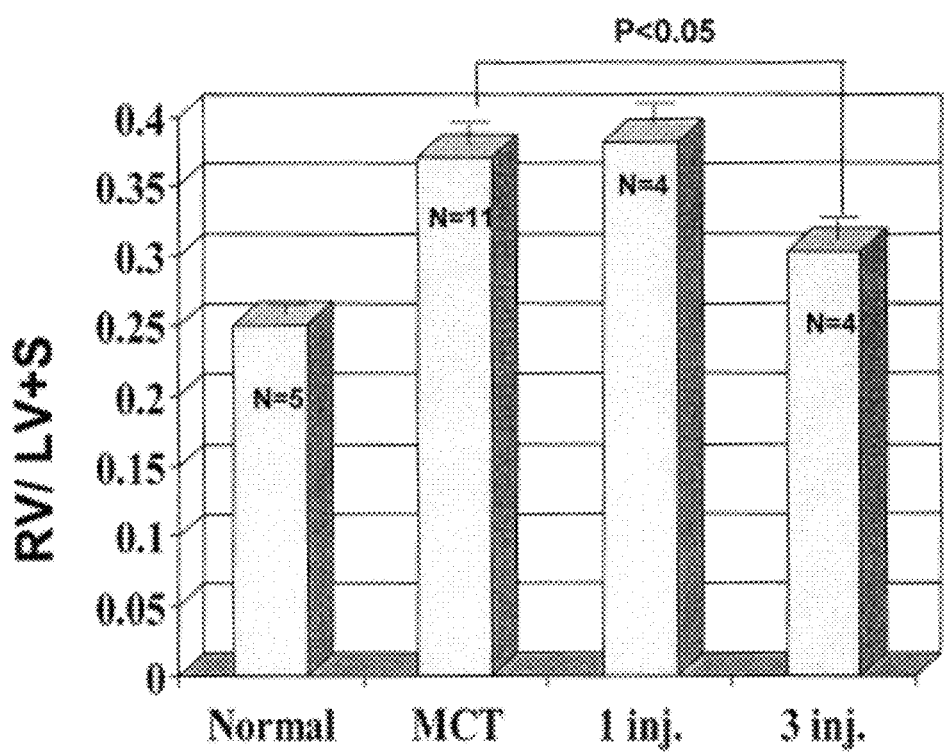
FIG. 22 is a bar graph showing that dosing cell-based endothelial NOS gene transfer inhibits MGT-induced PH and the effect of multiple injections, measured by RV/LV+S.
Figure 23:
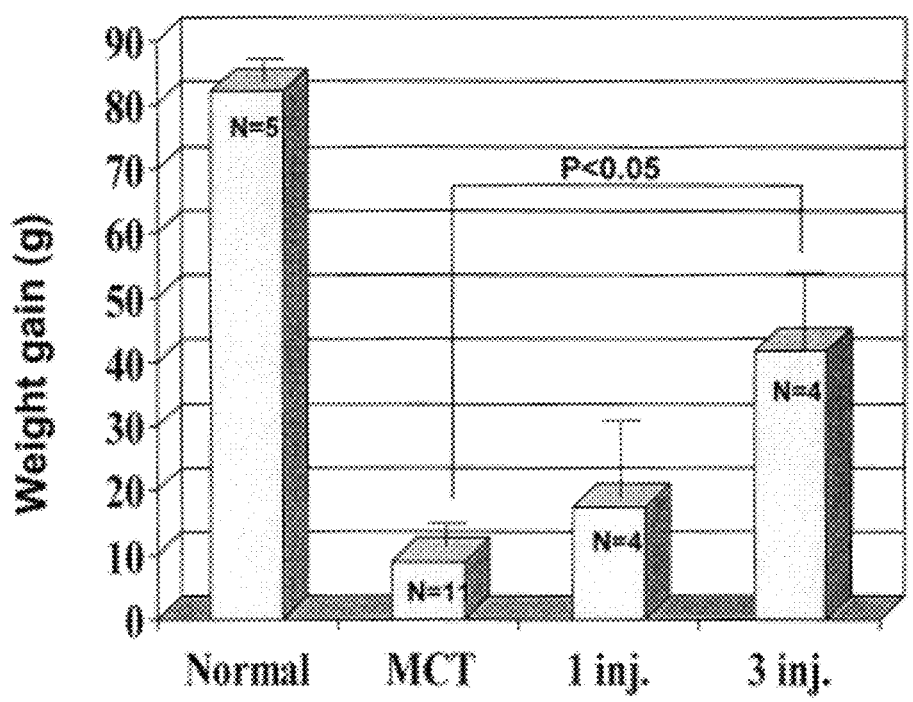
FIG. 23 is a bar graph showing that dosing cell-based endothelial NOS gene transfer inhibits MGT-induced PH and the effect of multiple injections, measured by weight gain.

FIGS. 21 to 23 show that dosing cell-based endothelial NOS gene transfer inhibits MCT-induced PH and that the effect of multiple dosing is greater than the effect of single dosing, whether measured by RVSP (FIG. 21), RV/LV+S (FIG. 22), or weight gain (FIG. 23). These results indicate that multiple injections of eNOS-transfected cells show a dose-dependent reduction in pulmonary blood pressure, preventing hemodynamic abnormalities in PH model.

Conclusions:

eNOS gene transfer may improve pulmonary hemodynamics in experimental PH in both single and multiple dosage regimens.

EXAMPLE 21—EFFECT OF ELPC TRANSPLANTATION AND E-NOS-TRANSDUCED ELPC Transplantation of Pulmonary Arterial Hypertension (PAH)

Objectives

The objective was to test the efficacy of ELPC cells, and cell-based gene transfer using eNOS-transduced ELPC cells, to reverse established PH and to prevent PH in the MCT model.

Methods:

(a) Isolation and Culture of ELPC Cells

Skin biopsies were obtained from 21-day-old Fisher-344 rats (Charles River Co. St Constant, Quebec, Canada), and FBs were cultured using an explant technique. Cells were grown in Dulbecco Modified Eagle Media (DMEM) with 10% fetal bovine serum (FBS) and 2% penicillin/streptomycin (50 U/mL penicillin G; 50 µg/mL streptomycin) in a humidified incubator (20% $O_2$, 5% $CO_2$ at 37° C.), and used between passages 2 and 9.

Bone marrow (BM) was aspirated from the femurs of 21-day-old syngeneic Fisher-344 rats. Mononuclear cells (MNCs) were isolated by density gradient (Ficoll-Paque. Amersham) centrifugation at 400 g for 30 minutes. BM-MNCs were resuspended in differential endothelial cell culture medium (EBM-2, Cambrex) with 10% FBS, 50 U/mL penicillin, 50 µg/mL streptomycin, and 2 mmol/L L-glutamine (Invitrogen), plated on gelatin-coated tissue culture flasks and incubated at 3 rC with 5% $CO_2$ for 7 to 10 days, to produce endothelial-like progenitor cells (ELPCs).

For immunocytochemistry, differentiated MNCs were subcultured on 4-well chamber slides (BD Bioscience), and fixed in 2% paraformaldehyde for 10 minutes. Cells were incubated overnight at 4° C. with the following primary antibodies: rabbit anti-human Flk-1 (VEGF-R2; Alpha Diagnostic Inc; 1:200); mouse anti-human Tie-2 (Upstate Biotechnology Inc; 1:50), or rabbit anti-human von Willebrand factor (vWF. DAKO; 1:1000). Rabbit anti-mouse or goat anti-rabbit F(ab')2 (Vector; 1:150) conjugated with FITC were used as secondary antibodies, as appropriate. Surface lectin staining was performed using fluorescently labeled UEA-1 Lectin (Sigma) at 10 ug/ml. As well, the ability for live cells to take up fluorescently labeled acetylated-LDL (Dii-Ac-LDL; Molecular Probes) was assessed by incubation with Di-ac-LDL (10 ug/ml) for 4 hours at 37° C. ToPro3 (1:1000; Molecular Probes) was used for nuclear counterstaining and images were captured by confocal microscopy (BioRad Radiance).

(b) Transduction

The full-length coding sequence of human eNOS was generated as previously described, and ELPCs were transduced with human eNOS cloned into the pVax-1 plasmid vector using electroporation (MaxCyte) according to a protocol optimized by the manufacturer. The empty (null) pcDNA 3.1 vector was used as a control. After transfection, cells were replated and cultured for 24 hours, trypsinized (0.25% trypsin, 1% EDTA), washed, and resuspended in phosphate buffered saline (PBS), and then divided into aliquots of 500 000 cells/ml for injection. Western blot analysis revealed that electroporation resulted in peak human transgene expression at 72 hours, persisting for more than 1 week (data not shown).

(c) Animal Models of PAH

Two complementary models of MCT-induced PAH were used in this study, to examine the effect of ELPC delivery on both prevention and reversal. All animal studies were conducted under protocols approved by the animal care committee at St Michael's Hospital and in accordance with guidelines from the Canadian Council of Animal Care. In the prevention protocol, cell therapy was delivered 3 days after MGT injection and rats were followed for 21 days; control groups were compared with the ELPC-treated group. Persistence of therapeutic effect was investigated in separate groups of animals survived for longer periods (dotted lines). For reversal studies, rats were randomized to treatment groups at 21 days after MCT injection and initial hemodynamic measurements were made to confirm establishment of pulmonary arterial hypertension and to allow for paired comparisons within groups at end study 14 days later.

(d) Prevention Protocol

Cells were delivered via central venous injection 3 days after MGT, and the animals were euthanized at 21 days. Six-week-old Fisher-344 rats (160 to 180 g) were given intraperitoneal (IP) injections of saline (control group, n=13) or 75 mg/kg of MCT (Aldrich Chemical Co). Three days later, MGT-treated animals were assigned to three experimental groups: no cell injection (MGT alone, n=15), or 1 million ELPCs (n=23) or FBs (n=10). For cell delivery, rats were anesthetized with an IP injection of xylazine (4.6 mg/kg) and ketamine (7 mg/kg), the left cervical area was shaved and cleaned with 70% ethanol, and the external jugular vein was catheterized with a polyethylene cannula flushed with heparinized saline (40 IU/ml). Twenty one days after MGT injection, the rats were reanesthetized, and a 3F Millar microtip catheter was inserted via the right external jugular vein and into the right ventricle to obtain measurements of right ventricular systolic pressure (RVSP; Biopac System, Acknowledge software). The animals were then euthanized and the hearts and lungs harvested. The ratio of right to left ventricular plus septal weight (RV/LV) was determined as described previously. The left lung was inflated with OCT (Tissue-Tek) and cut into pieces that were fixed in a 4% paraformaldehyde/0.1% glutaradehyde PBS solution for paraffin embedding and sectioning. The right lung was snap frozen in liquid nitrogen.

In a separate experiment, animals were treated with MCT and randomized at 3 days to receive either no cells (saline, n=13) or ELPCs (n=12) as described above and then followed for longer periods of time to establish the persistence of any therapeutic effect. The animals were monitored daily by experienced animal care personnel in a blinded fashion and euthanized if predetermined criteria of significant morbidity were met (weight loss, hunched posture, poor coat appearance, conjunctival hemorrhage, and labored breathing). RVSP and RV/LV weight ratios were measured at the time of euthanasia as described above.

(e) Reversal Protocol

In the reversal model, rats were injected with saline (Control, n=12) or MGT, and 21 days later, baseline RVSP was recorded as earlier to confirm the presence of PAH. Thereafter, polyethylene catheters were inserted into the left external jugular vein and tunneled subcutaneously to the intrascapular region, exiting through a small incision, and sealed to the external environment with a removable plug. All incisions were closed with 3-0 interrupted absorbable sutures. Rats were randomized to receive saline (MCT alone), ELPCs alone, or ELPCs transduced with human eNOS (n=19 to 23/group). Cells were given in three sequential injections of $5\times10^5$ over 3 days through the indwelling catheter (total dose=$1.5\times10^6$ cells). After the final cell injection, the indwelling catheter was removed, the left external jugular vein was ligated, and animals were allowed to recover. Fourteen days later (35 days after MCT) RVSP was recorded, the animals were euthanized, and lung and heart tissues were collected for analyses as described.

(f) Fluorescent Microangiography

In a subset of animals, a catheter was inserted into the pulmonary artery immediately after euthanasia and the lungs flushed with heparinized PBS at 37° C., immediately followed by perfusion with a warmed (45° C.) solution of 1% low melting point agarose (Sigma) containing 0.2 μm yellow-green fluorescent microspheres (505/515 nm peak excitation and emission, Molecular Probes).

(g) Engraftment of ELPCs

In separate experiments, ELPCs were loaded with the vital cytoplasmic fluorescent label. CMTMR (Molecular Probes). Before transplantation, subconfluent cultures of ELPCs were incubated for 40 minutes with 10 μmol/L CMTMR, and $1\times10^6$ labelled cells were injected into the pulmonary circulation of normal rats at 3 or 21 days after MCT injection via the external jugular vein as described. Lungs or kidneys were harvested at various time points (10 minutes to 3 weeks) after cell delivery and examined by confocal fluorescent microscopy. Quantitation of cell number was performed. In some cases, the lungs were also subjected to fluorescent microangiography and confocal images were captured by optical sectioning as described.

(h) Arteriolar Muscularization

The degree of muscularization of small arterioles was assessed in 5 μm lung cryosections immunostained for von Willebrand factor (vWF) and a-smooth muscle actin (a-SM-actin) as described in the online data supplement.

(i) Statistical Analysis

Data was presented as mean±SEM. Differences between groups were assessed by using analysis of variance (ANOVA), followed by post hoc comparisons using an unpaired t test as appropriate. Differences within groups between the 21- and 35-day time points were assessed using a paired t test. Significance of differences for survival data were determined using the Kaplan-Meier analysis. A value of $P<0.05$ was considered statistically significant.

Results (a) In Vitro Characterization of ELPCs

Figure 24:
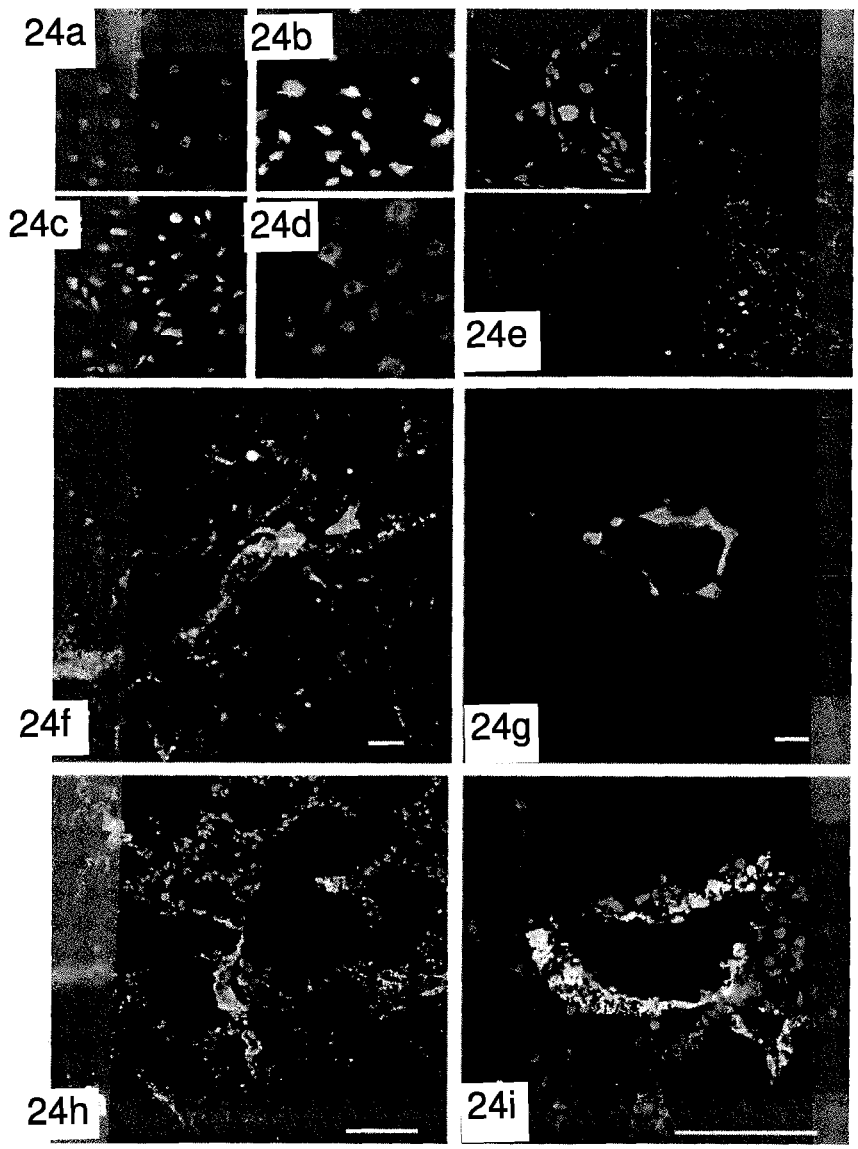
FIG. 24 (a-d) are a series of photographs of ELPC phenotype in vitro.

After 7 to 10 days of culture in endothelial growth medium. BM-MNCs demonstrated a cobblestone appearance typical for endothelial cells and exhibited positivity for a panel of EC markers, including Dil acLDL, UEA-1 lectin staining, and immunostaining for vWF, and Flk-1 varying from 65% to 83%. ELPC phenotype was characterized in vitro (FIG. 24, a through d) by assessing Di acetylated LDL uptake (a) and UEA-1 lectin surface staining (b), indirect immunofluorescence staining was performed to detect vWF (c) and Flk-1 (d) expression. Fluorescently labeled ELPCs were injected 3 days after MGT administration, and lungs were perfused with agarose containing fluorescent microspheres just before harvest. At 15 minutes after injection, cells were trapped within distal arterioles (FIG. 24, e). At later time points, injected cells were seen to engraft into the endothelial layer of distal precapillary arterioles as confirmed by fluorescent microangiography (FIG. 24 f). In some areas, complete luminal incorporation was observed (FIG. 24, g). Labeled ELPCs delivered 21 days after MGT appeared to be incorporating in precapillary and larger arterioles (FIGS. 24 h and i) (vWF immunostaining; calibration bars=50 μm).

(b) Engraftment of Fluorescently-Labeled ELPGs

GMTMR-labeled ELPCs were injected into the pulmonary circulation 3 days after administration of MCT. Fifteen minutes after delivery, labeled ELPGs were seen distributed throughout the lung (FIG. 24(e) insert), nearly exclusively within small precapillary arterioles. Seven days after cell injection, fluorescently-tagged ELPGs were seen surrounding and engrafting distal arterioles (FIG. 24f) and on occasions integrating into, and regenerating, the endothelium of larger arterioles (FIG. 24g). After the first 3 days, the number of engrafted ELPCs was fairly constant up to 3 weeks (data not shown). Similar results were obtained when labeled ELPGs were delivered 21 days after MCT (FIGS. 24h and 24i).

(c) ELPC Administration in the Prevention Model

RVSP was significantly increased at day 21 after MCT compared with saline-treated control rats (48±3 versus 26±0.9 mm Hg. P<0.001; FIG. 25(A) (*P<0.001 v, control; +P<0.001 v.<CT). Administration of somatic cells (ie, skin FBs) had no protective effect (RVSP 51±5 mm Hg), whereas the delivery of syngeneic ELPCs nearly completely prevented the rise in pulmonary systolic pressures at 3 weeks after MCT (32±1 mm Hg, P<0.001 versus MCT alone). Similarly, right ventricular hypertrophy as measured by the ratio of RV/LV weight ratio was increased in animals receiving MCT alone (0.36±0.02) or MCT with FBs (0.30±0.01; FIG. 25B). In contrast, the delivery of bone marrow-derived ELPCs significantly reduced right ventricular hypertrophy (0.26±0.013, P<0.01 versus MGT) to a level not significantly different from saline-treated control animals (0.23±0.01).

(d) Persistence of Protective Effects of ELPCs

FIG. 26 shows persistence of effect as examined in a separate prevention study over a longer time period. RVSP was measured and animals euthanized on the development of predetermined signs of significant morbidity. ELPC group (n=12) exhibited near normal levels of RVSP at euthanasia with only one outlier; in contrast, RVSP in rats injected with fibroblasts (n=13) was markedly elevated (A, P=0.001, vs ELPC group). When analyzed according to time of euthanasia, there was no trend toward an increased RVSP in the ELPC-treated group even at more than 60 days (B). Kidneys (C) from MCT-ELPC-treated rats euthanized at later time points were enlarged with an irregular capsular surface (b), a marked contrast to those from control rats (a).

Histological examination of kidneys from MCT-ELPC-treated rats (d) revealed changes consistent with end stage renal disease including glomerular enlargement, mesangial cell loss, and tubule hyalinization. Normal kidney histology is shown for comparison (c). In contrast to the lung (e), no fluorescently-labeled ELPCs were seen in the kidneys of MCT treated rats 20 minutes after injection (f) (calibration bars=100 μm) or at later time points (data not shown). Glomerular enlargement, mesangial cell loss and tubule hyalinization were caused by the MCT treatment.

At the time of euthanasia, RVSP was again markedly elevated in animals receiving MCT alone (FIG. 26A), whereas with the exception of one animal. ELPC-treated rats exhibited near normal values of pulmonary systolic pressure. Moreover, there was no tendency for RVSP to increase in the ELPC treated group over more than 60 days (FIG. 26B). Necropsy studies in the longest surviving MGT-treated rats revealed markedly enlarged kidneys that exhibited severe histological abnormalities of glomerular and tubular structure consistent with end-stage renal disease in both groups (FIGS. 26Ca through 26Cd). Unlike the lung, no renal engraftment of ELPCs was seen either immediately or 3 days after cell delivery (FIGS. 26Ce and 26Cf).

(e) Effect of ELPC Transplantation in the Reversal Model

At 3 weeks after MCT injection, animals assigned to the three treatment groups exhibited similar increases in RVSP compared with saline controls (FIG. 27A) and comparable to that of the MCT alone group in the prevention protocol. Two weeks later, RVSP had progressed in the MGT animals treated with saline. The delivery of nontransduced ELPCs prevented the further progression of PAH from day 21 (43±4 mm Hg) to day 35 (36±4 mm Hg): however, only animals receiving eNOS-transduced ELPCs demonstrated significant improvement in RVSP at day 35 (31±2 mm Hg) compared with day 21 (50±3 mm Hg, P<0.005; FIG. 28A). Of note, transgene expression was transient and persisted for only 1 week after electroporation (data not shown). The ratio of RV to LV and septal weight was significantly increased in the MGT-treated rats receiving only saline, whereas both ELPG-treated groups displayed significant reductions compared with control rats (FIG. 27B). Similarly, the effects of MGT on the expression of VEGF and markers of endothelial activation (E- and P-Selectin) were normalized by administration of eNOS-transduced ELPGs (data not shown).

(f) Effects of ELPGs on Fluorescent Microangiography

In normal lungs, microangiography revealed an even filling of the distal arteriolar bed with a homogeneous pattern of capillary perfusion (FIG. 28Aa). Immunostaining with an antibody directed to a-SM actin showed minimal muscularization of the distal arterioles in normal lungs. In contrast, 3 or 5 weeks after MGT-induced lung injury (FIG. 28Ab and Ad, respectively), the distal arteriolar bed showed significant narrowing of distal arterioles with widespread capillary occlusion and evidence of increased distal muscularization. In animals receiving ELPGs 3 days after MGT, there was a marked improvement in the appearance of the lung microvasculature, with reservation of arteriolar continuity and enhanced capillary perfusion (FIG. 28Ac). When ELPGs alone were administered 3 weeks after MGT, only modest improvement in capillary perfusion was seen (FIG. 28Ae) with persistent distal muscularization. Only eNOS-transduced ELPGs restored a more normal appearance of the lung circulation in the reversal model (FIG. 28Af). These observations were confirmed by quantification of microvascular perfusion as shown in FIG. 288 (n=6 to 7/group).

(g) Arteriolar Muscularization

In normal lungs, arterioles of <30 μm showed infrequent muscularization with only 14% demonstrating partial muscularization (PM) and no vessels exhibiting full muscularization (FM). In contrast, 35 days after MGT there was a significantly higher proportion of muscularized arterioles (FIG. 28C).

Treatment with eNOS-transduced progenitor cells reduced arteriolar muscularization, whereas nontransduced ELPGs did not, although there was an increase overall in nonmuscularized vessels in both EPLC-treated groups compared with MGT alone.

(h) Survival Analysis

Figure 29:
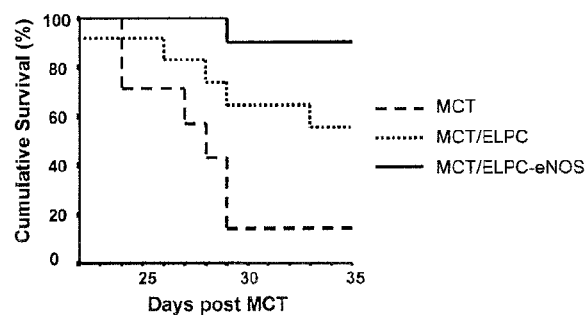
FIG. 29 shows survival to 35 days in a reversal study (animals treated with MCT, ELPC cells, or eNOS-transduced ELPC cells).

In one experiment, only one animal in the MGT-saline group survived to the predefined study end point at 35 days after MGT, and therefore, these data were used for survival analysis only (FIG. 29). The injection of ELPGs transduced with eNOS nearly completely prevented MCT-induced mortality with all but one animal surviving to end-study (P=0.02 versus MGT alone), whereas delivery of nontransduced ELPCs produced an intermediate survival that was not significantly different from MGT alone. However, when the survival analysis was performed including all 63 animals randomized in the reversal protocol, this trend persisted with the survival benefit in MGT-treated animals receiving nontransduced ELPC now reaching statistical significance (P=0.037 versus MCT alone).

Discussion

Bone marrow-derived ELPCs engrafted the MGT-injured lung and incorporated into the pulmonary microvasculature, resulting in near complete prevention of PAH when delivered into the pulmonary circulation within 3 days of MCT injury. Nontransduced ELPCs also prevented further increases in RVSP when injected 3 weeks after MGT-induced lung injury, eNOS-transduced cells also resulted in normalization of pulmonary hemodynamics in animals with established PAH, and this effect was associated with a significant survival benefit. Progenitor cell therapy also resulted in marked improvement in the pulmonary microvascular architecture and alveolar capillary perfusion in MCT-treated animals, which could in part be attributed to repair and regeneration of lung microvascular endothelium.

Of interest, the protective effect of ELPCs appeared to persist as long as it was possible to follow the animals. Indeed, the prevention of MCT induced vascular damage in the lung unmasked profound renal toxicity, which had been previously recognized in the reports that first characterized the toxicity of MCT. This additional toxic effect of MCT clearly represents a significant limitation for studies of long-term survival after lung-specific therapy of PAH in this model.

The present results show for the first time that both ELPCs and eNOS-transduced ELPCs can dramatically improve pulmonary hemodynamics and survival in animals with established PAH, while restoring the continuity of the distal arteriolar bed. These data have important implications for the therapy of this lethal disease and support the exploration of regenerative cell-based gene strategies for the treatment of patients with severe refractory PAH for whom therapeutic options are very limited and the prognosis is poor.

EXAMPLE 22—PREVENTION OF
LPS-INDUCED ACUTE LUNG INJURY BY
Mesenchymal Stem Cells (MSCS) Overexpressing
Angipoietin-1 (Ang-1)

Objectives:
The objective was to test the efficacy of MSC cells, and cell-based gene transfer using Ang-1-transduced MSC cells, to reverse or prevent Acute Respiratory Distress Syndrome (ARDS), the clinical correlate of severe Acute Lung Injury.
Methods:
Results
Characterization and Ang1 Transfection of MSCs (a) Murine MSCs were Obtained from Tulane Center for Gene Therapy (New Orleans, La.) and Demonstrated to Differentiate into Three Predominant Mesenchymal Lineages: Adipocytes, Osteocytes, and Chodrocytes (Results not Shown).

The full-length coding sequence of Ang1 (1115-bp) was cloned into the expression vector pFLAG-CMV-1 (Sigma, St. Louis. Mo.) as previously described (51). Nuclear-targeting electroporation (Amaxa, Gaithersburg. Md.) was used to transfect MSCs with Ang1 plasmid or empty vector plasmid. Human Ang1 protein expression was verified by ELISA (R&D Systems, Minneapolis. Minn.).

Twenty-four hours after nucleofection with human plasmid Ang1 (pAng1). Ang1 protein (724±283 µg/mL) was detected in the culture supernatant (from $5 \times 10^5$ cells), and levels were sustained for more than 5 days. Phosphorylation of Tie-2 receptor, mediated by human Ang1 (hAng1) protein expressed using the same plasmid, has been previously validated by our group (51). Nontransfected or null-transfected (empty factor) MSCs produced no detectable Ang1 protein.

(b) Effect of MSCs Alone or Transfected with hAng1 (MSCs-pAng1) on Acute LPS-Induced Pulmonary Inflammation (Lipopolysaccharide)-induced pulmonary inflammation is a well known and well documented animal model for ARDS. Measures of extent of inflammation include cell counts from bronchoalveolar lavage (SAL) and a measure of pro-inflammatory cytokine levels in SAL fluid and lung parenchymal homogenates. LPS-induced permeability in the lung (i.e. extent of Acute Lung Injury) can also be measured.

LPS was administered to adult C57S1/6J mice via intra-tracheal instillation, followed 30 minutes later by an injection of saline, MSCs alone, or MSCs transfected with pFLAG (null) or hAng1 plasmid (MSCs-pAng1) via the right jugular vein (FIG. 1) Human Ang1 protein expression was confirmed by ELISA for each batch of MSCs-pAng1 employed. Naive mice (without LPS instillation) were injected with saline or MSCs to serve as controls for any inflammatory response that might result from the injected MSCs. Three days later, bronchoalveolar lavage (BAL) fluid was collected The total inflammatory cell count in the BAL fluid was increased approximately 20-fold at day 3 following administration of LPS. Treatment of animals with MSCs alone significantly reduced the total cell count in BAL fluid (FIG. 30A, p<0.05 compared to LPS/saline group) Treatment with MSCs-pAng1 further reduced the BAL fluid cell count to a level similar to control, naive mice (p<0.01 for total cells compared to LPS/saline group) Substitution of skin fibroblasts for MSCs did not prevent the observed LPS-induced increase in BAL fluid cell counts (data not shown).

Figure 30:
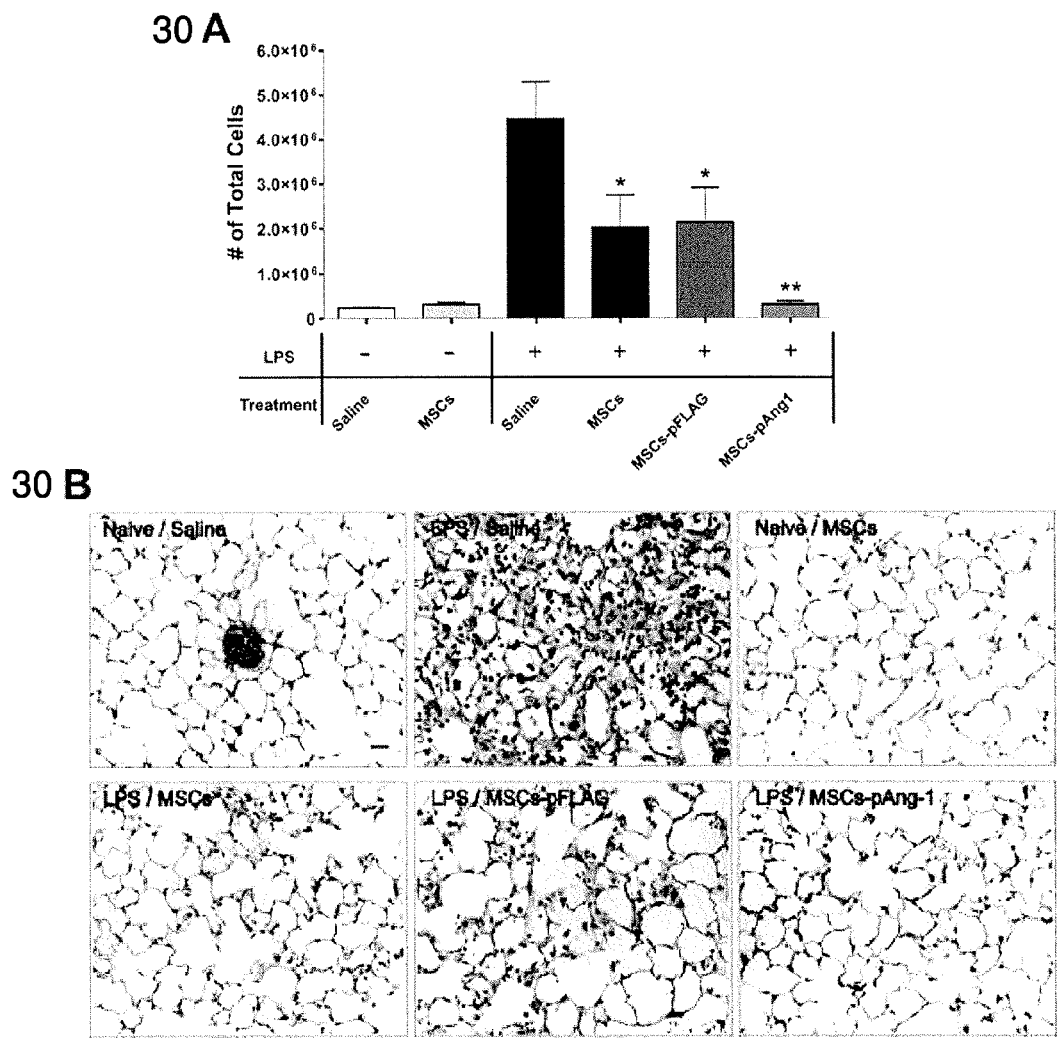
FIG. 30 shows the therapeutic potential of MSCs, alone or transfected with pAng1, on LPS induced lung inflammation in mice.

Histological assessment of lung sections 3 days after the administration of LPS revealed evidence of marked inflammatory infiltrates, interalveolar septal thickening, and interstitial edema (FIG. 30B). MSCs alone reduced airspace inflammation, which was more apparent in mice treated with MSCs-pAng1. Morphometric analysis measuring interalveolar septal thickness showed a modest increase in LPS alone group, with a significant reduction in animals receiving MSCs (data not shown). Severity of lung injury were also scored using a quantitative histopathology score system, which evaluates lung injury in four categories: alveolar septae, alveolar hemorrhage, intra alveolar fibrin, and intra-alveolar infiltrates. Treatment with MSCs or MSCs-pAng1 again exhibited trends of reduced lung injury scores.

Figure 31:
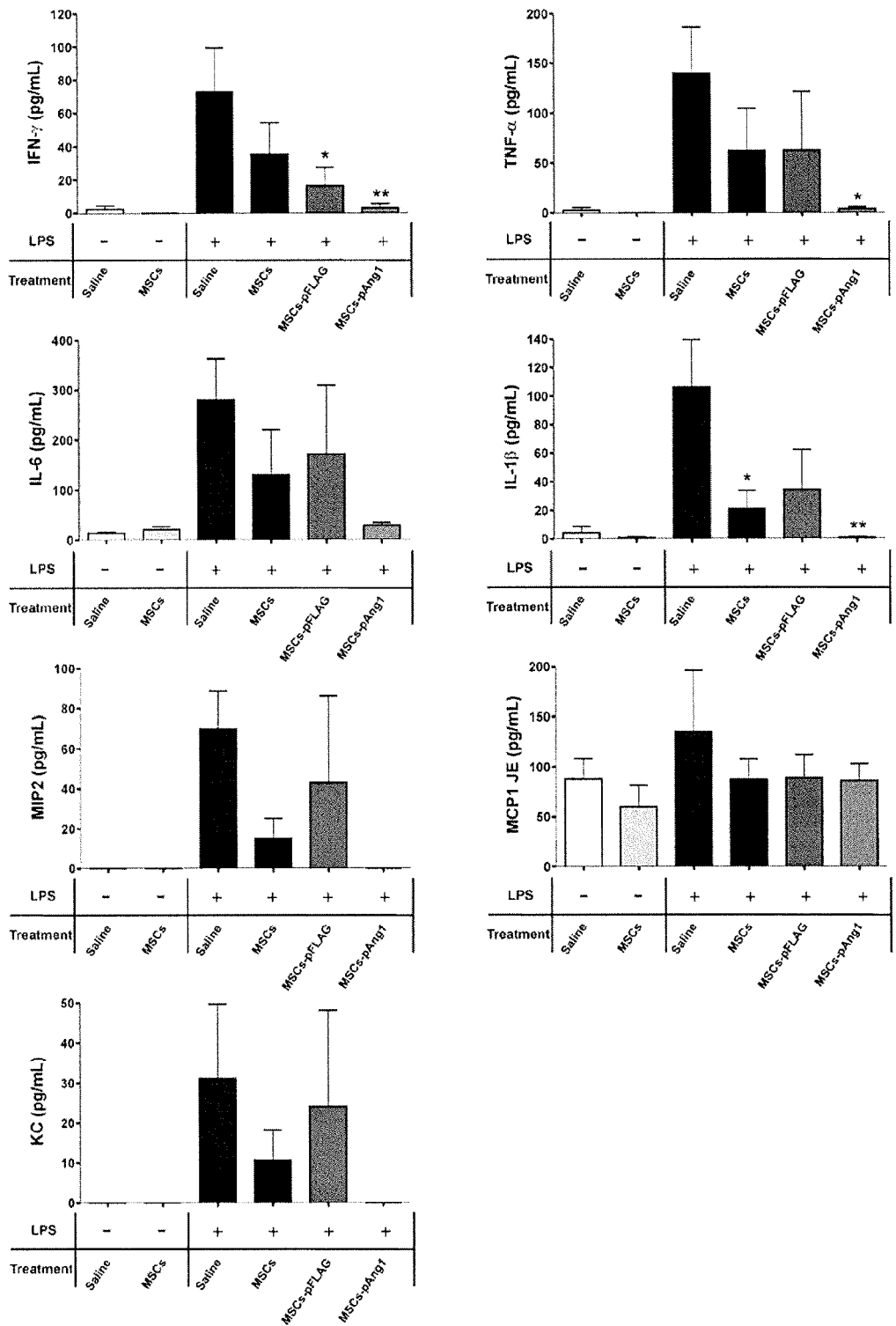
FIG. 31 shows the levels of pro-inflammatory cytokines and chemokines in SAL fluid. Levels of the pro-inflammatory cytokines, IFN-y, TNF-a. IL-6 and IL-113, in SAL fluid, were measured using ELISA. Chemokine levels (MIP-2, JE [murine MCP-1 homologue], and KG [murine IL-8 homologue]), in BAL fluid were measured by multiplex immunoassay. Group comparisons were analyzed by one-way ANOVA with Dunnett's post hoc test. *$p<0.0$ and **$p<0.01$, LPS/Saline vs. each treated group (MSCs, MSCs-pFLAG, or MSCs-pAng1), n=5 per group.
Figure 32:
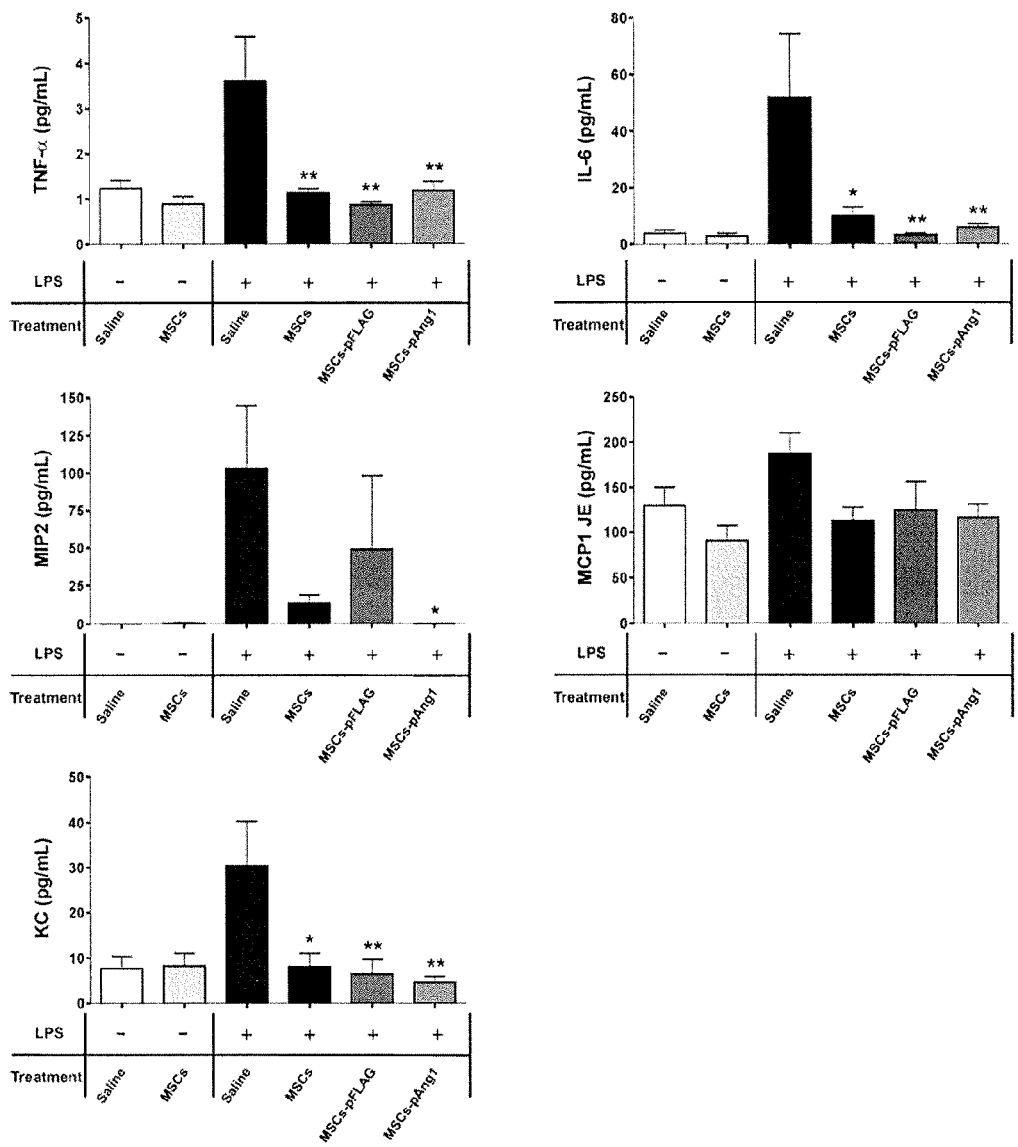
FIG. 32 shows levels of pro-inflammatory cytokines and chemokines m lung homogenate. Cytokine (TNF-a and IL-6) and chemokine (MIP-2, JE [murine MCP-1 homologue], and KC [murine IL-8 homologue]) levels in lung homogenates were measured by multiplex immunoassay. Group comparisons were analyzed by one-way ANOVA with Dunnett's post hoc test. *$p<0.05$ and **$p<0.01$. LPS/Saline vs. each treated group (MSCs, MSCs-pFLAG, or MSCs-pAng1), n=5 per group.

To further evaluate the anti-inflammatory actions by MSCs and MSCs-pAng1, levels of pro-inflammatory cytokines and chemokines were measured in BAL fluid collected from animals. Pro-inflammatory cytokines (IFN-γ, TNF-α. IL-6, and IL-1) were all elevated in BAL fluid in response to LPS challenge compared with naive animals receiving saline (FIG. 31). Treatment with MSCs alone decreased the levels of pro-inflammatory cytokines, while treatment with MSCs-pAng1 dramatically reduced cytokine levels to baseline values observed in naive mice. LPS instillation also increased the levels of MIP-2, JE (murine homologue of MCP-1), and KC (murine homologue of IL-8) in BAL fluid, whereas treatment with MSCs, and to a greater extent MSCs-pAng1, attenuated these increases. Similarly, LPS-induced cytokine and chemokine levels in whole lung homogenates were significantly reduced by treatment with MSCs or MSCs pAng1 (FIG. 32), with treatment with MSCs alone as effective as MSCs-pAng1 in reducing pro-inflammatory cytokine and chemokine levels. No detectable differences in cytokine and chemokine levels in plasma was observed among different treatment groups, suggesting that intratracheal LPS instillation induced localized inflammation in the lungs, and did not result in systemic inflammation in our model (data not shown).

(c) Effect of MSCs and MSCs-pAng1 on LPS-Induced all

Concentrations of total protein, albumin, and 1 gM were assayed on collected BAL fluid to evaluate the integrity of the alveolar-capillary membrane barrier and assess pulmonary vascular leakage as a marker for ALI These parameters of vascular leakage were markedly increased (total protein: 3-fold increase; albumin: 4-fold increase; and IgM: 25-fold increase) in BAL fluid 3 days after LPS instillation compared to naive mice. Treatment with MSCs alone reduced total protein, albumin and IgM levels modestly (FIG. 33A to C). Treatment with MSCs-pAng1 restored total protein, albumin and IgM levels to levels not different from naïve control mice ($p<0.01$ for total proteins and albumin, and $p<0.05$ for IgM compared to LPS/saline group, respectively).

(d) Retention and Persistence of MSCs in Mice with or without LPS-Induced all

Figure 34:
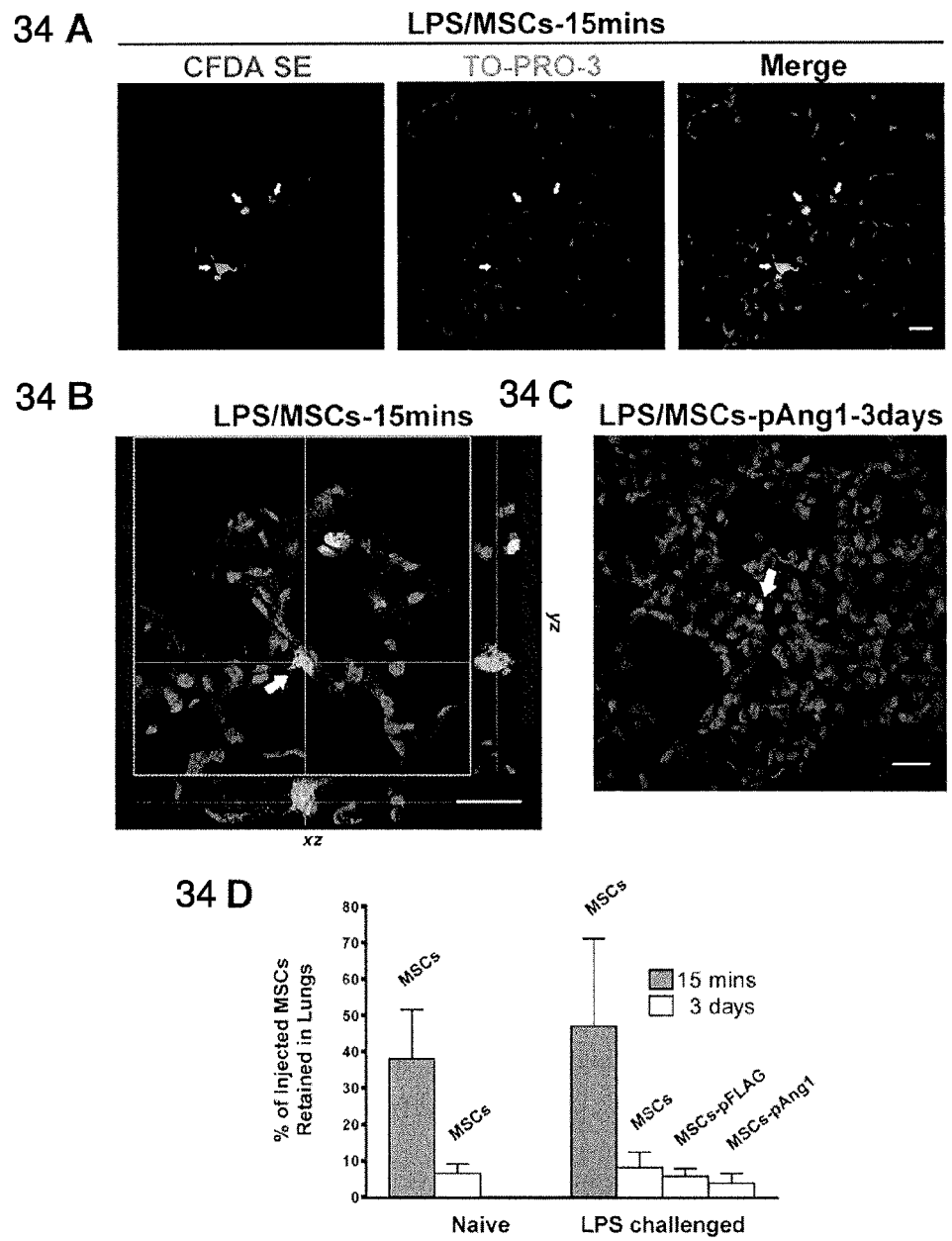
FIG. 34 shows retention of injected MSCs in mice with or without LPS-induced ALI. MSCs were labeled with the cell tracing dye CFDA SE (green) prior to injection. Nuclei were stained with TO-PR0-3 (blue).

Retention of MSCs in the lung after central venous injection was verified by confocal microscopy and flow cytometry. MSCs labeled with the green fluorescent cell tracker CFDA SE were observed in lung sections from both naive and LPS-challenged mice sacrificed at 15 minutes (initial retention, FIG. 34A). Although labelled cells could still be detected 3 days after injection, they were far less abundant (FIG. 34C). No cell-specific green fluorescence was observed in sections from animals that did not receive CFDA SE-labelled cells (figure not shown). To confirm that the green fluorescence observed was indeed from an intact cell, a z-series using laser scanning confocal microscopy was performed showing blue nuclear staining by TO-PR0-3 surrounded by green fluorescence by CFDA SE labelling (FIG. 34B). The percentage of the injected MSCs retained in the lungs was quantified by flow cytometry following Dispase lung digestion. An average 47% of injected cells were found in the lungs shortly after MSCs delivery in LPS-challenged mice lungs comparing to 38% in naive mice; though the difference was not statistically significant. Regardless of lung injury, the majority of MSCs were lost from the lung after 3 days, leaving less than 8% of cells remaining (FIG. 34D).

Conclusion

MSCs alone are an effective treatment for acute lung injury, which is an important underlying cause of human ARDS. As such, administration of MSCs alone should be an effective treatment for ARDS. MSCs transformed to express Ang-1 before administration are an even more effective treatment for ARDS, resulting in near complete prevention of any evidence of acute lung injury in response to LPS.

EXAMPLE 23: TREATMENT OF ARDS WITH SKIN FIBROBLAST CELLS Expressing Ang-1

(a) Cell Transfection

Skin fibroblast cells were isolated from syngeneic male Fisher344 rats (Charles River Co., Quebec, Canada) and transfected with null plasmid vector, pFLAG-CMV-1 (pFLAG), or the same vector containing the full-length eDNA for human Ang-1 (pAng-1) using Superfect (Qiagen. Valencia, Calif.). After 24 hours, cells were suspended in Dulbecco's PBS (Invitrogen, Carlsbad, Calif.) for injection into the pulmonary circulation.

(b) Rat Model of ALI

All animal studies were conducted under protocols approved by the animal care committee at St. Michael's Hospital and in accordance with Canadian Council of Animal Care guidelines. Male Fisher344 rats were randomly assigned to one of four experimental groups. Transfected fibroblasts ($1.5\times10^6$ cells in 1 mL) were injected into the left exterior jugular vein; and 24 hours later, rats received intratracheal instillation of saline or LPS. Six hours after instillation, rats were tracheotomized and bronchoalveolar lavage performed. Lavage total cells were counted using a hemocytometer, and differential was determined by Hematoxylin and Eosin staining. Lung tissue was flash frozen and blood plasma isolated. In separate rats, lung tissue was harvested by paraformaldehyde-inflation.

(c) Mouse Model of All

Female Tie2 haploinsufficient and Ang-1 overexpressing transgenic mice were randomly assigned to naive or LPS-challenged groups. Wildtype littermates were used as controls. Mice received intratracheal instillation of LPS and after 6 hours, bronchoalveolar lavage was performed and blood plasma isolated. The left lung was flash frozen and the right lung was digested for flow cytometry. In separate mice, lung tissue was harvested by paraformaldehyde-inflation.

(d) Flow Cytometry

The right lung was perfused with 10 mL heparinized saline and inflated with disapaseII followed by a 1% low temperature agarose. The chest cavity was packed with ice for 5 minutes. The lung was removed and incubated in 1 mL of disapassII at room temperature for 45 minutes and then transferred to 7 mL of DMEM with 100 U/mL DNaseI and separated into single cells by passing through a 70 µm cell strainer. The isolated cells were suspended in staining buffer (2% heat-inactivated Fetal Calf Serum, 0.09% sodium azide in Dulbecco's PBS and blocked using purified rat anti-mouse Fc block. Cells were stained with PE-conjugated anti-CD31 and one of the following biotin-conjugated antibodies: anti-E Selectin, anti-P Selectin, anti-ICAM-1, or anti-VCAM-1, with streptavidin-APC Cy7 as the secondary stain. Isotype controls were used to determine background staining. Flow cytometry was performed using the Becton Coulter Cytomics FC500.

(e) Quantitative RT-PCR

Total RNA was extracted from lungs using TRIzol reagent and reverse transcribed. Quantitative PCR was performed using SYBR GreenI PCR Master Mix and the ABI PRISM 7900HT. Delta $C_T$ analysis was used to calculate expression in comparison to 188 RNA. Primers for genes of interest are listed in Table 1.

TABLE 1

| Primers for quantitative real-time RT-PCR | | |
| --- | --- | --- |
| | sense primer | antisense primer |
| Total Ang-1 | 5'-GAGCTCCTTGAGAATTACCTTGTGG-3' | 5'-CGAGTTGATTTAGTACCTGGGTCTC-3' |
| Human Ang-I | 5'-CTCCAATACTCACCCTGTTATGTC-3' | 5'-GACACTGGAACAGTCTGAATCTGG-3' |

TABLE 1-continued

Primers for quantitative real-time RT-PCR

| | sense primer | antisense primer |
|---|---|---|
| Tie2 | 5'-AGAACAACATAGGATCAAGCAACCC-3' | 5'-CTCTTCAGTTGCAACATAATCAGAAACG-3' |
| Rat ICAM-1 | 5'-CAOTGCTGTACCATGATCAGAATAC-3 | 5'-GTAATAGGTGTAAATGGACACCAC-3' |
| Rat VCAM-1 | 5'-ACGAGTGTGAATCGAAAACCGAAG-3' | 5'-GTATTACCAAGGAGGATGCAAAGTAG-3' |
| Rat E-Selectin | 5'-GTGAGTATTCACCCTCTAATAGATG-3' | 5'-CTCTCTAGAACTTGTGAACCAGAAC-3' |
| Rat P-Selectin | 5'-AGTCTTCACGAACGCTGCATATGAC-3' | 5'-0ACCAGGAAACTTGTTATCTGCATG-3' |
| Rat iNOS | 5'-GAGACGTTCGATGTTCGAAGCAAAC-3' | 5'-GCTTTGTTGAGGTCTAGAGACTCTG-3' |
| Rat eNOS | 5'-CTACGAAGAATGGAAGTGGTTCC-3' | 5'-GTGCTGACTCTGACAGAGTCGTACC-3' |
| Rat HO-I | 5'-GAAGAGGAGATAGCGAAACAAGC-3' | 5'-CTCGTGGAGACGCTTTACGTAGTGC-3' |
| RatET-I | 5'-GCTTCTACAGTTTCTTGTTCAGAC-3' | 5'-GGATGCAAACGAAGACAGGTTAGG-3' |
| Rat Ang-2 | 5'-TTTGTCTCCCAGCTGACCAGTGG-3' | 5'-GACAGGTAGAAGTGCTCATACAG-3' |
| Rat VEGF | 5'-CATAGGAGAGATGAGCTTCCTGC-3' | 5'-CTCTGAACAAGGCTCACAGTGATTTTC-3' |
| 18S | 5'-GACGATCAGATACCGTCGTAGTTC-3' | 5'-GTTTCAGCTTTGCAACCATACTC-3' |

(f) ELISAs

Rat TNF-α, IL-1β and IL-6 ELISA kits and mouse TNF-α. IL-1β and IL-6, soluble ICAM-1, soluble VCAM-1, soluble E-Selectin and soluble P-Selectin ELISA kits were used following the manufacturer's instructions. The ET-1 ELISA kit was used following the manufacturer's instructions on precipitated lavage fluid spun at 3000 g for 20 minutes.

(g) Western Blots

Western Blots were performed using the following primary antibodies: rabbit anti-Tie2, goat anti-Ang-1, mouse anti-β-actin; rabbit anti-Tyr992-phospho-Tie2; goat anti-rat E-Selectin, mouse anti-rate ICAM-1; and mouse anti-rat VCAM-1. Tie2 was immunoprecipitated using rabbit anti-Tie2 antibody and membranes probed with mouse anti-phosphotyrosine (1:4000, Upstate Biotechnology; Lake Placid. N.Y.). Predetermined molecular mass standards were use as markers (Invitrogen, Carlsbad, Calif.).

(h) Immunohistochemistry and Histopathology

In separate experiments, $1.5 \times 10^6$ CMTMR-labeled rat fibroblast cells were injected into naive rats, which were sacrificed 15 minutes, 24 hours or 48 hours later. Confocal immunohistochemistry was performed on 15 µm lung cryo-sections stained with rabbit anti-von Willebrand Factor or mouse anti-human Ang-1.

Mouse and rat lung samples were fixed in 4% paraformaldehyde, paraffin embedded, cut into 5 µm sections, and stained with Hematoxylin and Eosin. Intra-alveolar septal thickness was quantified by measuring all septae along a crosshair placed on each image (approximately 50 septae per animal) using ImageJ software (National Institutes of Health).

(i) Statistics

Data were represented as mean±standard error of the mean. Differences between groups were assessed using ANOVA (with post hoc comparisons using Student-Newman-Keuls test). A value of $p<0.05$ was considered statistically significant.

Results (a) Role of Angiopoietin-1 in a Rat Model of ALI

Figure 35:
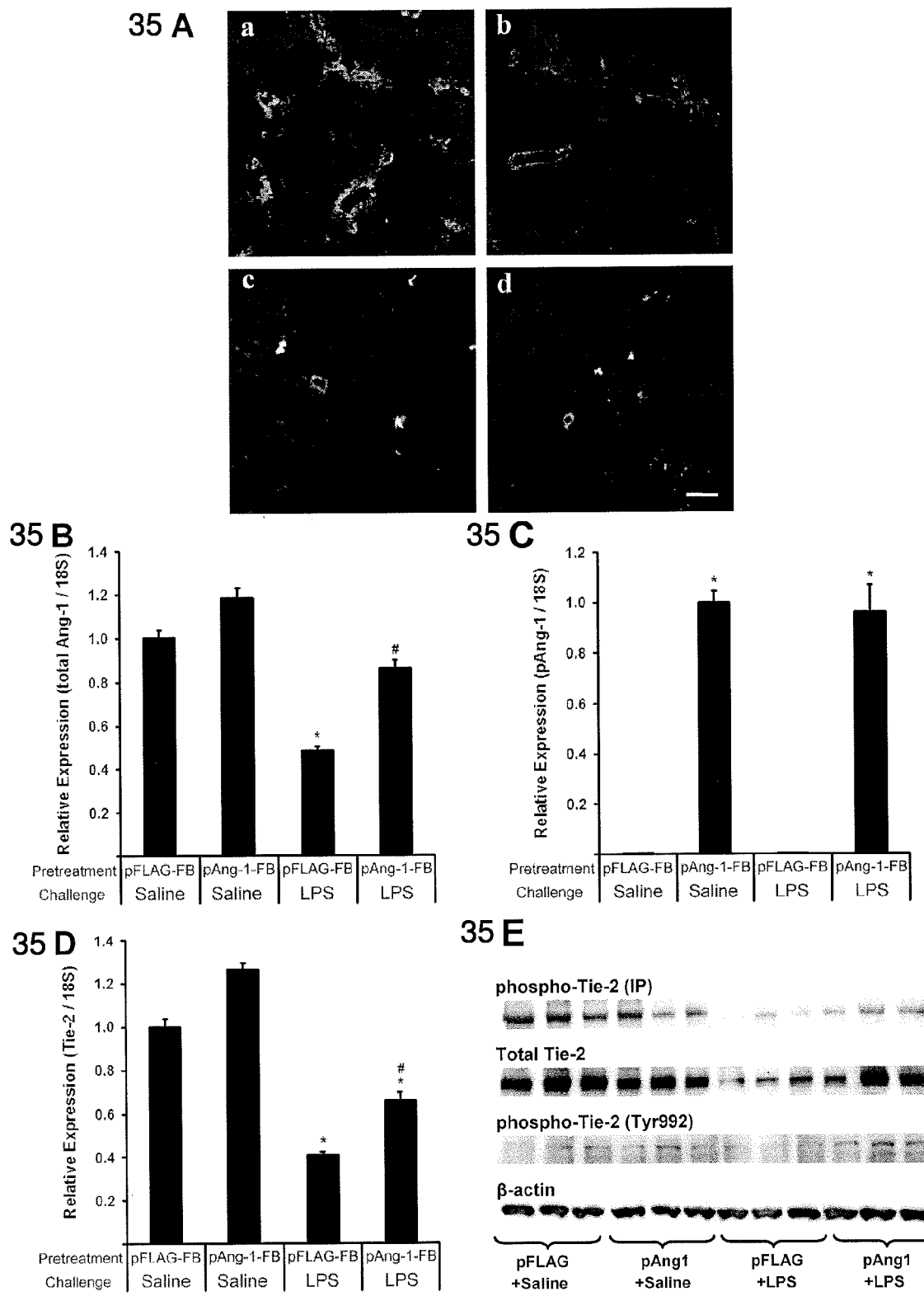
FIG. 35 shows cell-based gene transfer restores Angiopoietin-1 expression in a rat model of ALI.

Immunofluorescent staining of the lung with von Willebrand Factor (vWF) to label the endothelium is shown in FIG. 35A, panels a and b. Fifteen minutes after injection, CMTMR-labeled fibroblasts were visible in or near small arterioles (panel a), persisting in the lungs 48 house later (panel b). CMTMR-labeled fibroblasts were not detectable in other tissues and have previously been shown to persist in the lung for up to 6 months. Immunofluorescent staining of the lung for Ang-1 was shown in FIG. 35A, panels c and d. The expression of the Ang-1 transgene by transplanted fibroblasts was evident by the yellow color indicating colocalization of CMTMR and Ang-1 signals 15 minutes after injection (panel c), again persisting for 48 hours after injection (panel d). Immunohistochemical staining confirmed that Ang-1 expressing fibroblasts persist in the lung even after LPS exposure (data not shown). Quantitative real-time RT-PCR analysis of total Ang-1 mRNA levels showed a reduction in total Ang-1 mRNA of 53% following LPS exposure compared to saline with pFLAG-transfected cells (FIG. 35B) Pretreatment with pAng-1-transfected cells restored total Ang-1 mRNA to sham levels. In contrast, plasmid-derived Ang-1 mRNA was undetectable in animals pretreated with pFLAG-transfected cells, while plasmid Ang-1 transcript levels were similar in both groups that received injection of pAng-1 transfected cells (FIG. 35C). RT-PCR analysis of the receptor tyrosine kinase Tie2 demonstrated a reduction in Tie2 mRNA of 59% following LPS exposure compared to saline with pFLAG-transfected cells (FIG. 35D); and pretreatment with pAng-1-transfected cells partially restored Tie2 expression. Moreover, both total Tie2 and phosphorylated Tie2 protein were decreased following LPS exposure compared to saline with pFLAG-transfected cells (FIG. 35E), which again was partially restored by pretreatment with pAng-1-transfected cells.

Thus, decreases in Tie2 activity may contribute to endothelial inflammation; strategies to counteract this, such as treatment with Ang-1 expressing fibroblasts may be therapeutic.

(b) Angiopoietin-1 Cell Therapy Attenuated Intra-Alveolar Septal Thickness and Airspace Inflammation in Rats:

Administration of pAng-1, compared to pFLAG, transfected cells did not significantly alter lung morphology in rats that received intratracheal instillation of normal saline (FIG. 36A, panels a and b). Intra-alveolar septal thickness and total cell count in bronchoalveolar lavage fluid (BALF) were increased 2 and 4-fold, respectively, following LPS exposure compared to saline (FIG. 36A, panel c. FIGS. 36B and 36C). Pretreatment of pAng-1-transfected cells significantly reduced these indicators of vascular inflammation (FIG. 36A, panel d, FIGS. 36B and 36C). The reduction in total BALF cells was mainly attributable to a reduction in the number of neutrophils (Table 2). Total protein in BALF and lung wet weight to body weight ratio were increased following LPS exposure compared to saline (FIGS. 36D and 36E). There was a trend towards a reduction in these indicators of pulmonary vascular leak (p=0.10).

TABLE 2

Effect of Ang-1 cell therapy on inflammatory cells in BALF

|  | pFLAG-FB Saline | pAng-1-FB Saline | pFLAG-FB LPS | PANG-1-FB LPS |
|---|---|---|---|---|
| Total Cells ($10^6$ cells/mL) | 2.5 ± 0.6 | 2.4 ± 0.3 | 10.5 ± 1.7* | 6.0 ± 0.7*# |
| Neutrophils ($10^6$ cells/mL) | 1.9 ± 0.4 | 2.0 ± 0.3 | 10.1 ± 1.6* | 5.6 ± 0.8*# |
| Monocytes ($10^4$ cells/mL) | 5.5 ± 2.9 | 4.0 ± 1.0 | 27.5 ± 4.7* | 9.5 ± 2.0*# |
| Macrophages ($10^4$ cells/mL) | 5.6 ± 1.9 | 3.4 ± 0.7 | 1.6 ± 0.3 | 2.5 ± 1.6 |

\* = $p < 0.05$ vs. pFLAG-transfected fibroblast injected rats challenged with saline;
\# = $p < 0.05$ vs. pFLAG-transfected fibroblast injected rats challenged with LPS.

Figure 37:
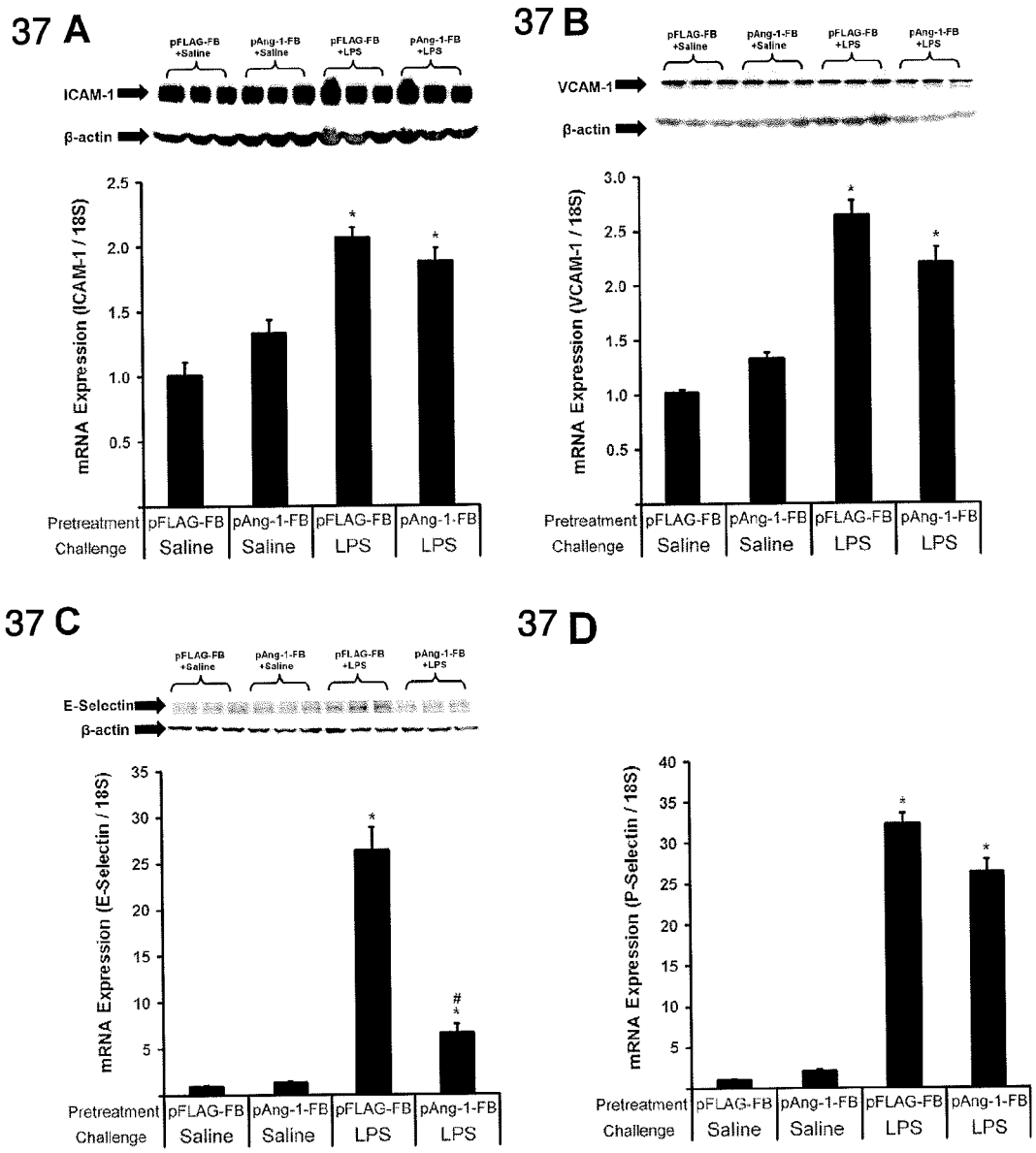
FIG. 37 shows the effect of angiopoietin-1 cell therapy on endothelial adhesion molecule expression in rats.

(c) Selective Effect of Angiopoietin-1 Cell Therapy on Endothelial Adhesion Molecule Expression in Rats:

Endothelial adhesion molecule expression is a marker of injury and activation of endothelial cells. In animals receiving pFLAG-transfected cells, mRNA levels for ICAM-1. VCAM-1, P-Selectin and E-Selectin in whole lung tissue were increased by 2 to 32-fold following exposure to LSP compared to saline (FIG. 37A-D), the increases in ICAM-1, VCAM-1 and P-Selectin mRNA levels following LPS were similar in rats receiving pang-1 compared to pFLAG-transfected cells. In contrast, pretreatment with pAng-1-transfected cells largely prevented the increase in mRNA expression of the endothelial-selective adhesion molecule, E-Selectin, in LPS treated rats (FIG. 37C). Western blot analysis showed no difference in ICAM-1 or VCAM-1 protein expression between the experimental groups, whereas E-Selectin protein was induced by LPS exposure and this was substantially reduced by the administration of p-Ang-transfected cells.

EXAMPLE 24—ROLE OF ANGIOPOIETIN-1 IN TRANSGENIC MODELS OF all

Experiments were performed using Tie2 heterozygous deficient mice (Tie2+/−) or binary transgenic mice in which Dox-conditional Ang-1 overexpression was targeted to endothelium using the Tie1 promoter (tTA-Ang-1). Wild-type (WT) littermates were used as controls. Total lung Ang-1 protein expression by Western Blot analysis was not different between endothelial-targeted, Ang-1 overexpressing mice and WT or Tie2 heterozygous deficient mice (FIG. 38A). This may be a result of high basal levels of pulmonary Ang-1 expression in extra-endothelial cells under normal conditions, which may overshadow the human Ang-1 transgene expression which is restricted to the endothelium. However, the decrease in Ang-1 protein expression seen in WT mice following LPS challenge was blunted in tTA-Ang-1 mice. Paradoxically, the LPS-induced reduction in Ang-1 was also attenuated in Tie2 deficient mice, which we hypothesize might reflect a compensatory mechanism for the very low expression of Tie2 in these animals. As expected, basal Tie2 expression was reduced by about 50% in Tie2+/− compared with WT mice (FIG. 38B) and Tie2 protein was markedly downregulated by LPS exposure in WT mice, which was further reduced in Tie2+−.

Figure 39:
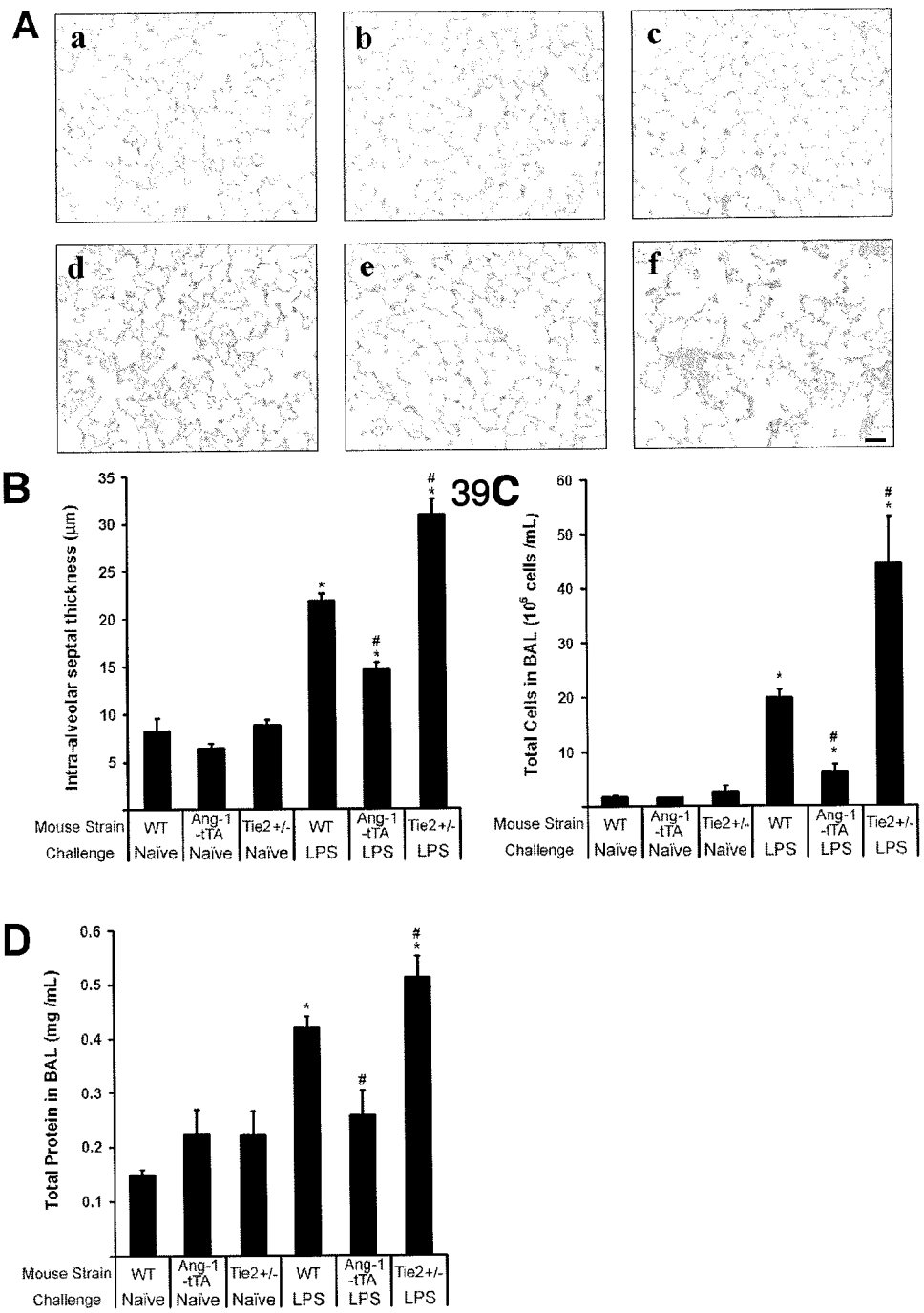
FIG. 39 shows septal thickness and airspace inflammation in transgenic mice.

(a) Septal Thickness and Airspace Inflammation in Transgenic Mice:

In the absence of LPS, lung morphology was not significantly different between groups of transgenic mice (FIG. 39A). The intra-alveolar septal thickness increased 1.7-fold following LSP exposure in WT mice (FIG. 39B). This increase in septal thickness was significantly blunted in Ang-1 overexpressing mice, whereas Tie2 deficient mice exhibited nearly a 50% greater increase in intra-alveolar septal thickness in response to LPS compared to WT animals. LPS-induced airspace inflammation mirrored these differences, with the increase in total cells in BALF, attributable mainly to an increase in neutrophils, being markedly blunted in Ang-1 overexpressing mice, whereas Tie2 deficient animals consistently exhibited exaggerated air space inflammation (FIG. 39C, Table 5). Total protein in BALF was increased 3-fold following LPS in WT mice and again this was suppressed in Ang-1 overexpressing mice and increased in Tie2 deficient animals (FIG. 39D). In addition, mortality was higher in Tie2 haploinsufficient mice subjected to LPS challenge (60% mortality within 1 hour) compared to the other experimental groups (17%; p<0.02). Necropsy revealed that mortality was associated with massive alveolar flooding in Tie2 deficient mice.

TABLE 5

Inflammatory cells in BALF of transgenic mice.

| | WT Naïve | Ang-1-tTA Naïve | Tie2 +/− Naïve | WT LPS | Ang-1-tTA LPS | Tie2 LPS |
|---|---|---|---|---|---|---|
| Total Cells ($10^6$ cells/mL) | 1.7 ± 0.3 | 1.6 ± 0.1 | 2.6 ± 1.1 | 19.9 ± 1.4* | 6.3 ± 1.4*# | 44.4 ± 8.6* |
| Neutrophils ($10^5$ cells/mL) | 5.6 ± 0.9 | 2.3 ± 0.5 | 3.3 ± 0.9 | 164 ± 13* | 47.1 ± 6.4*# | 345 ± 17*# |
| Monocytes ($10^5$ cells/ml) | 0.3 ± 0.2 | 0.0 ± 0.0 | 0.5 ± 0.3 | 16.0 ± 3.6* | 1.8 ± 0.5*# | 24.9 ± 6.5*# |

TABLE 5-continued

Inflammatory cells in BALF of transgenic mice.

| | WT Naïve | Ang-1-tTA Naïve | Tie2 +/− Naïve | WT LPS | Ang-1-tTA LPS | Tie2 LPS |
|---|---|---|---|---|---|---|
| Macrophages ($10^5$ cells/ml) | 1.1 ± 0.1 | 1.3 ± 0.05 | 2.4 ± 0.1* | 1.9 ± 0.9 | 1.4 ± 0.6 | 7.42.0*# |

Figure 40:
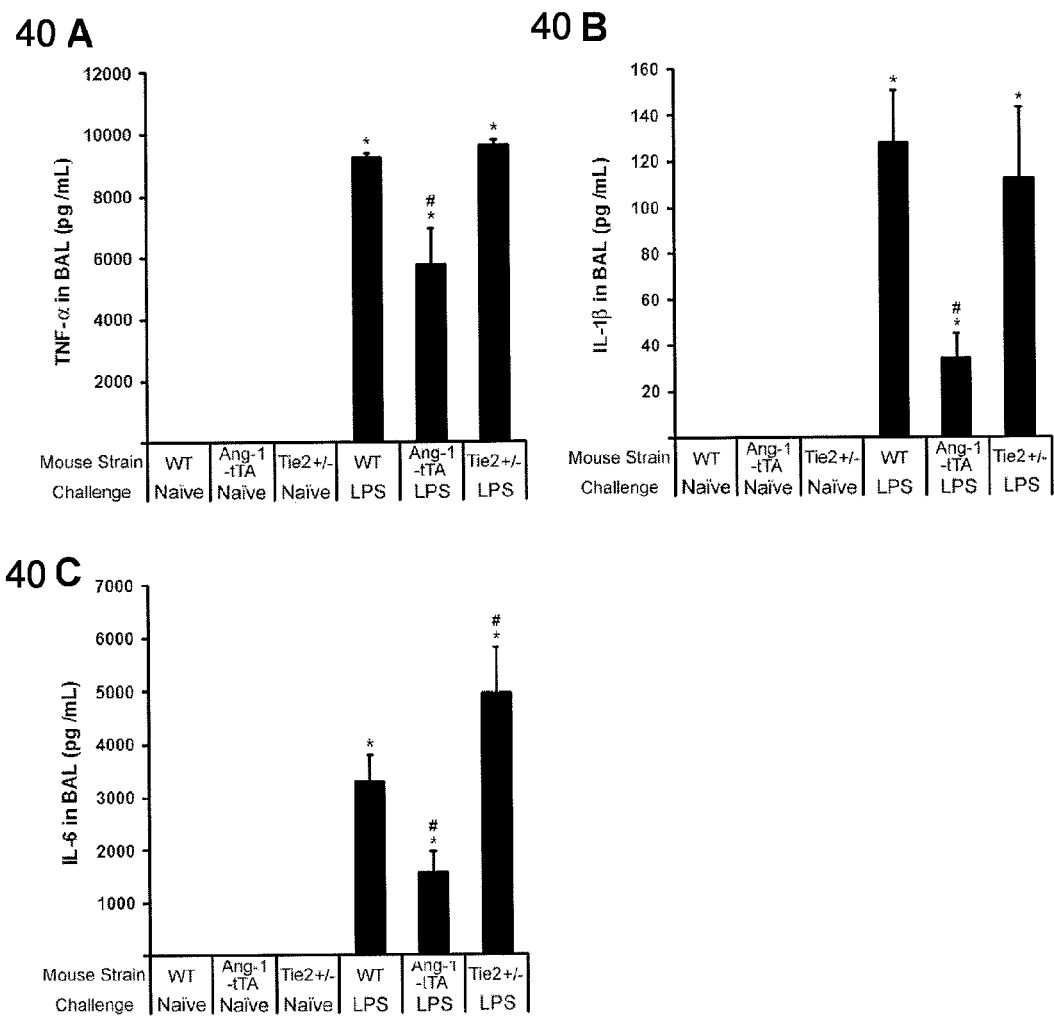
FIG. 40 shows proinflammatory cytokines in BALF of transgenic mice.

\*= $p < 0.05$ vs. WT naive mice;
= $p < 0.05$ vs. WT mice challenged with LPS (b) Ang-1 Overexpression Reduces Endothelial Expression of Adhesion Molecules:

To evaluate changes in the expression of adhesion molecules in endothelial cells versus other lung cell types, mouse lungs were digested in dispase and stained for the endothelial cell marker. CD31. Subsequently, flow cytometry was performed for each adhesion molecule separately using 2-colour flow cytometry, gated around the CD31+ and CD31− populations. The percentage of endothelial cells positive for E-Selectin. P-Selectin. ICAM-1 and VCAM-1 increased from 4 to 34-fold following LPS in wildtype mice (FIG. 41A, 100 left hand panels). Endothelial-targeted Ang-1 overexpression nearly completely suppressed the LPS-induced increases in endothelial expression of E-Selectin. P-Selectin and VCAM-1 (FIGS. 41A, 41B and 41D), but had only a marginal effect on ICAM-1 expression (FIG. 40C). Surprisingly. Tie2 deficient mice showed similar, although more modest, reductions in adhesion molecule expression in response to LPS. This may be explained by greater adhesion molecule shedding in these animals (FIGS. 40A, 40B, and 40C), consistent with more advanced inflammation. As well, similar changes, though with lower overall numbers of positive cells, were seen when the expression of these adhesion molecules was studied in all dispersed lung cells (FIG. 41, right hand panels).

Discussion

In both the rat and mouse models, Ang-1 overexpression markedly reduced septal edema in response to LPS, as well as alveolar and endothelial inflammation. This data supports the potential utility of Ang-1 in the treatment of acute lung injury.

The endothelial monolayer plays a critical role in many aspects of the pathogenesis of ALI and ARADS. Alterations in the production of vasoactive mediators by injured endothelium leads to impaired hypoxic pulmonary vasoconstriction. Increased expression of angiogenic growth factors, such as VEGF, contributes to increased endothelial permeability and interstitial edema, increased pulmonary dead space, and vascular remodeling. However, perhaps the most important role of the endothelium in ALI and ARDS is in regulation of inflammation. Leukocyte adhesion to the endothelium is a prerequisite for migration into the lung parenchyma, where the inflammatory cells contribute to lung injury. Indeed, previous studies have reported attenuation of lung injury in experimental ALI by blocking endothelial adhesion molecules. Thus, strategies to selectively reduce endothelial inflammation in response to injury could be of potential benefit, not only in ALI and ARDS, but also in systemic inflammatory disorders such as the Systemic Inflammatory Response Syndrome, sepsis and the Multiple Organ Dysfunction/Failure Syndrome.

Ang-1 cell-based gene transfer also resulted in several downstream effects in the rat model of ALI. Expression of two protective enzymes, eNOS and HO-1, was increased following Ang-1 cell therapy in LPS-challenged rats. Mice overexpressing eNOS were previously shown to be protected from lung injury during endotoxic shock. HO-1 is known to increase during ARDS and the increase in HO-1 activity is thought to be a protective mechanism. In addition, ET-1, which was previously shown to increase inflammation and pulmonary-vascular leaks in ARDS, was reduced following Ang-1 cell therapy compared to LPS-challenged controls. ET-1 receptor antagonists have been shown to be protective in an experimental model of All, thus the mechanisms of protection of Ang-1 likely include modulation of the production of vasoactive factors.

Ang-1 cell therapy represents a therapeutic strategy to prevent development of clinical ARDS. Cell-based gene therapy could be advantageous over intravenous administration of recombinant Ang-1 protein, as it allows for more targeted expression of the transgene and overcomes issues of short protein half-life after injection. In addition, endothelial progenitor cells and mesenchymal stem cells may also provide protection above and beyond that provided by increased Ang-1 expression, as these cells may release many additional mediators that could be beneficial or participate directly in the repair and regeneration of the endothelial-epithelial barrier or exert immune modulatory effects that reduce lung inflammation and injury.

The benefits of Ang-1 overexpression were seen in two experimental models, showing reduced vascular endothelial inflammation and leak. Overexpression of Ang-1 blunted endothelial adhesion molecule expression, increased HO-1 and eNOS expression, and decreased ET-1 expression, as well as reduced airspace inflammation, reduced intra-alveolar septal thickening and reduced early mortality. Therefore, these results show that Ang-1 therapy is a viable new treatment strategy to reduce the vascular consequences of lung injury, which are a major determinant of morbidity and mortality in critically ill patients.

What is claimed is:

1. A process of alleviating a state selected from the group consisting of lung inflammation, septal edema, alveolar inflammation, and endothelial inflammation, in a mammalian patient, comprising administering to the lung by injection into the pulmonary circulation of the patient of syngeneic or allogeneic or autologous mesenchymal stem cells, said cells having been transformed in vitro to express angiopoeitin; wherein the administration results in alleviation of the state.

2. The process of claim 1 wherein the state is a result of, or caused by, acute lung injury.

3. The process of claim 1 wherein the state is associated with acute respiratory distress syndrome.

4. The process of claim 1 wherein the cells are allogenic.

5. The process of claim 1 wherein the cells are autologous.

* * * * *

SEQUENCE LISTING

<160> NUMBER OF SEQ ID NOS: 49

<210> SEQ ID NO 1
<211> LENGTH: 20
<212> TYPE: DNA
<213> ORGANISM: Artificial
<220> FEATURE:

```
<223> OTHER INFORMATION: Primer

<400> SEQUENCE: 1
tcgggcctcc gaaaccatga                                               20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
cctggtgaga gatctggttc                                               20

<210> SEQ ID NO 3
<211> LENGTH: 33
<212> TYPE: DNA
<213> ORGANISM: Artificial
<220> FEATURE:
<223> OTHER INFORMATION: Primer

<400> SEQUENCE: 3
cgctactggc ttatcgaaat taatacgact cac                                33

<210> SEQ ID NO 4
<211> LENGTH: 28
<212> TYPE: DNA
<213> ORGANISM: Artificial
<220> FEATURE:
<223> OTHER INFORMATION: Primer

<400> SEQUENCE: 4
ggccttggtg aggtttgatc cgcataat                                      28

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
ctctaaggct gtgggcaagg tcat                                          24

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
gagatccacc accctgttgc tgta                                          24

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
tcgggcctcc gaaaccatga                                               20
```

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
cctggtgaga gatctggttc          20

<210> SEQ ID NO 9
<211> LENGTH: 33
<212> TYPE: DNA
<213> ORGANISM: Artificial
<220> FEATURE:
<223> OTHER INFORMATION: Primer

<400> SEQUENCE: 9
cgctactggc ttatcgaaat taatacgact cac          33

<210> SEQ ID NO 10
<211> LENGTH: 28
<212> TYPE: DNA
<213> ORGANISM: Artificial
<220> FEATURE:
<223> OTHER INFORMATION: Primer

<400> SEQUENCE: 10
ggccttggtg aggtttgatc cgcataat          28

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
ctctaaggct gtgggcaagg tcat          24

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
gagatccacc accctgttgc tgta          24

<210> SEQ ID NO 13
<211> LENGTH: 18
<212> TYPE: DNA
<213> ORGANISM: Artificial
<220> FEATURE:
<223> OTHER INFORMATION: Primer

<400> SEQUENCE: 13
cgagcacgtg gatccatc          18

<210> SEQ ID NO 14
<211> LENGTH: 24
<212> TYPE: DNA
<213> ORGANISM: Artificial
<220> FEATURE:
<223> OTHER INFORMATION: Primer

```
<400> SEQUENCE: 14
catggatccg cgatggcttg ggcc                                          24

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15
cgctactggc ttatcgaaat taatacgact cac                                33

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16
ggccttggtg aggtttgatc cgcataat                                      28

<210> SEQ ID NO 17
<211> LENGTH: 25
<212> TYPE: DNA
<213> ORGANISM: Artificial
<220> FEATURE:
<223> OTHER INFORMATION: Primer

<400> SEQUENCE: 17
cgctctccct aagctggtag gtgcc                                         25

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
tgtacccgcg gccgcaattc c                                             21

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
attcgcgctt ggccttcctg tagcc                                         25

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
ctctaaggct gtgggcaagg tcat                                          24

<210> SEQ ID NO 21
<211> LENGTH: 24
```

-continued

<212> TYPE: DNA
<213> ORGANISM: Artifical
<220> FEATURE:
<223> OTHER INFORMATION: Primer

<400> SEQUENCE: 21
gagatccacc accctgttgc tgta                                      24

<210> SEQ ID NO 22
<211> LENGTH: 25
<212> TYPE: DNA
<213> ORGANISM: Artifical
<220> FEATURE:
<223> OTHER INFORMATION: Primer

<400> SEQUENCE: 22
gagctccttg agaattacct tgtgg                                     25

<210> SEQ ID NO 23
<211> LENGTH: 25
<212> TYPE: DNA
<213> ORGANISM: Artifical
<220> FEATURE:
<223> OTHER INFORMATION: Primer

<400> SEQUENCE: 23
cgagttgatt tagtacctgg gtctc                                     25

<210> SEQ ID NO 24
<211> LENGTH: 24
<212> TYPE: DNA
<213> ORGANISM: Artifical
<220> FEATURE:
<223> OTHER INFORMATION: Primer

<400> SEQUENCE: 24
ctccaatact caccctgtta tgtc                                      24

<210> SEQ ID NO 25
<211> LENGTH: 24
<212> TYPE: DNA
<213> ORGANISM: Artifical
<220> FEATURE:
<223> OTHER INFORMATION: Primer

<400> SEQUENCE: 25
gacactggaa cagtgtgaat ctgg                                      24

<210> SEQ ID NO 26
<211> LENGTH: 25
<212> TYPE: DNA
<213> ORGANISM: Artifical
<220> FEATURE:
<223> OTHER INFORMATION: Primer

<400> SEQUENCE: 26
agaacaacat aggatcaagc aaccc                                     25

<210> SEQ ID NO 27
<211> LENGTH: 28
<212> TYPE: DNA
<213> ORGANISM: Artifical
<220> FEATURE:
<223> OTHER INFORMATION: Primer

<400> SEQUENCE: 27

```
ctcttcagtt gcaacataat cagaaacg                                          28

<210> SEQ ID NO 28
<211> LENGTH: 25
<212> TYPE: DNA
<213> ORGANISM: Artificial
<220> FEATURE:
<223> OTHER INFORMATION: Primer

<400> SEQUENCE: 28
cagtgctgta ccatgatcag aatac                                             25

<210> SEQ ID NO 29
<211> LENGTH: 24
<212> TYPE: DNA
<213> ORGANISM: Artificial
<220> FEATURE:
<223> OTHER INFORMATION: Primer

<400> SEQUENCE: 29
gtaataggtg taaatggaca ccac                                              24

<210> SEQ ID NO 30
<211> LENGTH: 24
<212> TYPE: DNA
<213> ORGANISM: Artificial
<220> FEATURE:
<223> OTHER INFORMATION: Primer

<400> SEQUENCE: 30
acgagtgtga atcgaaaacc gaag                                              24

<210> SEQ ID NO 31
<211> LENGTH: 26
<212> TYPE: DNA
<213> ORGANISM: Artificial
<220> FEATURE:
<223> OTHER INFORMATION: Primer

<400> SEQUENCE: 31
gtattaccaa ggaggatgca aagtag                                            26

<210> SEQ ID NO 32
<211> LENGTH: 25
<212> TYPE: DNA
<213> ORGANISM: Artificial
<220> FEATURE:
<223> OTHER INFORMATION: Primer

<400> SEQUENCE: 32
gtgagtattc accctctaat agatg                                             25

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
ctctctagaa cttgtgaacc agaac                                             25

<210> SEQ ID NO 34
<211> LENGTH: 25
<212> TYPE: DNA
<213> ORGANISM: Artificial
```

```
<220> FEATURE:
<223> OTHER INFORMATION: Primer

<400> SEQUENCE: 34
agtcttcacg aacgctgcat atgac                                        25

<210> SEQ ID NO 35
<211> LENGTH: 25
<212> TYPE: DNA
<213> ORGANISM: Artificial
<220> FEATURE:
<223> OTHER INFORMATION: Primer

<400> SEQUENCE: 35
gaccaggaaa cttgttatct gcatg                                        25

<210> SEQ ID NO 36
<211> LENGTH: 25
<212> TYPE: DNA
<213> ORGANISM: Artificial
<220> FEATURE:
<223> OTHER INFORMATION: Primer

<400> SEQUENCE: 36
gagacgttcg atgttcgaag caaac                                        25

<210> SEQ ID NO 37
<211> LENGTH: 25
<212> TYPE: DNA
<213> ORGANISM: Artificial
<220> FEATURE:
<223> OTHER INFORMATION: Primer

<400> SEQUENCE: 37
gctttgttga ggtctagaga ctctg                                        25

<210> SEQ ID NO 38
<211> LENGTH: 23
<212> TYPE: DNA
<213> ORGANISM: Artificial
<220> FEATURE:
<223> OTHER INFORMATION: Primer

<400> SEQUENCE: 38
ctacgaagaa tggaagtggt tcc                                          23

<210> SEQ ID NO 39
<211> LENGTH: 24
<212> TYPE: DNA
<213> ORGANISM: Artificial
<220> FEATURE:
<223> OTHER INFORMATION: Primer

<400> SEQUENCE: 39
gtgctgagct gacagagtcg tacc                                         24

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
gaagaggaga tagagcgaaa caagc                                        25
```

```
<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
ctcgtggaga cgctttacgt agtgc                                          25

<210> SEQ ID NO 42
<211> LENGTH: 24
<212> TYPE: DNA
<213> ORGANISM: Artificial
<220> FEATURE:
<223> OTHER INFORMATION: Primer

<400> SEQUENCE: 42
gcttctacag tttcttgttc agac                                           24

<210> SEQ ID NO 43
<211> LENGTH: 24
<212> TYPE: DNA
<213> ORGANISM: Artificial
<220> FEATURE:
<223> OTHER INFORMATION: Primer

<400> SEQUENCE: 43
ggatgcaaac gaagacaggt tagg                                           24

<210> SEQ ID NO 44
<211> LENGTH: 23
<212> TYPE: DNA
<213> ORGANISM: Artificial
<220> FEATURE:
<223> OTHER INFORMATION: Primer

<400> SEQUENCE: 44
tttgtctccc agctgaccag tgg                                            23

<210> SEQ ID NO 45
<211> LENGTH: 23
<212> TYPE: DNA
<213> ORGANISM: Artificial
<220> FEATURE:
<223> OTHER INFORMATION: Primer

<400> SEQUENCE: 45
gacaggtaga agtgctcata cag                                            23

<210> SEQ ID NO 46
<211> LENGTH: 23
<212> TYPE: DNA
<213> ORGANISM: Artificial
<220> FEATURE:
<223> OTHER INFORMATION: Primer

<400> SEQUENCE: 46
cataggagag atgagcttcc tgc                                            23

<210> SEQ ID NO 47
<211> LENGTH: 27
<212> TYPE: DNA
<213> ORGANISM: Artificial
<220> FEATURE:
<223> OTHER INFORMATION: Primer
```

```
<400> SEQUENCE: 47
ctctgaacaa ggctcacagt gattttc                                           27

<210> SEQ ID NO 48
<211> LENGTH: 24
<212> TYPE: DNA
<213> ORGANISM: Artificial
<220> FEATURE:
<223> OTHER INFORMATION: Primer

<400> SEQUENCE: 48
gacgatcaga taccgtcgta gttc                                              24

<210> SEQ ID NO 49
<211> LENGTH: 24
<212> TYPE: DNA
<213> ORGANISM: Artificial
<220> FEATURE:
<223> OTHER INFORMATION: Primer

<400> SEQUENCE: 49
gtttcagctt tgcaaccata ctcc                                              24
```